United States Patent
Liao et al.

(10) Patent No.: US 10,662,187 B2
(45) Date of Patent: May 26, 2020

(54) BRUTON'S TYROSINE KINASE INHIBITORS

(71) Applicants: Zibo Biopolar Changsheng Pharmaceutical Co. Ltd., Zibo, Shangdong (CN); Shanghai Institute of Materia Medica, Chinese Academy of Sciences, Shanghai (CN)

(72) Inventors: Xibin Liao, Edison, NJ (US); Jia Li, Shanghai (CN); Zhijian Lu, Plainfield, IN (US); Yubo Zhou, Shanghai (CN); Anhui Gao, Shanghai (CN)

(73) Assignees: Zibo Biopolar Changsheng Pharmaceutical Co. Ltd., Zibo (CN); Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/070,520

(22) PCT Filed: Jan. 17, 2017

(86) PCT No.: PCT/US2017/013815
§ 371 (c)(1),
(2) Date: Jul. 16, 2018

(87) PCT Pub. No.: WO2017/127371
PCT Pub. Date: Jul. 27, 2017

(65) Prior Publication Data
US 2019/0062328 A1    Feb. 28, 2019

Related U.S. Application Data

(60) Provisional application No. 62/281,252, filed on Jan. 21, 2016.

(51) Int. Cl.
| | | |
|---|---|---|
| *C07D 471/04* | (2006.01) | |
| *C07D 231/56* | (2006.01) | |
| *A61K 45/06* | (2006.01) | |
| *A61K 31/437* | (2006.01) | |
| *A61K 31/42* | (2006.01) | |
| *A61K 31/4545* | (2006.01) | |
| *A61K 31/496* | (2006.01) | |
| *A61K 31/519* | (2006.01) | |
| *A61P 35/00* | (2006.01) | |
| *A61P 37/00* | (2006.01) | |

(52) U.S. Cl.
CPC ............ *C07D 471/04* (2013.01); *A61K 31/42* (2013.01); *A61K 31/437* (2013.01); *A61K 31/4545* (2013.01); *A61K 31/496* (2013.01); *A61K 31/519* (2013.01); *A61K 45/06* (2013.01); *A61P 35/00* (2018.01); *A61P 37/00* (2018.01); *C07D 231/56* (2013.01)

(58) Field of Classification Search
CPC .... C07D 471/04; C07D 231/56; A61K 45/06; A61K 31/519; A61K 31/496; A61K 31/4545; A61K 31/42; A61K 31/437; A61K 31/06; A61K 2300/00; A61P 37/00; A61P 35/00
See application file for complete search history.

(56) References Cited

U.S. PATENT DOCUMENTS

| | | | |
|---|---|---|---|
| 7,718,662 B1 | 5/2010 | Chen et al. | |
| 8,377,946 B1 | 2/2013 | Chen et al. | |
| 8,673,925 B1 | 3/2014 | Goldstein | |
| 10,538,524 B2 * | 1/2020 | Calder | ................. A61K 31/519 |
| 2012/0129852 A1 | 5/2012 | Duan et al. | |

FOREIGN PATENT DOCUMENTS

| | | | | |
|---|---|---|---|---|
| EP | 2487159 A1 * | 8/2012 | ........... | C07D 231/56 |
| WO | 2002080926 A1 | 10/2002 | | |
| WO | 2004113303 A1 | 12/2004 | | |
| WO | 2008039218 A2 | 4/2008 | | |
| WO | WO-2012106995 A1 * | 8/2012 | ........... | C07D 231/56 |
| WO | 2013113097 A1 | 8/2013 | | |
| WO | 2014022569 A1 | 2/2014 | | |
| WO | WO-2014026327 A1 * | 2/2014 | ........... | C07D 231/56 |
| WO | WO-2014026329 A1 * | 2/2014 | ........... | C07D 231/56 |
| WO | WO-2014028589 A2 * | 2/2014 | ........... | C07D 231/56 |
| WO | WO-2014028591 A2 * | 2/2014 | ........... | C07D 231/56 |
| WO | 2015061751 A1 | 4/2015 | | |
| WO | WO-2016170545 A1 * | 10/2016 | ........... | C07D 487/04 |

OTHER PUBLICATIONS

Scheepstra, M., "Identification of an allosteric binding site for RORγt inhibition." Nature communications 6 (2015): 8833.*
McKim, A. S.,"Dimethyl sulfoxide USP, PhEur in approved pharmaceutical products and medical devices." Pharmaceutical Technology 32.5 (2008): 74.*
CAS Registry Chemical Abstracts Service; Registry number excerpts accessed online (2019) p. 1.*
Pubchem-CID 67079916 Create Date: Nov. 30, 2012, p. 4, Fig.
Pubchem-CID 90054158 Create Date: Feb. 13, 2015, p. 4, Fig.

* cited by examiner

*Primary Examiner* — John M Mauro
(74) *Attorney, Agent, or Firm* — SZDC Law P.C.

(57) ABSTRACT

Bruton's tyrosine kinase (Btk) inhibitors have the following Formula (I):

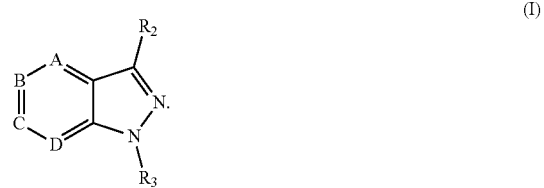

10 Claims, No Drawings

BRUTON'S TYROSINE KINASE INHIBITORS

This application is a national stage application of PCT/US2017/013815, filed on Jan. 17, 2017, which claims priority to U.S. Provisional Patent Application No. 62/281,252, filed on Jan. 21, 2016, which is incorporated by reference for all purposes as if fully set forth herein.

FIELD OF THE INVENTION

Described herein are Bruton's tyrosine kinase inhibitors, methods of making such inhibitors, and pharmaceutical compositions containing such inhibitors.

BACKGROUND OF THE INVENTION

Bruton's tyrosine kinase (Btk) plays an important role in signal transduction in B cells and is a factor that contributes to the survival, differentiation, proliferation, and activation of B cells. There is currently a need for methods of treating diseases in which B cells or mast cells participate. Btk is also known to participate in mast cell activation and in the physiological functions of platelets. Therefore, Btk inhibitors are effective for the treatment of diseases in which B cells or mast cells participate, for example, allergic diseases, autoimmune diseases, inflammatory diseases, thromboembolic diseases, and cancers.

SUMMARY OF THE INVENTION

The Btk inhibitors described herein have the following Formula (I):

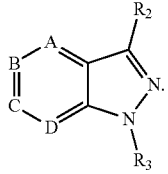

(I)

In Formula (I), A is N or $CR^1$; B, C, and D are each N or C—H, with the proviso that only one or two of A, B, C, and D can be N. $R^1$ is hydrogen, amino, OH, CN, —NHOH or $CONH_2$; $R^2$ is

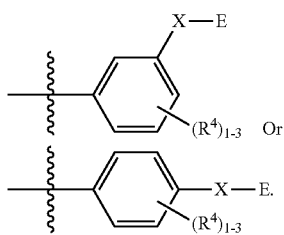

—X-E is one of the followings: (1) X is O, $OCR^aR^b$, S(O), $S(O)_2$, $CR^aR^b$, $CR^aR^bO$, $NR^c(C=O)$, $C=ONR^c$ or a bond; and E is a hydrogen, an aryl or a heteroaryl substituted with one to three $R^5$ substituents; or a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or (2) —X-E is hydrogen, halogen, $—OR^a$, $—O(CH_2)_{1-4}R^a$, —CN, $—NO_2$. $R^4$ and $R^5$ are each independently selected from the group consisting of hydrogen, halogen, hydroxy, cyano, $OCF_3$, $OCF_2H$, $C_{1-6}$ alkyl, optionally substituted with one to five fluorines, $C_{3-6}$ cycloalkyl, optionally substituted with one to five fluorines, $C_{1-4}$ alkoxy, optionally substituted with one to five fluorines, $C_{1-4}$ alkylthio, optionally substituted with one to five fluorines, $C_{1-4}$ alkylsulfonyl, optionally substituted with one to five fluorines, carboxy, $C_{1-4}$ alkyloxycarbonyl, and $C_{1-4}$ alkylcarbonyl. $R^a$ and $R^b$ are each independently hydrogen, fluorine, or $C_{1-3}$ alkyl, optionally substituted with one to five fluorines. $R^c$ is hydrogen or $C_{1-3}$ alkyl, optionally substituted with one to five fluorines. $R^3$ is a group having a double bond.

Further described is an isomer or tautomer thereof, a pharmaceutical acceptable solvate thereof, or a pharmaceutical acceptable prodrug thereof.

In one aspect, in Formula (I), E is selected from aryl, heteroaryl, carbocyclyl, heterocyclyl, any of which is optionally substituted with one to three $R^5$ substituents. In another aspect, in Formula (I), $R^3$ is selected from the group consisting of:

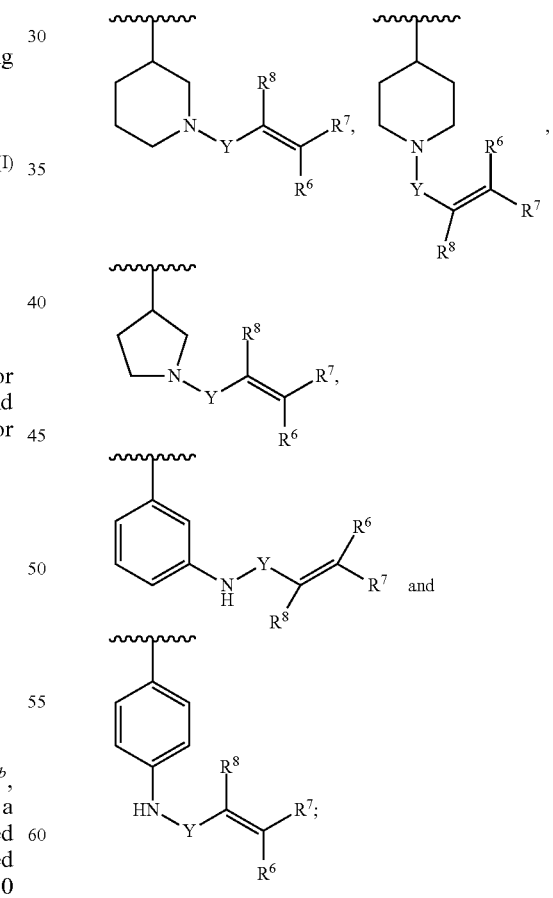

Y is C(=O); OC(=O), NHC(=O), S=O, $S(=O)_2$, or $NHS(=O)_2$; $R^6$, $R^7$, $R^8$ are each independently hydrogen, halogen, CN, $C_{1-4}$ alkyl, $C_{1-6}$ alkoxyalkyl, $C_{1-8}$ alkylaminoalkyl, or $C_{1-4}$ alkylphenyl; or $R^7$ and $R^8$ taken together form a bond.

In another aspect, in Formula (I), $R^3$ is selected from the group consisting of:

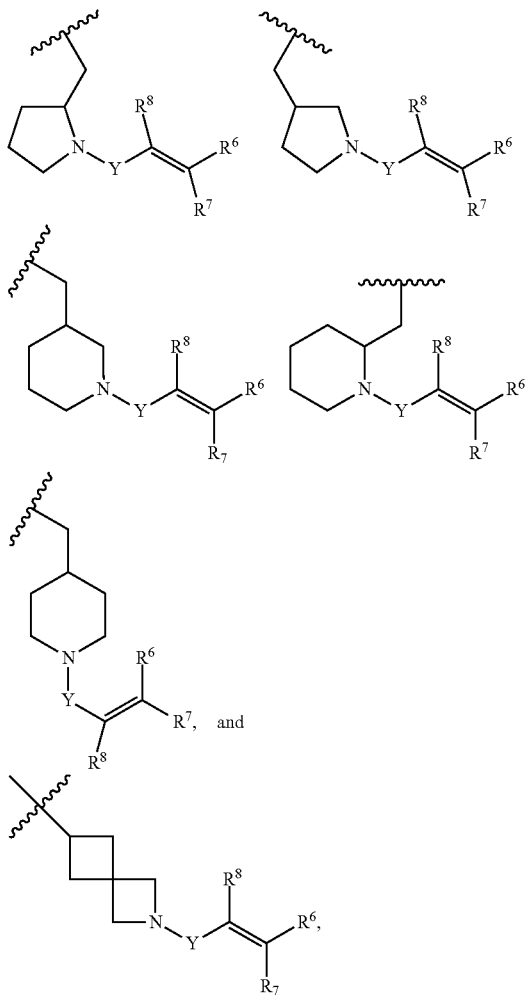

Y is C(=O); OC(=O), NHC(=O), S=O, S(=O)$_2$, or NHS(=O)$_2$; $R^6$, $R^7$, $R^8$ are each independently hydrogen, halogen, CN, $C_{1-4}$ alkyl, $C_{1-6}$ alkoxyalkyl, $C_{1-8}$ alkyl aminoalkyl, or $C_{1-4}$ alkylphenyl; and $R^7$ and $R^8$ can be optionally taken together form a bond.

In another aspect, in Formula (I), $R^3$ is selected from the group consisting of:

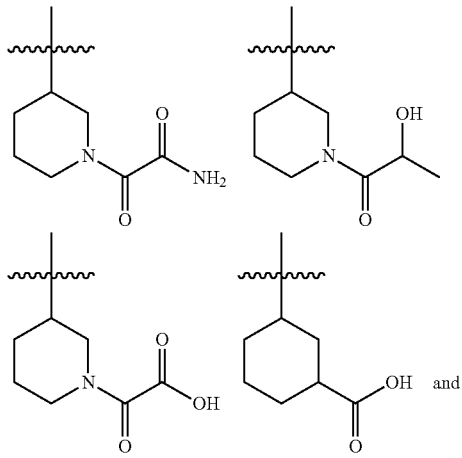

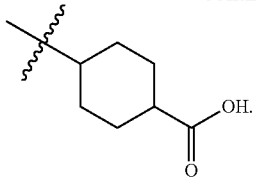

In another aspect, in Formula (I), A is $CR^1$, and one of B, C, and D is N.

In another aspect, in Formula (I), A is $CR^1$, B is N, and C and D are C—H.

In another aspect, described herein is a pharmaceutical composition including a therapeutically effective amount of the compound of Formula (I), and a pharmaceutically acceptable excipient.

In another aspect, described herein is a method for treating an autoimmune disease comprising administering to a subject in need thereof a composition containing a therapeutically effective amount of the compound of Formula (I) and other therapeutic agents.

In another aspect, the Btk inhibitors described herein are selected from the group consisting of (R)-1-(3-(3-(4-phenoxyphenyl)-1H-pyrazolo[4,3-c]pyridin-1-yl)pyrrolidin-1-yl)prop-2-en-1-one; (R)-1-(3-(3-(4-(2-chloro-3-methoxyphenoxy)phenyl)-1H-pyrazolo[4,3-c]pyridin-1-yl)piperidin-1-yl)prop-2-en-1-one; (R)-1-(3-(3-(4-(2-fluoro-3-methoxyphenoxy)phenyl)-1H-pyrazolo[4,3-c]pyridin-1-yl)pyrrolidin-1-yl)prop-2-en-1-one; (R)-1-(3-(3-(4-(2-fluoro-3-methoxyphenoxy)phenyl)-1H-pyrazolo[4,3-c]pyridin-1-yl)pyrrolidin-1-yl)prop-2-en-1-one; (R)-1-(3-(3-(4-(2-fluoro-3-methoxyphenoxy)phenyl)-7-methyl-1H-pyrazolo[4,3-c]pyridin-1-yl)pyrrolidin-1-yl) prop-2-en-1-one; (R)-1-(3-(3-(4-(2-fluoro-3-methoxyphenoxy)phenyl)-1H-pyrazolo[4,3-c]pyridin-1-yl)piperidin-1-yl)prop-2-en-1-one; (R)-1-(3-(3-(4-(naphthalen-1-yloxy)phenyl)-1H-pyrazolo[4,3-c]pyridin-1-yl)pyrrolidin-1-yl)prop-2-en-1-one; (R)-1-(3-(3-(4-(benzo[d][1,3]dioxol-4-yloxy)phenyl)-1H-pyrazolo[4,3-c]pyridin-1-yl)piperidin-1-yl)prop-2-en-1-one; (R)-1-(3-(3-(4-(3-chlorophenoxy)phenyl)-1H-pyrazolo[4,3-c]pyridin-1-yl)piperidin-1-yl)prop-2-en-1-one; (R)-1-(3-(3-(4-(m-tolyloxy)phenyl)-1H-pyrazolo[4,3-c]pyridin-1-yl)pyrrolidin-1-yl)prop-2-en-1-one; (R)-1-(3-(3-(3-chloro-4-phenoxyphenyl)-1H-pyrazolo[4,3-c]pyridin-1-yl)pyrrolidin-1-yl)prop-2-en-1-one; (R)-1-(3-(3-(4-(2,3-difluorophenoxy)phenyl)-1H-pyrazolo[4,3-c]pyridin-1-yl)piperidin-1-yl)prop-2-en-1-one; (R)-1-(3-(3-(4-(2,3-dimethylphenoxy)phenyl)-1H-pyrazolo[4,3-c]pyridin-1-yl)pyrrolidin-1-yl)prop-2-en-1-one; (R)-1-(3-(3-(4-(2,3-difluorophenoxy)phenyl)-1H-pyrazolo[4,3-c]pyridin-1-yl)pyrrolidin-1-yl)prop-2-en-1-one; (R)-1-(3-(3-(4-(3-chloro-2-fluorophenoxy)phenyl)-1H-pyrazolo[4,3-c]pyridin-1-yl)pyrrolidin-1-yl)prop-2-en-1-one; R)-1-(3-(3-(4-(3-chloro-2-fluorophenoxy)phenyl)-1H-pyrazolo[4,3-c]pyridin-1-yl)piperidin-1-yl)prop-2-en-1-one; 1-(3-((3-(4-phenoxyphenyl)-1H-pyrazolo[4,3-c]pyridin-1-yl)methyl)pyrrolidin-1-yl)prop-2-en-1-one; (R)-1-(3-(3-(4-(2-chloro-3-methoxyphenoxy)phenyl)-1H-pyrazolo[4,3-c]pyridin-1-yl)pyrrolidin-1-yl)prop-2-en-1-one; (R)-1-(3-(3-(4-(3-fluoro-2-methylphenoxy)phenyl)-1H-pyrazolo[4,3-c]pyridin-1-yl)pyrrolidin-1-yl)prop-2-en-1-one; 1-(4-(3-(4-phenoxyphenyl)-1H-pyrazolo[4,3-c]pyridin-1-yl)piperidin-1-yl)prop-2-en-1-one; (R)-1-(3-(3-(4-(3-fluoro-2-methylphenoxy)phenyl)-1H-pyrazolo[4,3-c]pyridin-1-yl)piperidin-1-yl)prop-2-en-1-one; N-(3-(3-(4- phenoxyphenyl)-1H-pyrazolo[4,3-c]pyridin-1-yl)phenyl) acrylamide; (R)-1-(3-(3-(4-(3-isopropoxyphenoxy)phenyl)-1H-pyrazolo[4,3-c]pyridin-1-yl)piperidin-1-yl)prop-2-en-1-one; (R)-1-(3-(3-(4-(2,3-dimethylphenoxy)phenyl)-1H-pyrazolo[4,3-c]pyridin-1-yl)piperidin-1-yl)prop-2-en-1-one; (R)-1-(3-(3-(4-(2-chloro-3-methoxyphenoxy)phenyl)-1H-pyrazolo[4,3-c]pyridin-1-yl)piperidin-1-yl)but-2-yn-1-one; 1-(6-(3-(4-(2-fluoro-3-methoxyphenoxy)phenyl)-1H-pyrazolo[4,3-c]pyridin-1-yl)-2-azaspiro[3.3]heptan-2-yl)prop-2-en-1-one; (R)-1-(3-(7-chloro-3-(4-(2-fluoro-3-methoxyphenoxy)phenyl)-1H-pyrazolo[4,3-c]pyridin-1-yl)pyrrolidin-1-yl)prop-2-en-1-one; (R)-1-(1-acryloylpyrrolidin-3-yl)-3-(4-(2-fluoro-3-methoxyphenoxy)phenyl)-1H-pyrazolo[4,3-c]pyridine-7-carbonitrile; (R)-1-(3-(3-(4-(cyclohexyloxy)phenyl)-1H-pyrazolo[4,3-c]pyridin-1-yl)piperidin-1-yl)prop-2-en-1-one; 1-(6-(3-(4-(2-chloro-3-methoxyphenoxy)phenyl)-1H-pyrazolo[4,3-c]pyridin-1-yl)-2-azaspiro[3.3]heptan-2-yl)prop-2-en-1-one; (R)-1-(3-(3-(4-((2,3-dihydro-1H-inden-4-yl)oxy)phenyl)-1H-pyrazolo[4,3-c]pyridin-1-yl)pyrrolidin-1-yl)prop-2-en-1-one; (R)-1-(3-(3-(4-(2-fluoro-3-methoxyphenoxy)phenyl)-1H-pyrazolo[3,4-c]pyridin-1-yl)pyrrolidin-1-yl)prop-2-en-1-one; (R)-1-(3-(3-(4-phenoxyphenyl)-1H-pyrazolo[4,3-c]pyridin-1-yl)piperidin-1-yl)prop-2-en-1-one; (S)-1-(3-(3-(4-((3-chlorophenyl)thio)phenyl)-1H-pyrazolo[4,3-c]pyridin-1-yl)pyrrolidin-1-yl)prop-2-en-1-one; (S)-1-(3-(3-(3-chloro-4-phenoxyphenyl)-1H-pyrazolo[4,3-c]pyridin-1-yl)piperidin-1-yl)prop-2-en-1-one; (S)-1-(3-(3-(4-(3-chlorophenoxy)phenyl)-1H-pyrazolo[4,3-c]pyridin-1-yl)pyrrolidin-1-yl)prop-2-en-1-one; (S)-1-(3-(3-(4-(m-tolyloxy)phenyl)-1H-pyrazolo[4,3-c]pyridin-1-yl)piperidin-1-yl)prop-2-en-1-one; (R)-1-(3-(3-(4-(2-chloro-3-fluorophenoxy)phenyl)-2H-pyrazolo[4,3-c]pyridin-2-yl)pyrrolidin-1-yl)prop-2-en-1-one; (R)-1-(3-(3-(4-(2-chloro-3-fluorophenoxy)phenyl)-2H-pyrazolo[4,3-c]pyridin-2-yl)piperidin-1-yl)prop-2-en-1-one; (S)-1-(3-(3-(4-(2-chloro-3-fluorophenoxy)phenyl)-1H-pyrazolo[4,3-c]pyridin-1-yl)piperidin-1-yl)prop-2-en-1-one; (R)-1-(3-(3-(4-(2,3-dichlorophenoxy)phenyl)-2H-pyrazolo[4,3-c]pyridin-2-yl)pyrrolidin-1-yl)prop-2-en-1-one; (R)-1-(3-(3-(4-(2,3-dichlorophenoxy)phenyl)-2H-pyrazolo[4,3-c]pyridin-2-yl)pyrrolidin-1-yl)prop-2-en-1-one; (S)-1-(3-(3-(4-(2,3-dichlorophenoxy)phenyl)-1H-pyrazolo[4,3-c]pyridin-1-yl)pyrrolidin-1-yl)prop-2-en-1-one; (R)-1-(3-(3-(4-(2,3-dichlorophenoxy)phenyl)-2H-pyrazolo[4,3-c]pyridin-2-yl)piperidin-1-yl)prop-2-en-1-one; (S)-1-(3-(3-(4-(2,3-dichlorophenoxy)phenyl)-1H-pyrazolo[4,3-c]pyridin-1-yl)piperidin-1-yl)prop-2-en-1-one; (R)-1-(3-(3-(4-((2-fluorobenzyl)oxy)phenyl)-1H-pyrazolo[4,3-c]pyridin-1-yl)pyrrolidin-1-yl)prop-2-en-1-one; (R)-1-(3-(3-(4-((2-fluorobenzyl)oxy)phenyl)-1H-pyrazolo[4,3-c]pyridin-1-yl)piperidin-1-yl)prop-2-en-1-one; (R)-4-(1-(1-acryloylpyrrolidin-3-yl)-1H-pyrazolo[4,3-c]pyridin-3-yl)-N-(3-methoxybenzyl)benzamide; (R)-4-(1-(1-acryloylpiperidin-3-yl)-1H-pyrazolo[4,3-c]pyridin-3-yl)-N-(3-methoxybenzyl)benzamide; (R)-1-(3-(3-(3'-methyl[1,1'-biphenyl]-4-yl)-1H-pyrazolo[4,3-c]pyridin-1-yl)piperidin-1-yl)prop-2-en-1-one: (R)-1-(3-(3-(3'-methyl-[1,1'-biphenyl]-4-yl)-2H-pyrazolo[4,3-c]pyridin-2-yl)pyrrolidin-1-yl)prop-2-en-1-one; (R)-1-(3-(3-(3'-methyl-[1,1'-biphenyl]-4-yl)-1H-pyrazolo[4,3-c]pyridin-1-yl)pyrrolidin-1-yl)prop-2-en-1-one; N-{4-[1-(1-Acryloyl-pyrrolidin-3-yl)-1H-pyrazolo[4,3-c]pyridin-3-yl]-phenyl}-3-trifluoromethyl-benzamide (R)—N-(4-(1-(1-acryloylpiperidin-3-yl)-1H-pyrazolo[4,3-c]pyridin-3-yl)phenyl)-3-(trifluoromethyl)benzamide; (R)-1-(3-(5-acetyl-3-(4-(2-fluoro-3-methoxyphenoxy)phenyl)-4,5,6,7-tetrahydro-1H-pyrazolo[4,3-c]pyridin-1-yl)pyrrolidin-1-yl)prop-2-en-1-one; (R)-1-(3-(5-acryloyl-3-(4-(2-fluoro-3-methoxyphenoxy)phenyl)-4,5,6,7-tetrahydro-1H-pyrazolo[4,3-c]pyridin-1-yl)pyrrolidin-1-yl)prop-2-en-1-one; (R)-1-(3-(3-(4-(2-fluoro-3-methylphenoxy)phenyl)-1H-pyrazolo[4,3-c]pyridin-1-yl)pyrrolidin-1-yl)prop-2-en-1-one; (R)-1-(3-(3-(4-(2-fluoro-3-methylphenoxy)phenyl)-1H-pyrazolo[4,3-c]pyridin-1-yl)piperidin-1-yl)prop-2-en-1-one; (R)-1-(3-(3-(4-(3-fluoro-2-methoxyphenoxy)phenyl)-1H-pyrazolo[4,3-c]pyridin-1-yl)pyrrolidin-1-yl)prop-2-en-1-one; (R)-1-(3-(3-(4-(3-fluoro-2-methoxyphenoxy)phenyl)-1H-pyrazolo[4,3-c]pyridin-1-yl)piperidin-1-yl)prop-2-en-1-one; (R)-1-(3-(3-(3-fluoro-4-phenoxyphenyl)-1H-pyrazolo[4,3-c]pyridin-1-yl)piperidin-1-yl)prop-2-en-1-one; 1-(3-(3-(4-phenoxyphenyl)-1H-pyrazolo[4,3-c]pyridin-1-yl)azetidin-1-yl)prop-2-en-1-one; 1-(3-((3-(4-phenoxyphenyl)-1H-pyrazolo[4,3-c]pyridin-1-yl)methyl)piperidin-1-yl)prop-2-en-1-one; (R)-1-(3-(4-amino-3-(4-phenoxyphenyl)-1H-indazol-1-yl)pyrrolidin-1-yl)prop-2-en-1-one; (R)-1-(3-(4-amino-3-(4-phenoxyphenyl)-1H-indazol-1-yl)piperidin-1-yl)prop-2-en-1-one; (R)-1-(3-(3-(4-(3-chloro-2-methylphenoxy)phenyl)-1H-pyrazolo[4,3-c]pyridin-1-yl)piperidin-1-yl)prop-2-en-1-one; (R)-1-(3-(3-(4-(3-methoxy-2-methylphenoxy)phenyl)-1H-pyrazolo[4,3-c]pyridin-1-yl)piperidin-1-yl)prop-2-en-1-one; (R)-1-(3-(3-(4-((3-fluorophenyl)thio)phenyl)-1H-pyrazolo[4,3-c]pyridin-1-yl)pyrrolidin-1-yl)prop-2-en-1-one; (R)-1-(3-(3-(4-(3-methoxy-2-methylphenoxy)phenyl)-1H-pyrazolo[4,3-c]pyridin-1-yl)pyrrolidin-1-yl)prop-2-en-1-one; (R)-1-(3-(3-(4-(3-chloro-2-methylphenoxy)phenyl)-1H-pyrazolo[4,3-c]pyridin-1-yl)pyrrolidin-1-yl)prop-2-en-1-one; (R)-1-(3-(3-(3-fluoro-4-phenoxyphenyl)-1H-pyrazolo[4,3-c]pyridin-1-yl)pyrrolidin-1-yl)prop-2-en-1-one; (R)-1-(3-(3-(4-(3-fluorophenoxy)phenyl)-1H-pyrazolo[4,3-c]pyridin-1-yl)piperidin-1-yl)prop-2-en-1-one; (R)-1-(3-(3-(4-(3-fluorophenoxy)phenyl)-1H-pyrazolo[4,3-c]pyridin-1-yl)pyrrolidin-1-yl)prop-2-en-1-one; (R)-1-(3-(3-(4-(3-methoxyphenoxy)phenyl)-1H-pyrazolo[4,3-c]pyridin-1-yl)pyrrolidin-1-yl)prop-2-en-1-one; (R)-1-(3-(3-(4-(3-methoxyphenoxy)phenyl)-1H-pyrazolo[4,3-c]pyridin-1-yl)piperidin-1-yl)prop-2-en-1-one; ((R)-1-(3-(7-fluoro-3-(4-phenoxyphenyl)-1H-pyrazolo[4,3-c]pyridin-1-yl)pyrrolidin-1-yl)prop-2-en-1-one; (R)-1-(3-(7-(difluoromethyl)-3-(4-(2-fluoro-3-methoxyphenoxy)phenyl)-1H-pyrazolo[4,3-c]pyridin-1-yl)pyrrolidin-1-yl)prop-2-en-1-one; R)-1-(3-(3-(4-(2-chloro-3-methoxyphenoxy)phenyl)-7-fluoro-1H-pyrazolo[4,3-c]pyridin-1-yl)pyrrolidin-1-yl)prop-2-en-1-one; (R)-1-(3-(3-(4-(2-chloro-3-methoxyphenoxy)phenyl)-7-methoxy-1H-pyrazolo[4,3-c]pyridin-1-yl)pyrrolidin-1-yl)prop-2-en-1-one; (R)-1-(3-(3-(4-(4-methylpiperazin-1-yl)phenyl)-1H-pyrazolo[4,3-c]pyridin-1-yl)pyrrolidin-1-yl)prop-2-en-1-one; (R)-1-(3-(7-fluoro-3-(4-(2-fluoro-3-methoxyphenoxy)phenyl)-1H-pyrazolo[4,3-c]pyridin-1-yl)piperidin-1-yl)prop-2-en-1-one; (R)-1-(3-(3-(4-(4-methylpiperazin-1-yl)phenyl)-1H-pyrazolo[4,3-c]pyridin-1-yl)piperidin-1-yl)prop-2-en-1-one; (R)-1-(3-(3-(3-(4-([1,4'-bipiperidin]-1'-yl)phenyl)-1H-pyrazolo[4,3-c]pyridin-1-yl)piperidin-1-yl)prop-2-en-1-one; (R)-1-(3-(3-(3-fluoro-4-(4-methylpiperazin-1-yl)phenyl)-1H-pyrazolo[4,3-c]pyridin-1-yl)piperidin-1-yl)prop-2-en-1-one; 1-(3-(3-(4-(2-fluoro-3-methoxyphenoxy)phenyl)-7-methoxy-1H-pyrazolo[4,3-c]pyridin-1-yl)piperidin-1-yl)prop-2-en-1-one; (R)-1-(3-(3-(4-(4-(methylsulfonyl)piperazin-1-yl)phenyl)-1H-pyrazolo[4,3-c]pyridin-1-yl)piperidin-1-yl)prop-2-en-1-one; (R)-1-(3-(3-(2-methoxy-4-(4-methylpiperazin-1-yl)phenyl)-1H-pyrazolo[4,3-c]pyridin-1-yl)piperidin-1-yl)prop-2-en-1- one; (R)-4-(1-(1-(but-2-ynoyl)piperidin-3-yl)-1H-pyrazolo [4,3-c]pyridin-3-yl)-N-(pyridin-2-yl)benzamide; (R)-1-(3-(7-(difluoromethyl)-3-(4-(2-fluoro-3-methoxyphenoxy) phenyl)-1H-pyrazolo[4,3-c]pyridin-1-yl)piperidin-1-yl) prop-2-en-1-one; (R)-1-(3-(3-(4-(2-fluoro-3-methoxyphenoxy)phenyl)-7-isopropoxy-1H-pyrazolo[4,3-c]pyridin-1-yl)piperidin-1-yl)prop-2-en-1-one; (R)-1-(3-(7-ethoxy-3-(4-(2-fluoro-3-methoxyphenoxy)phenyl)-1H-pyrazolo[4,3-c]pyridin-1-yl)piperidin-1-yl)prop-2-en-1-one; (R)-(3-(3-(4-(2-fluoro-3-methoxyphenoxy)phenyl)-7-methoxy-1H-pyrazolo[4,3-c]pyridin-1-yl)piperidin-1-yl)(2-tosyl-2-azaspiro[3.3]heptan-6-yl)methanone; (R)-1-(3-(3-((4-(4-methylpiperazin-1-yl)phenyl)amino)-1H-pyrazolo[4,3-c]pyridin-1-yl)piperidin-1-yl)prop-2-en-1-one; (R)-1-(3-(3-(4-(2-chloro-3-methoxyphenoxy)phenyl)-7-methoxy-1H-pyrazolo[4,3-c]pyridin-1-yl)piperidin-1-yl)prop-2-en-1-one; (R)-1-(3-(7-butoxy-3-(4-(2-fluoro-3-methoxyphenoxy) phenyl)-1H-pyrazolo[4,3-c]pyridin-1-yl)piperidin-1-yl) prop-2-en-1-one; (R)-1-(3-(3-(4-(2-fluoro-3-methoxyphenoxy)phenyl)-7-propoxy-1H-pyrazolo[4,3-c] pyridin-1-yl)piperidin-1-yl)prop-2-en-1-one; (R)-1-(3-(3-(4-(2-fluoro-3-methoxyphenoxy)phenyl)-4-methyl-1H-pyrazolo[4,3-c]pyridin-1-yl)piperidin-1-yl)prop-2-en-1-one; (R)-1-(3-(3-(4-(2-fluoro-3-methoxyphenoxy)phenyl)-7-methoxy-1H-pyrazolo[4,3-c]pyridin-1-yl)pyrrolidin-1-yl) prop-2-en-1-one; (R)-1-(3-(7-ethoxy-3-(4-(2-fluoro-3-methoxyphenoxy)phenyl)-1H-pyrazolo[4,3-c]pyridin-1-yl) pyrrolidin-1-yl)prop-2-en-1-one; (R)-1-(3-(3-(4-(2-chloro-3-methoxyphenoxy)phenyl)-7-ethoxy-1H-pyrazolo[4,3-c] pyridin-1-yl)pyrrolidin-1-yl)prop-2-en-1-one; (R)-1-(3-(3-(4-(2-chloro-3-methoxyphenoxy)phenyl)-7-ethoxy-1H-pyrazolo[4,3-c]pyridin-1-yl)piperidin-1-yl)prop-2-en-1-one; (R)-1-(3-(3-(4-(2-fluoro-3-methoxyphenoxy)phenyl)-7-hydroxy-1H-pyrazolo[4,3-c]pyridin-1-yl)piperidin-1-yl) prop-2-en-1-one; (R)-1-(3-(3-(4-(2-chloro-3-methoxyphenoxy)phenyl)-7-propoxy-1H-pyrazolo[4,3-c] pyridin-1-yl)piperidin-1-yl)prop-2-en-1-one; (R)-1-(3-(7-butoxy-3-(4-(2-chloro-3-methoxyphenoxy)phenyl)-1H-pyrazolo[4,3-c]pyridin-1-yl)piperidin-1-yl)prop-2-en-1-one; (R)-1-(3-(3-(4-(2-chloro-3-methoxyphenoxy)phenyl)-7-isopropoxy-1H-pyrazolo[4,3-c]pyridin-1-yl)piperidin-1-yl)prop-2-en-1-one; (R)-1-(3-(3-(4-(2-fluoro-3-methoxyphenoxy)phenyl)-7-(2-hydroxyethoxy)-1H-pyrazolo[4,3-c]pyridin-1-yl)piperidin-1-yl)prop-2-en-1-one; 1-((3R)-3-(3-(4-(2-fluoro-3-methoxyphenoxy)phenyl)-7-((tetrahydrofuran-3-yl)oxy)-1H-pyrazolo[4,3-c]pyridin-1-yl)piperidin-1-yl)prop-2-en-1-one; 1-((3R)-3-(3-(4-(2-chloro-3-methoxyphenoxy)phenyl)-7-((tetrahydrofuran-3-yl)oxy)-1H-pyrazolo[4,3-c]pyridin-1-yl)piperidin-1-yl) prop-2-en-1-one; (R)-1-(3-(7-(2-amino ethoxy)-3-(4-(2-fluoro-3-methoxyphenoxy)phenyl)-1H-pyrazolo[4,3-c] pyridin-1-yl)piperidin-1-yl)prop-2-en-1-one; (R)-1-(3-(3-(4-(3-methoxy-2-propoxyphenoxy)phenyl)-7-propoxy-1H-pyrazolo[4,3-c]pyridin-1-yl)piperidin-1-yl)prop-2-en-1-one; (R)-1-(3-(3-(4-(2-fluoro-3-methoxyphenoxy)phenyl)-7-methoxy-1H-pyrazolo[4,3-c]pyridin-1-yl)piperidin-1-yl) propan-1-one; 1-(3-(3-(4-(2-fluoro-3-methoxyphenoxy) phenyl)-7-methoxy-1H-pyrazolo[4,3-c]pyridin-1-yl) piperidin-1-yl)-2-hydroxypropan-1-one; 2-(3-(3-(4-(2-fluoro-3-methoxyphenoxy)phenyl)-7-methoxy-1H-pyrazolo [4,3-c]pyridin-1-yl)piperidin-1-yl)-2-oxoacetic acid; 2-(3-(3-(4-(2-fluoro-3-methoxyphenoxy)phenyl)-7-methoxy-1H-pyrazolo[4,3-c]pyridin-1-yl)piperidin-1-yl)-2-oxoacetamide3-(3-(4-(2-fluoro-3-methoxyphenoxy) phenyl)-7-methoxy-1H-pyrazolo[4,3-c]pyridin-1-yl) cyclohexanecarboxylic acid; 4-(3-(4-(2-fluoro-3-methoxyphenoxy)phenyl)-7-methoxy-1H-pyrazolo[4,3-c] pyridin-1-yl)cyclohexanecarboxylic acid; (E)-2-(3-(3-(4-(2-fluoro-3-methoxyphenoxy)phenyl)-7-methoxy-1H-pyrazolo [4,3-c]pyridin-1-yl)piperidine-1-carbonyl)-4,4-dimethylpent-2-enenitrile; 1-(2-((3-(4-(2-fluoro-3-methoxyphenoxy) phenyl)-7-methoxy-1H-pyrazolo[4,3-c]pyridin-1-yl) methyl)pyrrolidin-1-yl)prop-2-en-1-one; (E)-2-(2-((3-(4-(2-fluoro-3-methoxyphenoxy)phenyl)-7-methoxy-1H-pyrazolo [4,3-c]pyridin-1-yl)methyl)pyrrolidine-1-carbonyl)-4,4-dimethylpent-2-enenitrile; (R)-1-(3-(7-(2-(dimethylamino) ethoxy)-3-(4-(2-fluoro-3-methoxyphenoxy)phenyl)-1H-pyrazolo[4,3-c]pyridin-1-yl)piperidin-1-yl)prop-2-en-1-one; (R)-1-(3-(7-(2-(dimethylamino)ethoxy)-3-(4-(2-fluoro-3-methoxyphenoxy)phenyl)-1H-pyrazolo[4,3-c]pyridin-1-yl)piperidin-1-yl)but-2-yn-1-one; 4-(3-(4-benzamidophenyl)-1H-pyrazolo[4,3-c]pyridin-1-yl) cyclohexanecarboxylic acid; 4-(3-([1,1'-biphenyl]-4-yl)-1H-pyrazolo[4,3-c]pyridin-1-yl)cyclohexanecarboxylic acid; (S)-1-(3-(3-(4-(1-phenoxyphenyl)-1H-pyrazolo[4,3-c]pyridin-1-yl)piperidin-1-yl)prop-2-en-1-one; 3-(3-(4-phenoxyphenyl)-1H-pyrazolo[4,3-c]pyridin-1-yl)cyclohexanecarboxylic acid; 4-(3-(4-(benzyloxy)phenyl)-1H-pyrazolo[4,3-c]pyridin-1-yl)cyclohexanecarboxylic acid.

DETAILED DESCRIPTION OF THE INVENTION

The methods described herein include administering to a subject in need a composition containing a therapeutically effective amount of one or more Btk inhibitor compounds described herein.

Prodrugs means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds.

Tautomers mean compounds produced by the phenomenon wherein a proton of one atom of a molecule shifts to another atom. Tautomers also refer to one of two or more structural isomers that exist in equilibrium and are readily converted from one isomeric form to another. One of ordinary skill in the art would recognize that other tautomeric ring atom arrangements are possible. All such isomeric forms of these compounds are expressly included in the present disclosure.

Isomers mean compounds having identical molecular formulae but differ in the nature or sequence of bonding of their atoms or in the arrangement of their atoms in space. Isomers that differ in the arrangement of their atoms in space are termed stereoisomers. Stereoisomers that are not mirror images of one another are termed diastereomers, and those that are non-superimposable mirror images of each other are termed enantiomers. When a compound has an asymmetric center, for example, it is bonded to four different groups, a pair of enantiomers is possible. A chiral compound can exist as either individual enantiomer or as a mixture thereof. Unless otherwise indicated, the description is intended to include individual stereoisomers as well as mixtures.

Certain compounds of the present disclosure can exist in unsolvated forms as well as solvated forms, including hydrated forms. Solvates refer to a complex formed by combination of solvent molecules with the compound of Formula I. The solvent can be an organic compound, an inorganic compound, or a mixture thereof.

Pharmaceutically acceptable salts represent those salts which are, within the scope of medical judgement, suitable for use in contact for the tissues of humans and lower animals without undue toxicity, irritation, allergic response and the like, and are commensurate with a reasonable benefit/risk ratio. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Therapeutically effective amount means an amount of compound or a composition of the present invention effective in inhibiting Bruton's tyrosine kinase and thus producing the desired therapeutic effect.

As used herein, the term alkyl refers to a monovalent straight or branched chain, saturated aliphatic hydrocarbon radical having a number of carbon atoms in the specified range. For example, $C_{1-6}$ alkyl refers to any of the hexyl alkyl and pentyl alkyl isomers as well as n-, iso-, sec- and t-butyl, n- and iso-propyl, ethyl and methyl. Alkyl also includes saturated aliphatic hydrocarbon radicals wherein one or more hydrogens are replaced with deuterium, for example, $CD_3$.

The term branched alkyl refers to an alkyl group as defined above except that straight chain alkyl groups in the specified range are excluded. As defined herein, branched alkyl includes alkyl groups in which the alkyl is attached to the rest of the compound via a secondary or tertiary carbon. For example, isopropyl is a branched alkyl group.

The term cycloalkyl refers to any monocyclic ring of an alkane having a number of carbon atoms in the specified range. For example, $C_{3-6}$cycloalkyl refers to cyclopropyl, cyclobutyl, cyclopentyl, and cyclohexyl.

The term halogen refers to fluorine, chlorine, bromine and iodine (alternatively referred to as fluoro, chloro, bromo, and iodo).

The term haloalkyl refers to an alkyl group as defined above in which one or more of the hydrogen atoms have been replaced with a halogen (i.e., F, Cl, Br and/or I). For example, $C_{1-6}$ haloalkyl refers to a $C_1$ to $C_6$ linear or branched alkyl group as defined above with one or more halogen substituents. The term fluoroalkyl has an analogous meaning except that the halogen substituents are restricted to fluoro. Suitable fluoroalkyls include the series $(CH_2)_{0-4}CF_3$.

The term C(O) or CO refers to carbonyl. The terms $S(O)_2$ or $SO_2$ refers to sulfonyl. The term S(O) or SO refers to sulfinyl.

The term aryl refers to phenyl, naphthyl, tetrahydronaphthyl, idenyl, dihydroindenyl and the like. An aryl of particular interest is phenyl.

The term heteroaryl refers to (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. A class of heteroaryls of interest consists of (i) 5- and 6-membered heteroaromatic rings containing from 1 to 3 heteroatoms independently selected from N, O and S, and (ii) heterobicyclic rings selected from quinolinyl, isoquinolinyl, and quinoxalinyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Synthetic methods for preparing the compounds of the present invention are illustrated in the following Schemes, Methods, and Examples. Starting materials are commercially available or may be prepared according to procedures known in the art or as described herein. The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily appreciate that known variations in the conditions and processes can be used to prepare such compounds.

Formula (I)

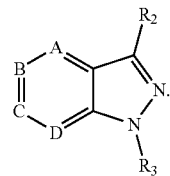

(I)

The Btk inhibitor compounds of Formula I can be prepared by methods well known in the art of organic chemistry. The starting material used for the synthesis of these compounds can be either synthesized or obtained from commercial sources, such as, but not limited to, China chemical companies or Sigma-Aldrich Chemical Co. (St. Louis, Mo.) at China. The compounds described herein, and other related compounds having different substituents are optionally synthesized using techniques and materials, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in United States Patent Application Publication No. US 2011/0130429 A1, Burgey et al. *Bioorganic & Medicinal Chemisty Letters* 10 (2006) 5052-5056. The definitions of chemistry terms used in this application may be found in these reference (if not otherwise defined herein). As a guide the following synthetic methods may be utilized.

During the synthetic sequences it may be necessary and/or desirable to protect sensitive or reactive groups on any of the molecules concerned. This is achieved by means of conventional protecting groups, such as those described in T. W Greene and P. G. M. Wutts "Protective groups in Organic Synthesis" 3rd Edition, John Wiley and Sons, 1999. The protective groups are optionally removed at a convenient subsequent stage using methods well known in the art. The products of the reactions are optionally isolated and purified. If desired, using conventional techniques, but not limited to, filtration, distillation crystallization, chromatography and the like. Such materials are optionally characterized using conventional means, including physical constant and spectra data.

Compounds described herein may possess one or more sterocenters and each center may exist in the R or S configuration. The compounds presented herein include all diasterometic, enantiomeric, and epimeric forms as well as the appropriate mixtures thereof.

The Btk inhibitor compounds of Formula I can be, for example, 1H-pyrazolo[4,3-c]pyridine derivatives. Specifically, the Btk inhibitor compounds of Formula I can be, for example, compounds F, wherein $R_1$-$R_2$ have the previously defined meanings. A non-limiting example of a synthetic approach towards the preparation of compounds F can be prepared by the general synthetic route shown in Scheme I and Scheme II.

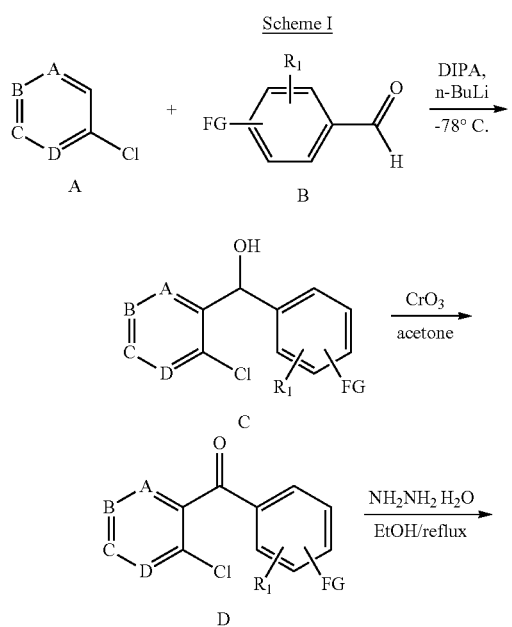

Referring to Scheme I, different aldehyde (B), in which FG is a functional group (e.g. ester, protected anilines, protected phenols, bromide), could be added to a range of substituted o-haloaromatics A to form an alcohol, followed by oxidation of the product C with $CrO_3$ in acetone to give benzoyl D. Ring closure D with $(NH_2)_2$—$H_2O$ under reflux to obtain the key intermediates indazole E. Intermediate E is coupled with $R_2OH$ via Mitsunobu reaction or with $R_2OTs$ via replacement to give the intermediate G, which then are derivatived by metal catalyst coupling reaction using appropriately substituted phenylboronic acid (corresponding boronic esters may also be used) directly affords the desired compounds F. In a typical procedure, a mixture of intermediates G, a copper catalyst (e.g. $Cu(OAc)_2$), base (e.g. TEA, DIPEA or the like) and an aryl boronic acid or aryl boronic ester in a suitable solvent such as DCM, or toluene to form compounds F (FG is converted to groups defined for XAr).

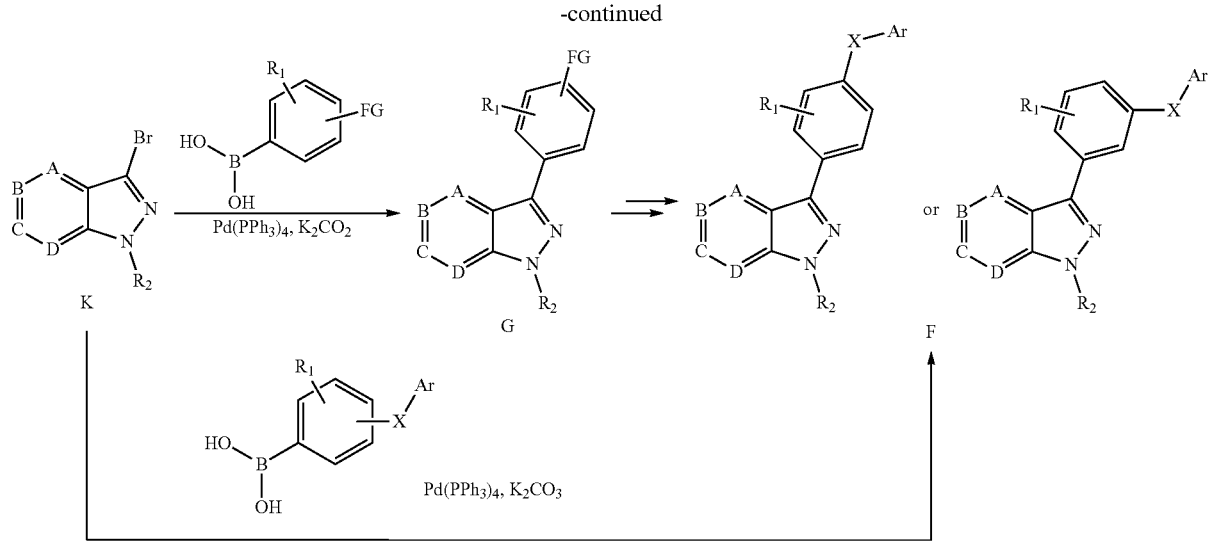

Referring to Scheme II, compounds F can be obtained from another route, selective ortho-lithiation in dry THF with LDA in situ made and later reaction with DMF to afford aldehyde H, which reacts with $(NH_2)_2$—$H_2O$ under reflux to obtain the key intermediates indazole I, then regioselective bromination or iodation with $Br_2/I_2$ or NBS/NIS to afford compound J. Coupling reaction of the 1-nitrogen on the indazole with $R_2OH$ via Mitsunobu reaction or with $R_2OTs$ via replacement to give the intermediate K, which then are derivatived by metal catalyst coupling reaction using appropriately substituted phenylboronic acid (corresponding boronic esters may also be used) affords a key intermediate G or directly affords the desired compounds F. The transformation from G to F is synthesized in a similar manner as before showed at Scheme I.

Alternatively, compound F can be obtained from compounds G, in which FG is a functional group (e.g. ester, protected anilines, protected phenols, bromide) that can be easily converted to groups defined for XAr. Non-limiting examples of suitable functional groups in compounds G are a benzyl ether, dibenzyl anime, or methyl ester, which can be treated with base or $Pd/C/H_2$ to form the key intermediates G-1a, G-2a, G-3a, then form corresponding compounds F-1, F-2, F-3, F-4 at Scheme III.

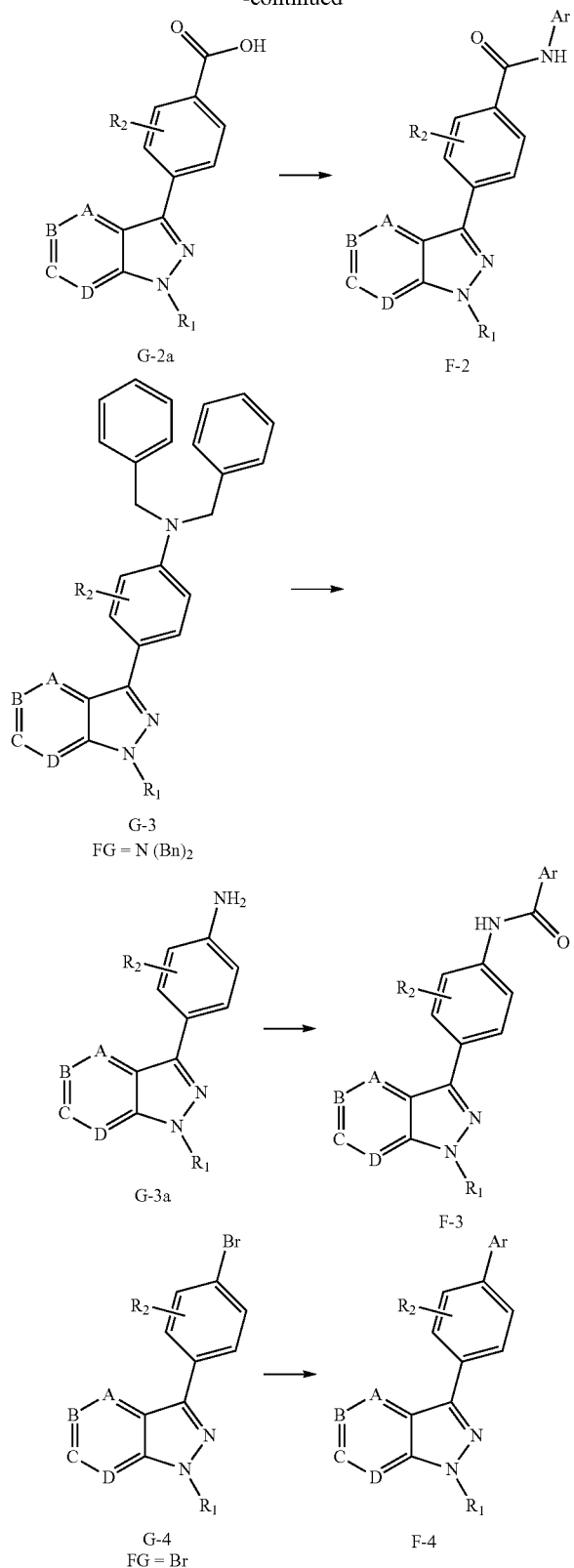

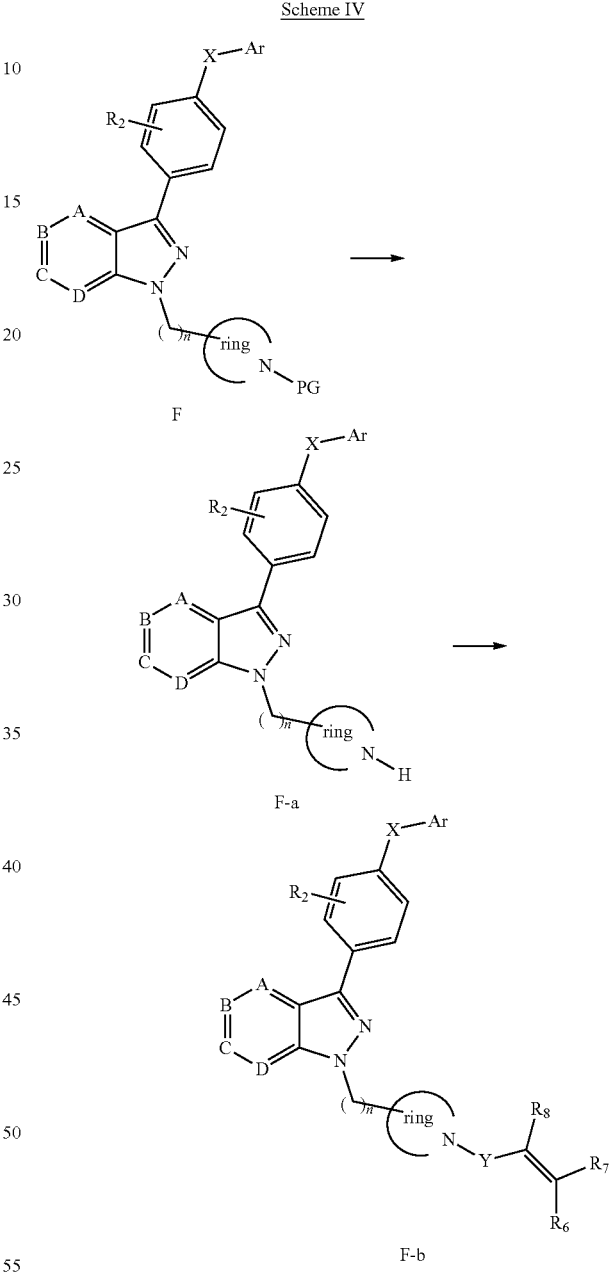

Scheme IV group and (b) deprotection reactions based on hydrogenolysis for benzyl protecting group. After deprotection with these conditions, coupling with, but not limited to, an acid chloride, such as, but not limited to, aryloyl chloride, completes the synthesis to provide compound F-b.

The deprotection reactions for the protective groups of compound F in Scheme IV are known and can be run by the methods described below. Examples here are (a) deprotection reaction under acidic conditions for Boc protecting General experimental conditions: Preparative thin layer chromatography (PTLC) was performed on 20×20 cm plates (500 micron thick silica gel). Silica gel chromatography was performed on a Biotage Horizon flash chromatography system. 1H NMR spectra were recorded on a Bruker Ascend™ 400 spectrometer at 400 MHz at 298° K, and the chemical shifts are given in parts per million (ppm) referenced to the residual proton signal of the deuterated solvents: $CDCl_3$ at δ=7.26 ppm and $CH_3OH$ or $CH_3OD$ at δ=3.30 ppm. LCMS spectra were taken on an Agilent Technologies 1260 Infinity or 6120 Quadrupole spectrometer. The mobile phase for the LC was acetontrile (A) and water (B) with 0.01% formic acid, and the eluent gradient was from 5-95% A in 6.0 min, 60-95% A in 5.0 min, 80-100% A in 5.0 min and 85-100% A in 10 min using a SBC18 50 mm×4.6 mm×2.7 μm capillary column. Mass spectra (MS) were measured by electrospray ion-mass spectroscopy (ESI). All temperatures are in degrees Celsius unless otherwise noted.

Analytical HPLC mass spectrometry conditions:
LC1: Column: SB-C18 50 mm×4.6 mm×2.7 μm
Temperature: 50° C.
Eluent: 5:95 v/v acetonitrile/water+0.01% formic acid in 6 min.
Flow Rate: 1.5 mL/min, Injection 5 μL
Detection: PDA, 200-600 nm
MS: mass range 150-750 amu; positive ion electrospray ionization
LC2: Column: SB-C18 50 mm×4.6 mm×2.7 μm
Temperature: 50° C.
Eluent: 5:95 to 95:5 v/v acetonitrile/water+0.05% TFA over 3.00 min.
Flow Rate: 1.5 mL/min, Injection 5 μL
Detection: PDA, 200-600 nm
MS: mass range 150-750 amu; positive ion electrospray ionization
LC3: Column: SB-C18 50 mm×4.6 mm×2.7 μm
Temperature: 50° C.
Eluent: 10:90 to 98:2 v/v acetonitrile/water+0.05% TFA over 3.75 min.
Flow Rate: 1.0 mL/min, Injection 10 μL
Detection: PDA, 200-600 nm
MS: mass range 150-750 amu; positive ion electrospray ionization List of Abbreviations AcOH=acetic acid; Alk=alkyl; Ar=aryl; Boc=tert-butyloxycarbonyl; bs=broad singlet; $CH_2Cl_2$=dichloromethane; d=doublet; dd=doublet of doublets; DBU=1,8-diazabicyclo[5.4.0]undec-7-ene; DCM=dichloromethane; DEAD=diethyl azodicarboxylate; DMF=N,N-dimethylformamide; DMSO=dimethyl sulfoxide; EA=ethyl acetate; ESI=electrospray ionization; Et=ethyl; EtOAc=ethyl acetate; EtOH=ethyl alcohol; h=hours; HOAc=acetic acid; LiOH=lithium hydroxide; m=multiplet; Me=methyl; MeCN=acetonitrile; MeOH=methyl alcohol; $MgSO_4$=magnesium sulfate; min=minutes; MS=mass spectroscopy; NaCl=sodium chloride; NaOH=sodium hydroxide; $Na_2SO_4$=sodium sulfate; NMR=nuclear magnetic resonance spectroscopy; PE=petroleum ether; PG=protecting group; Ph=phenyl; rt=room temperature; s=singlet; t=triplet; TFA=trifluoroacetic acid; THF=tetrahydrofuran; Ts=p-toluenesulfonyl (tosyl).

The compounds of the present invention can be prepared following general methods detailed below. In certain embodiments, provided herein are methods of making the tyrosine kinase inhibitor compounds described herein. In certain embodiments, compounds described herein are synthesized using the following synthetic schemes. In other embodiments, compounds are synthesized using methodologies analogous to those described below by the use of appropriate alterative starting materials. All key intermediates were prepared according to the following methods.

Intermediate 1:
(4-(2-chloro-3-methoxyphenoxy)phenyl) boronic acid

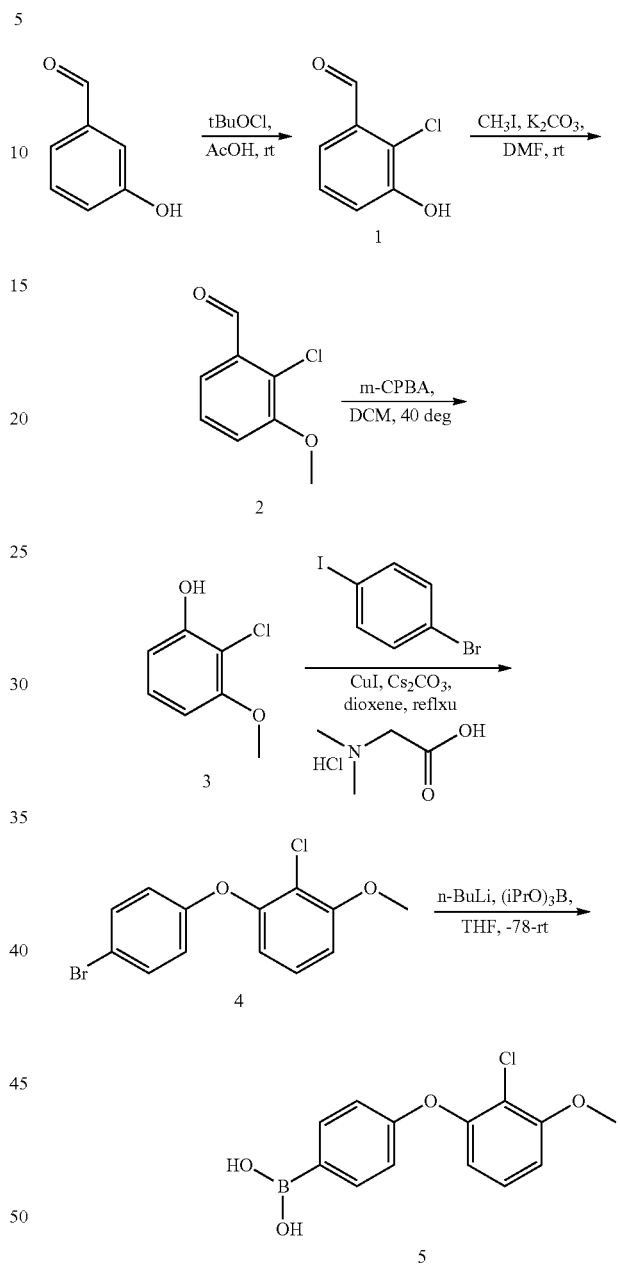

Step A: 2-chloro-3-hydroxybenzaldehyde (1)

To a suspension of 3-hydroxybenzaldehyde (5 g, 40.98 mmol) in AcOH (10 mL) was added carefully t-BuOCl (5 mL, 45.08 mmol) with stirring. It was allowed to cool and stirred for 16 hours, resulting in a white precipitate. The solid was filtered, washed with $H_2O$ and dried to give the title product (3 g, 46.9%). $^1$H-NMR (400 MHz, $CDCl_3$): δ 10.66 (br, 1H), 10.33 (s, 1H), 7.31-7.25 (m, 3H).

Step B: 2-chloro-3-hydroxybenzaldehyde (2)

To a solution of 2-chloro-3-hydroxybenzaldehyde 1 (3.4 g, 21.66 mmol) in DMF (22 mL) was added $K_2CO_3$ (3.59 g, 26 mmol) followed by MeI (2 mL, 32.5 mmol), and the mixture was stirred at room temperature for 18 hours. Following concentration in vacuum, the residue was taken up in ethyl acetate, washed with H₂O, brine, dried over Na₂SO₄, and concentrated. Purification by column chromatography on silica gel with ethyl acetate/hexanes 1/5 afforded the title product (3.5 g, 95.1%). ¹H-NMR (400 MHz, CDCl₃): δ 10.53 (s, 1H), 7.53 (d, J=7.6 Hz, 1H), 7.36-7.32 (m, 1H), 7.01 (d, J=8.8 Hz, 1H), 3.95 (s, 3H).

Step C: 2-chloro-3-hydroxybenzaldehyde (3)

To a solution of 2-Chloro-3-Methoxybenzaldehyde 2 (2 g, 11.7 mmol) in DCM (50 ml) was added 3-Chloroperoxybenzoic acid (3 g, 17.5 mmol). The mixture was stirred for 12 hours at 40° C. Filtered, the residue was contracted to a soled. The soled was desalted in 18 mL of MeOH, then 5 mL of 10% NaOH was added with cooling. After stirring for 45 min at 10° C., the mixture was condition at 30° C. on a rotary evaporator to remove the MeOH, then 22 mL of 5% NaOH, was added and the solution was added with Conc HCl with cooling, then extracted (3×20) with EA, wished with H₂O, 5% NaHCO₃, dried over Na₂SO₄ and concentrated in vacuo to afford the title compound (1.2 g, 66.6%). ¹H-NMR (400 MHz, CDCl₃): δ 7.14-7.10 (m, 1H), 6.67 (d, J=8.4 Hz, 1H), 6.51 (d, J=8.4 Hz, 1H), 5.62 (s, 1H), 3.89 (s, 3H).

Step D: 1-(4-bromophenoxy)-2-chloro-3-methoxybenzene (4)

To a solution of 1-bromo-4-iodobenzene (2.68 g, 9.5 mmol) in dioxene (40 mL) was added 3 (1.5 g, 9.5 mmol), CuI (0.182 g, 0.95 mmol), N,N-Dimethylglycine hydrochloride (0.396 g, 2.85 mmol), Cs₂CO₃ (6.2 g, 19 mmol). The mixture was stirred at 105° C. in N₂ for 18 h. The mixture was Filtered, contracted and extracted with EA, The organic layer was washed with water and brine, dried with anhydrous Na₂SO₄, and purified by flash chromatography to give the title product (1.2 g, 40.4%). ¹H-NMR (400 MHz, CDCl₃): δ 7.43-7.39 (m, 2H), 7.18-7.15 (m, 1H), 6.85-6.75 (m, 3H), 6.65-6.15 (m, 1H), 3.93 (s, 3H).

Step E: 1-(4-bromophenoxy)-2-chloro-3-methoxybenzene (5)

To a solution of 4 (1.2 g, 3.85 mmol) in THF (30 mL) was cooled to −78° C. under N₂, n-BuLi (1.82 mL, 4.61 mmol), was added dropwise under same temperature. The mixture was stirred for 30 min at same temperature. Triisopropyl borate (0.868 g, 4.61 mmol), was added dropwise under same temperature. After 15 min, the mixture was allowed to room temperature and stirred for 2 h, then 2 N HCl was added to adjust to pH=5 and stirred for 30 min, then the mixture was The mixture was extracted with EA, The organic layer was washed with water and brine, dried with anhydrous Na₂SO₄, give the title crude product (0.4 g crude).

Example 1: (R)-1-(3-(3-(4-phenoxyphenyl)-1H-pyrazolo[4,3-c]pyridin-1-yl)pyrrolidin-1-yl)prop-2-en-1-one

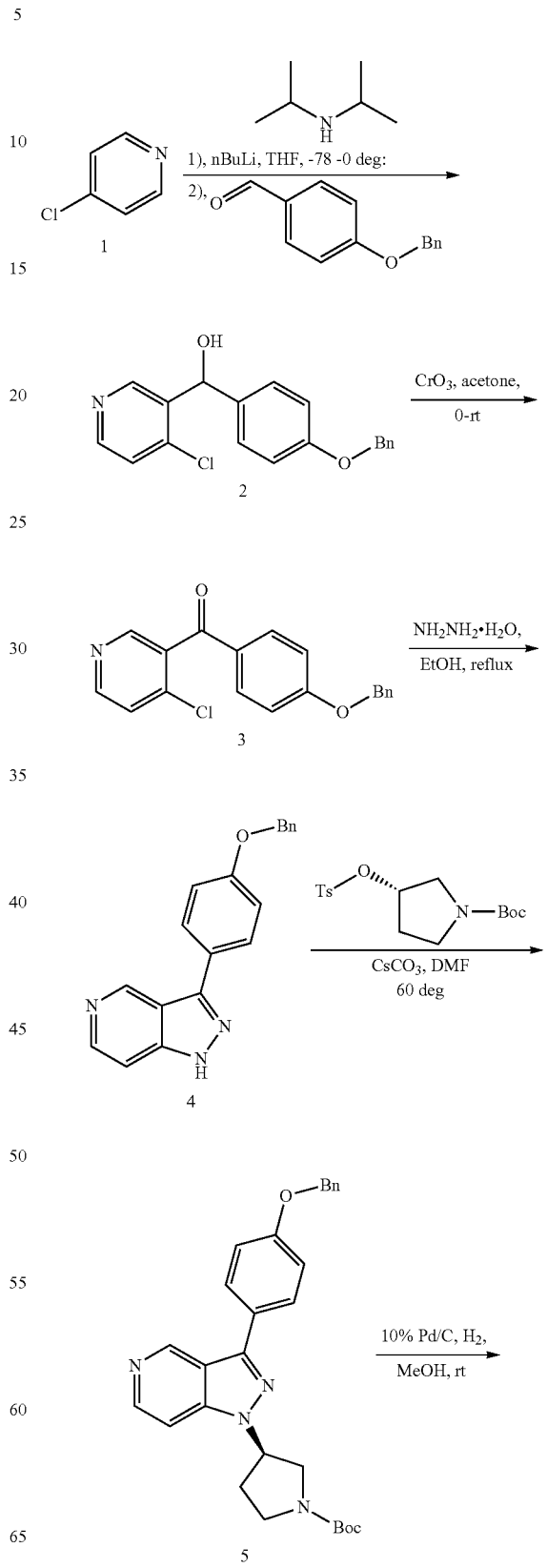

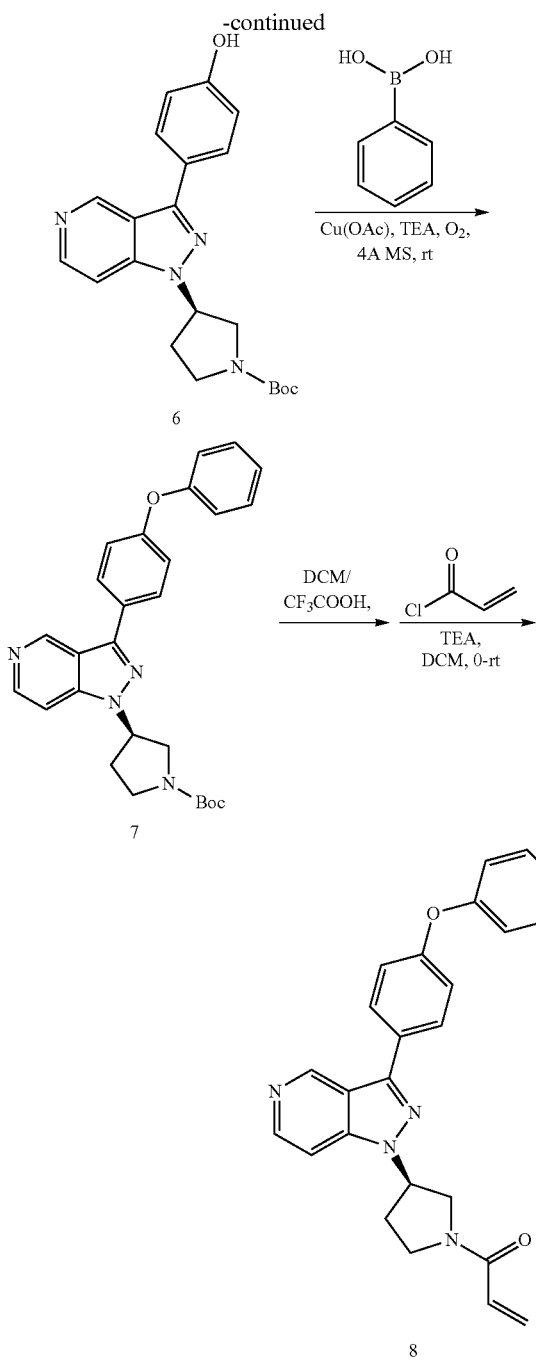

Step A: (4-(benzyloxy)phenyl)(4-chloropyridin-3-yl)methanol (2)

To a solution of diisopropylamine (4.1 mL, 29.8 mmol) in dry THF (64 mL) at −78° C. was added a 2.5M BuLi solution in hexane (15 mL, 29.8 mmol). The mixture was allowed to warm to 0° C. and stirred about 1 h, then the solution was cooled to −78° C. and 4-chloropyridine (3.07 g, 27.1 mmol) in 10 mL of dry THF was added. The reaction mixture was stirred for additional 4 h, and then the corresponding 4-(benzyloxy)benzaldehyde (5.75 g, 27.1 mmol) was added and the mixture was stirred and allowed to warm to room temperature overnight. The reaction was quenched with H$_2$O (25 mL), and the mixture was extracted with Et$_2$O (3×50 mL). The organic phases were combined, dried over Na$_2$SO$_4$, Volatile components were removed under vacuum and the residue was purified by column chromatography on silica gel (gradient: DCM/MeOH=200:1-50/1) to give the title product (2.5 g, yield 28.46%). $^1$H-NMR (400 MHz, CDCl$_3$): δ 8.86 (s, 1H), 8.36 (d, J=4.0 Hz, 1H), 7.39-7.23 (m, 8H), 6.94 (d, J=8.0 Hz, 2H), 6.12 (s, 1H), 5.03 (s, 2H), 2.98 (s, 1H), 2.16 (s, 1H). LCMS: m/z=326, 328 [M+H]$^+$.

Step B: (4-(benzyloxy) phenyl)(4-chloropyridin-3-yl)methanone (3)

A solution of (4-(benzyloxy)phenyl)(4-chloropyridin-3-yl)methanol (2) (1 g, 3.07 mmol) in dry acetone (10 mL) was cooled to 0° C. and CrO$_3$ (0.92 g, 9.23 mmol) was added carefully in small portions. The resulting solution was stirred at room temperature until complete consumption of the starting material (3 h), then reaction was quenched with 2-propanol (6 mL), and the mixture was stirred 30 min. A saturated solution of NaHCO$_3$ (50 mL) was finally added to precipitate the chromium salts that were filtered over celite and washed with CH$_2$Cl$_2$ (6×15 mL). The solvent were removed under vacuum and the residue was purified by column chromatography on silica gel (gradient: DCM/MeOH=200:1), to give the title product (0.7 g, yield 70.7%). $^1$H-NMR (400 MHz, CDCl$_3$): δ 8.61 (d, J=8.0 Hz, 1H), 8.58 (S, 1H), 7.79 (d, J=8.0 Hz, 2H), 7.44-7.35 (m, 6H), 7.04 (d, J=8.0 Hz, 2H), 5.15 (s, 2H). LCMS: m/z=324, 326 [M+H]$^+$.

Step C: 3-(4-(benzyloxy)phenyl)-1H-pyrazolo[4,3-c]pyridine (4)

To a stirred solution (4-(benzyloxy)phenyl)(4-chloropyridin-3-yl)methanone (3) (0.7 g, 2.16 mol) in absolute ethanol (5 ml) was added hydrazine (1.08 g, 17.3 mol). The solution was heated under reflux for 3 h, then cooled and the product filtered off and washed consecutively with water and methanol to give the title product (0.54 g, yield 83%). $^1$H-NMR (400 MHz, DMSO-d6): δ 13.48 (br, 1H), 9.39 (s, 1H), 8.37 (d, J=8.0 Hz, 1H), 8.01 (d, J=8.0 Hz, 2H), 7.56-7.35 (m, 6H), 7.18 (d, J=8.0 Hz, 2H), 5.20 (S, 2H). LCMS: m/z=302 [M+H]$^+$.

Step D: (R)-tert-butyl-3-(3-(4-(benzyloxy)phenyl)-1H-pyrazolo[4,3-c]pyridin-1-yl)pyrrolidine-1-carboxylate (5)

Into a 100 mL 3-necked round-bottom flask, was placed a solution of 3-(4-(benzyloxy)phenyl)-1H-pyrazolo[4,3-c]pyridine (4) (0.5 g, 1.66 mmol) in N,N-dimethylformamide (41 mL), (S)-tert-butyl-3-(tosyloxy)pyrrolidine-1-carboxylate (0.68 g, 1.99 mmol), and Cs$_2$CO$_3$ (0.97 g, 2.98 mmol). The resulting solution was stirred for 12 h at 60° C. and then quenched by the addition of 100 mL of water. The resulting solution was extracted with EA and the organic layers combined. The organics were washed with brine, dried over anhydrous NaHCO$_3$, The solvent were removed under vacuum and the residue was purified by column chromatography on silica gel (gradient: DCM/MeOH=200:1-100:1) to give the title product (0.7 g, yield 89.7%). $^1$H-NMR (400 MHz, CDCl$_3$): δ 9.32 (br, 1H), 8.45 (br, 1H), 7.85-7.83 (m, 2H), 7.37-7.36 (m, 1H), 7.04-7.02 (m, 2H), 5.18-5.15 (m, 1H), 3.96-3.79 (m, 3H), 3.63-3.59 (m, 1H), 2.89 (br, 1H), 2.45 (br, 1H), 1.47 (s, 9H). LCMS: m/z=471 [M+H]$^+$.

Step E: (R)-tert-butyl-3-(3-(4-hydroxyphenyl)-1H-pyrazolo[4,3-c]pyridin-1-yl)pyrrolidine-1-carboxylate (6)

A suspension of (R)-tert-butyl 3-(3-(4-(benzyloxy)phenyl)-1H-pyrazolo[4,3-c]pyridin-1-yl)pyrrolidine-1-carboxylate (5) (0.7 g, 1.48 mmol) and 10% Pd/C (0.1 g) in MeOH (15 mL) was hydrogenated at 50 psi $H_2$ for 3 h. The suspension was filtered through Celite and concentrated. The residue was dried in vacuo to give the title product (0.48 g, yield 85.7%). LCMS: m/z=381 [M+H]$^+$.

Step F: (R)-tert-butyl 3-(3-(4-phenoxyphenyl)-1H-pyrazolo[4,3-c]pyridin-1-yl)-pyrrolidine-1-carboxylate (7)

(R)-tert-butyl-3-(3-(4-hydroxyphenyl)-1H-pyrazolo[4,3-c]pyridin-1-yl)pyrrolidine-1-carboxylate (6) (50 mg, 0.1 mmol), phenylboronic acid (25.4 mg, 0.2 mmol), TEA (21 mg, 0.2 mmol) and 4 A molecular sieves (0.1 g) were added to DCM (10 mL) in a vial Copper (II) acetate (18.8 mg, 0.1 mmol) was added in one portion. The mixture was stirred for about 22 h at room temperature. Volatile components were removed under vacuum, before being poured into $H_2O$. The reaction mixture was extracted with EA, organic phase was purified by column chromatography on silica gel (gradient: DCM/MeOH=100/1-50/1) to give the title product (40 mg, yield 88.8%). LCMS: m/z=457 [M+H]$^+$.

Step G: (R)-1-(3-(3-(4-phenoxyphenyl)-1H-pyrazolo[4,3-c]pyridin-1-yl)pyrrolidin-1-yl)prop-2-en-1-one (8)

(R)-tert-butyl 3-(3-(4-phenoxyphenyl)-1H-pyrazolo[4,3-c]pyridin-1-yl)-pyrrolidine-1-carboxylate (7) (40 mg, 0.087 mmol) were added to $CF_3COOH/DCM=4/1$ (5 mL) in one portion. The mixture was stirred for about 1 h at rt. Volatile components were removed under vacuum to give the title product of crude product (30 mg), and directly used in next step without further purification. LCMS: m/z=357 [M+H]$^+$.

To a solution of Acryloyl chloride (8.7 mg, 0.095 mmol) in DCM (1 mL) was added to a stirred solution of (R)-3-(4-phenoxyphenyl)-1-(pyrrolidin-3-yl)-1H-pyrazolo[4,3-c]pyridine (8) (30 mg, 0.087 mmol) and TEA (44 mg, 0.43 mmol) in DCM (5 mL) at 0° C. The reaction mixture was stirred for 1 h, poured onto brine and extracted with DCM. The organic layer was dried, concentrated and recrystallized from DCM/MeOH=100/1 to give the title product (16 mg, yield 45.7%). $^1$H-NMR (400 MHz, CDCl$_3$): δ 9.35 (br, 1H), 8.49 (br, 1H), 7.95-7.91 (m, 2H), 7.40-7.36 (m, 3H), 7.15-7.08 (m, 5H), 6.53-6.42 (m, 2H), 5.76-5.71 (m, 1H), 5.27-5.15 (m, 1H), 4.17-4.03 (m, 3H), 3.85-3.82 (m, 1H), 2.79-2.49 (m, 2H). LCMS: m/z=411.2 [M+H]$^+$.

Example 2: (R)-1-(3-(3-(4-(2-chloro-3-methoxyphenoxy)phenyl)-1H-pyrazolo[4,3-c]pyridin-1-yl)piperidin-1-yl)prop-2-en-1-one

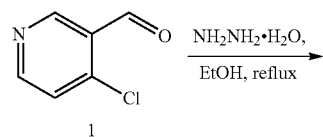

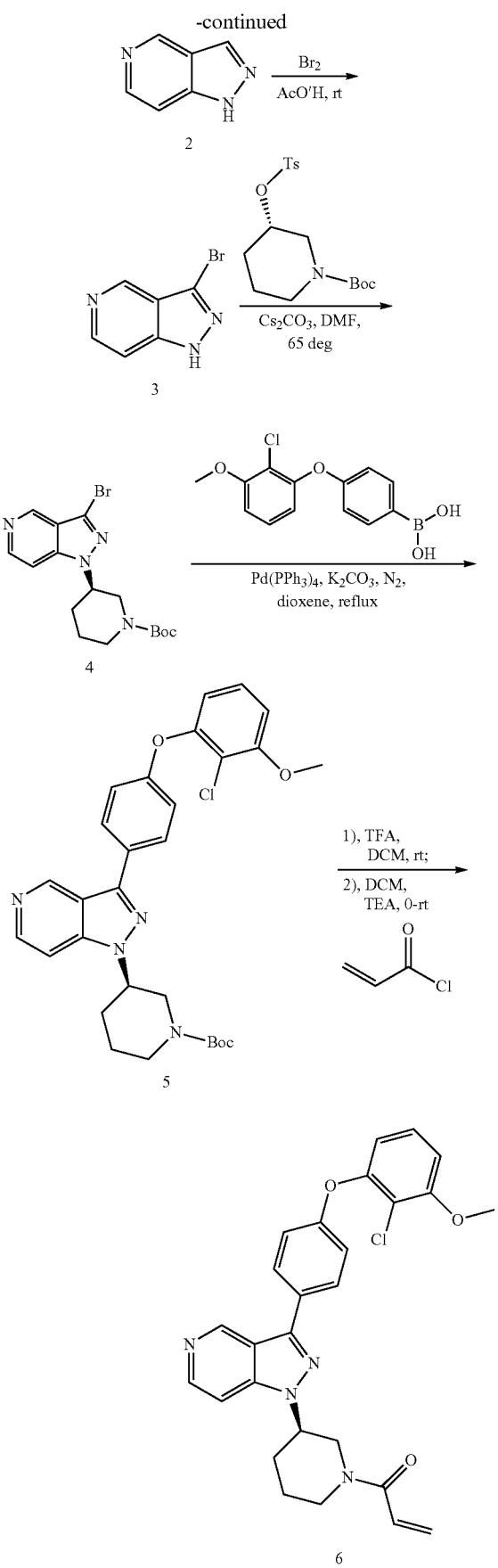

Step A: 1H-pyrazolo[4,3-c]pyridine (2)

To a stirred solution 1H-pyrazolo[4,3-c]pyridine (1) (17 g, 0.12 mol) in absolute ethanol (120 ml) was added hydrazine (80%) (75 g, 1.2 mol). The solution was heated under reflux for 5 h, EtOH was removed under vacuum, and the mixture was extracted with EA (10×100 mL), The organic phases were combined, dried over $Na_2SO_4$. Volatile components were removed under vacuum and the residue was purified by column chromatography on silica gel (gradient: DCM/MeOH=200:1-50/1) to give the title product (8 g, yield 57.1%). $^1$H-NMR (400 MHz, $CDCl_3$): δ 3.48 (br, 1H), 9.18 (s, 1H), 8.44 (d, J=6.0 Hz, 1H), 8.25 (s, 1H), 7.45 (d, J=6.0 Hz, 1H). LCMS: m/z=120 [M+H]$^+$.

Step B: 3-bromo-1H-pyrazolo[4,3-c]pyridine (3)

To a solution of 1H-pyrazolo[4,3-c]pyridine (2) (8 g, 67.2 mmol) in AcOH (100.0 mL), was added bromine (5.1 mL, 0.1 mol) at room temperature. The reaction was stirred at room temperature for 72 h and quenched with 10% NaOH (aq.) to pH 12. The organics were separated. The aqueous layer was extracted again with EA (10×100 mL). The organic phases were combined, dried over $Na_2SO_4$, volatile components were removed under vacuum and the residue was purified by column chromatography on silica gel (gradient: DCM/MeOH=200:1-50/1) to give the title product (4.5 g, yield. 34.3%). $^1$H-NMR (400 MHz, $CDCl_3$): δ 3.32 (br, 1H), 9.06 (s, 1H), 8.54 (d, J=5.6 Hz, 1H), 7.43 (d, J=5.6 Hz, 1H). LCMS: m/z=198, 200 [M+H]$^+$

Step D: (R)-tert-butyl3-(3-bromo-1H-pyrazolo[4,3-c]pyridin-1-yl)piperidine-1-carboxylate (4)

Into a 100 mL round-bottom flask, was placed a solution of 3-bromo-1H-pyrazolo[4,3-c]pyridine (3) (2 g, 10 mmol) in DMF (20 mL), (S)-tert-butyl 3-(tosyloxy)piperidine-1-carboxylate (4.3 g, 12 mmol), and $Cs_2CO_3$ (5.9 g, 18 mmol). The resulting solution was stirred for 24 h at 65° C. and then quenched by the addition of 100 mL of water. The resulting solution was extracted with EA and the organic layers combined. The organics were washed with brine, dried over anhydrous $NaHCO_3$, The solvent were removed under vacuum and the residue was purified by column chromatography on silica gel (gradient: DCM/MeOH=200:1-100.1) to give the title product (0.8 g, yield 21.0%). $^1$H-NMR (400 MHz, $CDCl_3$): δ 8.97 (s, 1H), 8.48 (d, J=5.6 Hz, 1H), 7.36 (d, J=5.6 Hz, 1H), 4.43-4.38 (m, 3H), 3.2 (br, 1H), 2.88-2.81 (m, 1H), 2.30-2.17 (m, 2H), 1.95-1.91 (m, 1H), 1.72-1.62 (m, 1H), 1.46 (s, 9H). LCMS: m/z=382 [M+H]$^+$.

Step E: (R)-tert-butyl-3-(3-(4-(2-chloro-3-methoxyphenoxy)phenyl)-1H-pyrazolo[4,3-c]pyridin-1-yl) piperidine-1-carboxylate (5)

To a solution of 4 (100 mg, 0.262 mmol) and (4-(2-chloro-3-methoxyphenoxy) phenyl) boronic acid (109.9 mg, 0.393 mmol) in toluene (5 mL) and water (1 mL) was added $K_2CO_3$ (72 mg, 0.524 mmol) followed by $(Ph_3P)_4Pd$ (30 mg) under $N_2$ with stirring. The mixture was refluxed for 8 h until the material was disappeared. The reaction mixture was cooled to room temperature. The dioxane was removed by rotary evaporation. The residue was poured into water and extracted with EA. The organic layer was dried over $Na_2SO_4$, filtered and the solvent was removed under vacuum, the residue was purified by flash chromatography on silica gel using 100:1-50:1 DCM:MeOH, give the title product (50 mg). LCMS: m/z=534.2 [M+H]$^+$

Step F: (R)-1-(3-(3-(4-(2-chloro-3-methoxyphenoxy)phenyl)-1H-pyrazolo[4,3-c]pyridin-1-yl)piperidin-1-yl)prop-2-en-1-one (6)

Intermediate 5 (50 mg, 0.093 mmol) were added to $CF_3COOH/DCM$=4/1 (5 mL) in one portion. The mixture was stirred for about 2 h at rt. Volatile components were removed under vacuum to give the title crude product, and directly used in next step without further purification. A solution of Acryloyl chloride (8.5 mg, 0.095 mmol) in DCM (1 mL) was added to a stirred solution of crude residue, TEA (44 mg, 0.43 mmol) in DCM (5 mL) at 0° C. The reaction mixture was stirred for 1 h, poured into brine and extracted with DCM. The organic layer was dried, concentrated and recrystallized from DCM/MeOH=100/1 to give the title product (29 mg, yield 65%). $^1$H-NMR (400 MHz, $CDCl_3$): δ 9.35 (s, 1H), 8.45 (d, J=5.6 Hz, 1H), 7.93 (d, J=8.4 Hz, 2H), 7.45-7.34 (m, 1H), 7.24-7.20 (m, 2H), 7.11 (d, J=8.4 Hz, 2H), 6.80 (d, J=8.4 Hz, 1H), 6.73 (d, J=8.4 Hz, 2H), 26.68-6.53 (m, 1H), 6.38-6.34 (m, 1H), 5.77-5.69 (m, 1H), 4.94-4.91 (m, 0.5H), 4.72-4.48 (br, 1.4H), 4.25-4.07 (m, 1H), 3.96 (s, 3H), 3.80-3.3.78 (m, 0.6H), 3.24-3.22 (m, 1H), 2.91 (br, 0.4H), 2.50-2.47 (m, 1H), 2.30-2.28 (m, 1H), 2.06-2.02 (m, 1H), 1.73-1.71 (m, 1H). LCMS: m/z=489.2 [M+H]$^+$.

Example 3: (R)-1-(3-(3-(4-(2-fluoro-3-methoxyphenoxy)phenyl)-1H-pyrazolo[4,3-c]pyridin-1-yl)pyrrolidin-1-yl)prop-2-en-1-one

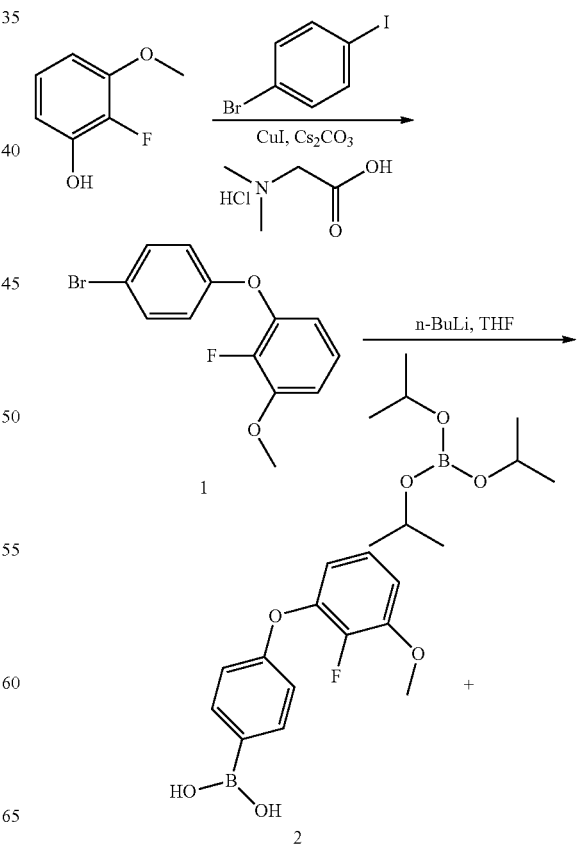

-continued

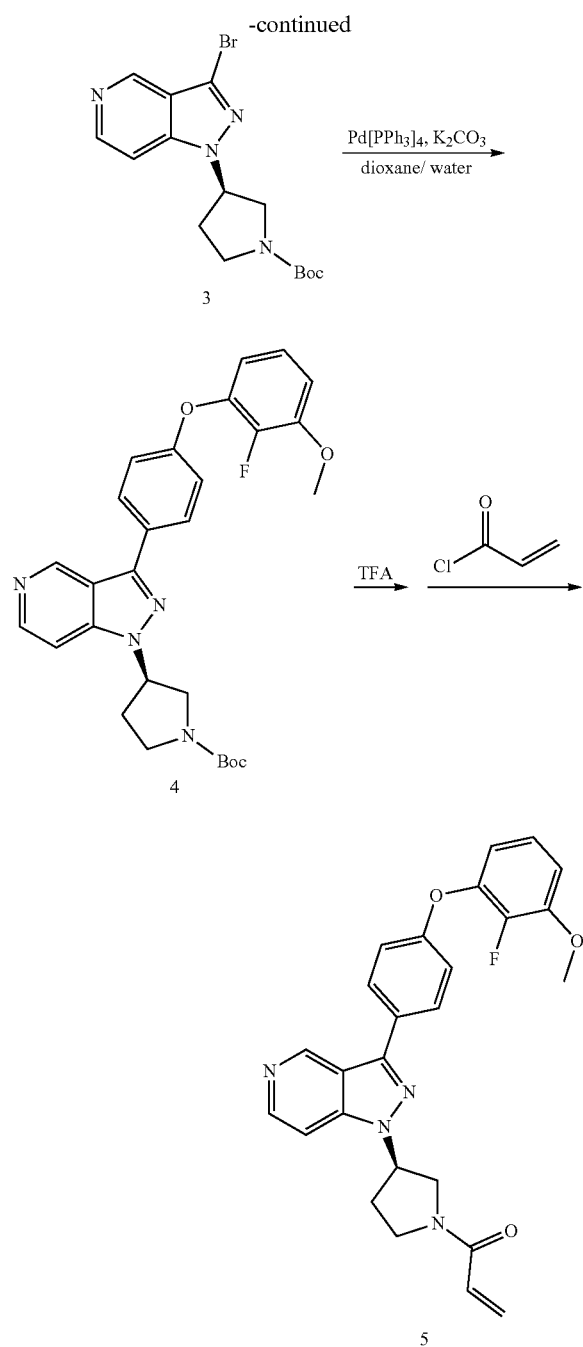

Step A: 1-(4-bromophenoxy)-2-fluoro-3-methoxybenzene (1)

To a solution of 1-bromo-4-iodobenzene (20.7 g, 73 mmol, 1.0 eq) in dioxene (180 mL) was added 2-fluoro-3-methoxyphenol (10.4 g, 73 mmol, 1.0 eq), CuI (1.39 g, 7.3 mmol, 0.1 eq), N,N-Dimethylglycine hydrochloride (2.03 g, 14.6 mmol, 0.2 eq), $Cs_2CO_3$ (35.9 g, 109.5 mmol, 1.5 eq). The mixture was stirred at 100° C. in $N_2$ for 15 h, then mixture was Filtered, contracted and extracted with EA, the organic layer was washed with water and brine, dried with anhydrous $Na_2SO_4$, concentrated and the residue was purified by silica gel column chromatography to give the title product 1 (9.2 g, 42.4%). $^1$H-NMR (400 MHz, $CDCl_3$): δ 7.59 (d, J=7.6 Hz, 1H), 7.41 (d, J=8.0 Hz, 1H), 7.00-7.04 (m, 1H), 6.87 (d, J=8.0 Hz, 1H), 6.74-6.81 (m, 2H), 6.62-6.66 (m, 1H), 3.92 (s, 3H).

Step B: (4-(2-fluoro-3-methoxyphenoxy)phenyl)boronic acid

To a solution of 1 (9.2 g, 30.96 mmol, 1.0 eq) in THF (100 mL) was cooled to −78° C. under $N_2$, n-BuLi (16.1 mL, 40.25 mmol, 1.3 eq), was added dropwise under same temperature. The mixture was stirred for 50 min at same temperature. Triisopropyl borate (7.57 g, 40.25 mmol, 1.3 eq), was added dropwise under same temperature. After 15 min, the mixture was allowed to room temperature and stirred for 2 h, then 1 N HCl was added to adjust to pH=5.0 and stirred for 30 min, then the mixture was extracted with EA, The organic layer was washed with water and brine, dried with anhydrous $Na_2SO_4$, filtered and concentrated give the title crude product 2 (7.8 g, 95.8%).

Step C: (R)-tert-butyl 3-(3-bromo-1H-pyrazolo[4,3-c]pyridin-1-yl)pyrrolidine-1-carboxylate (3)

Into a 100 mL round-bottom flask, was placed a solution of 3-bromo-1H-pyrazolo[4,3-c]pyridine (2.45 g, 23.34 mmol, 1.0 eq) in DMF (40 mL), (S)-tert-butyl 3-(tosyloxy)piperidine-1-carboxylate (5.06 g, 14.48 mmol, 1.2 eq), and $Cs_2CO_3$ (6.1 g, 18.55 mmol, 1.5 eq). The resulting solution was stirred for 12 h at 65° C. and then quenched by the addition of 100 mL of water. The resulting solution was extracted with EA (80 mL*3) and the organic layers combined. The organics were washed with brine, dried over anhydrous $Na_2CO_3$, The solvent were removed under vacuum and the residue was purified by silica gel column chromatography (DCM/MeOH=200:1-100:1) to give the title product (3.5 g, yield 76.9%). $^1$H-NMR (400 MHz, $CDCl_3$): δ 8.98 (s, 1H), 8.50 (d, J=4.8 Hz, 1H), 7.32 (d, J=5.6 Hz, 1H), 3.91 (s, 1H), 3.76-3.80 (m, 2H), 3.53-3.59 (m, 1H), 2.59 (s, 1H), 2.38-2.44 (m, 1H), 1.48 (s, 9H). LCMS: m/z=367 [M+H]$^+$.

Step D: (R)-tert-butyl 3-(3-(4-(2-fluoro-3-methoxyphenoxy)phenyl)-1H-pyrazolo[4,3-c]pyridin-1-yl)pyrrolidine-1-carboxylate (4)

To a solution of 3 (430 mg, 1.17 mmol, 1.0 eq) and 2 (460 mg, 1.76 mmol, 1.5 eq) in dioxane (20 mL) and water (3 mL) was added $K_2CO_3$ (324 mg, 2.34 mmol, 2.0 eq) and $(Ph_3P)_4Pd$ (30 mg) under $N_2$ with stirring. The mixture was refluxed for 6 h until the material was disappeared. The reaction mixture was cooled to room temperature. The dioxane was removed by rotary evaporation. The residue was poured into water and extracted with EA. The organic layer was dried over $Na_2SO_4$, filtered and the solvent was removed by rotary evaporation. The residue was purified with flash silica gel chromatography (DCM:MeOH=100:1-50:1) to give the title product (0.5 g, yield 84.4%). $^1$H-NMR (400 MHz, $CDCl_3$): δ 9.33 (s, 1H), 8.46 (d, J=5.2 Hz, 1H), 7.94 (d, J=8.4 Hz, 2H), 7.34 (d, J=5.6 Hz, 1H), 7.14 (d, J=8.8 Hz, 2H), 7.03-7.08 (m, 1H), 6.80-6.84 (m, 1H), 6.71-6.75 (m, 1H), 5.18 (s, 1H), 3.94 (s, 6H), 3.59 (s, 1H), 2.64 (s, 1H), 2.41-2.46 (m, 1H), 1.47 (s, 9H). LCMS: m/z=505 [M+H]$^+$.

Step E: (R)-1-(3-(3-(4-(2-fluoro-3-methoxyphenoxy)phenyl)-1H-pyrazolo[4,3-c]pyridin-1-yl)pyrrolidin-1-yl)prop-2-en-1-one (5)

Intermediate 4 (870 mg, 1.73 mmol, 1.0 eq) were dissolved in DCM (30 mL), added TFA (2.5 mL) in one portion. The mixture was stirred for about 1.5 h at rt. Volatile components were removed under vacuum to give the title product of crude product, and directly used in next step without further purification. The crude product was dissolved in DCM (20 mL), added TEA to the solution until PH=8.0, then added Acryloyl chloride (187 mg, 2.07 mmol, 1.2 eq) in DCM (3.0 mL) dropwise to the solution. The reaction mixture was stirred for 0.5 h, poured onto water and extracted with DCM. The organic layer was dried with anhydrous $Na_2SO_4$, filtered and concentrated, the residue was purified by silica gel column chromatography (DCM/MeOH=200:1-50:1) to give the title product (400 mg, yield 50.6%). $^1$H-NMR (400 MHz, $CDCl_3$): δ 9.34 (d, J=4.4 Hz, 1H), 8.47-8.49 (m, 1H), 7.90-7.94 (m, 2H), 7.34 (d, J=4.8 Hz, 1H), 7.12-7.14 (m, 2H), 7.03-7.07 (m, 1H), 6.80-6.84 (m, 1H), 6.71-6.75 (m, 1H), 6.40-6.52 (m, 2H), 5.69-5.75 (m, 1H), 5.20-5.23 (m, 1H), 4.06-4.17 (m, 3H), 3.94 (s, 3H), 3.81-3.85 (m, 1H), 2.47-2.78 (m, 2H). LCMS: m/z=459.1 [M+H]$^+$.

Example 4: (R)-1-(3-(3-(4-(2-chloro-3-fluorophenoxy)phenyl)-1H-pyrazolo[4,3-c]pyridin-1-yl)pyrrolidin-1-yl)prop-2-en-1-one

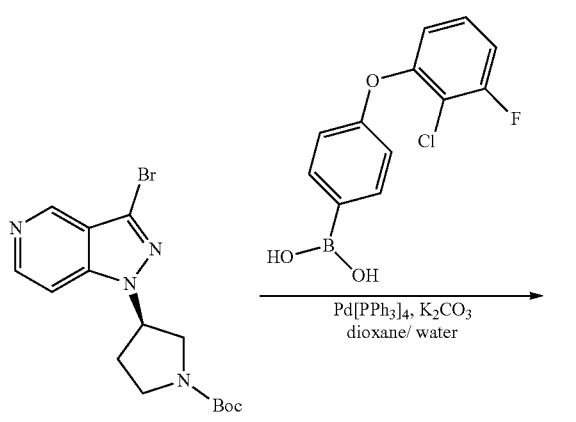

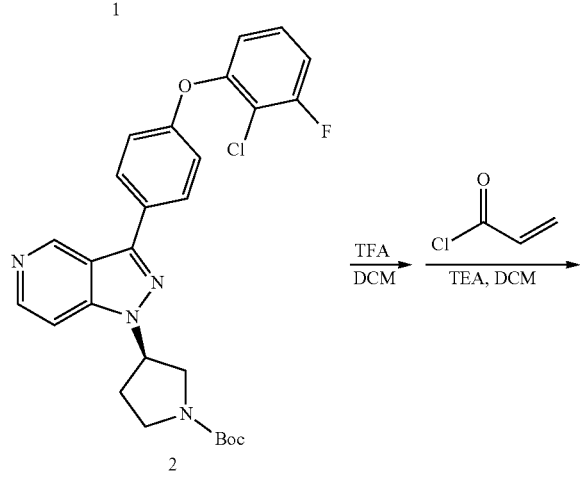

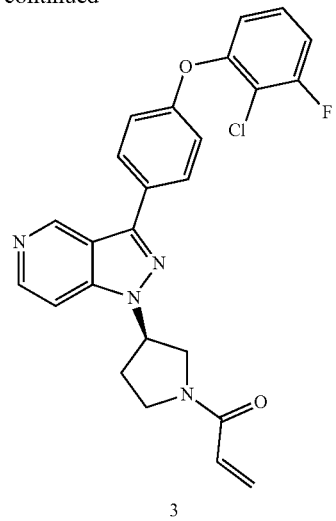

Step A: tert-butyl(R)-3-(3-(4-(2-chloro-3-fluorophenoxy)phenyl)-1H-pyrazolo[4,3-c]pyridin-1-yl)pyrrolidine-1-carboxylate (2)

To a solution of 1 (80 mg, 0.22 mmol, 1.0 eq) and corresponding boronic acid (88 mg, 0.33 mmol, 1.5 eq) in toluene (10 mL) and water (2 mL) was added $K_2CO_3$ (61 mg, 0.44 mmol, 2.0 eq) and $(Ph_3P)_4Pd$ (25 mg, 0.1 eq) under $N_2$ with stirring. The mixture was refluxed for 6 h until the material was disappeared. The reaction mixture was cooled to room temperature. The toluene was removed by rotary evaporation. The residue was poured into water and extracted with EA. The organic layer was dried over $Na_2SO_4$, filtered and the solvent was removed by rotary evaporation. The product was purified with flash silica gel chromatography (DCM:MeOH=100:1-50:1), give the title product (90 mg, yield 81%). LCMS: m/z=509 [M+H]$^+$.

Step B: (R)-1-(3-(3-(4-(2-chloro-3-fluorophenoxy)phenyl)-1H-pyrazolo[4,3-c]pyridin-1-yl)pyrrolidin-1-yl)prop-2-en-1-one Intermediate 2 (90 mg, 0.18 mmol, 1.0 eq) were dissolved in DCM (4 mL), added TFA (1 mL) in one portion. The mixture was stirred for about 1.5 h at rt. Volatile components were removed under vacuum to give the title product of crude product which was directly used in next step without further purification. The crude product was dissolved in DCM (4 mL), added TEA to the solution until PH=8.0, then added Acryloyl chloride (16 mg, 0.18 mmol, 1.0 eq) in DCM (1.0 mL) dropwise to the solution. The reaction mixture was stirred for 0.5 h, poured onto water and extracted with DCM. The organic layer was dried with anhydrous $Na_2SO_4$, filtered and concentrated, the residue was purified with silica gel column chromatography (DCM/MeOH=200:1-50:1) to give the title product (40 mg, yield 50%). $^1$H-NMR (400 MHz, $CDCl_3$): δ 9.35 (d, J=4.1 Hz, 1H), 8.49 (t, J=5.9 Hz, 1H), 7.96 (dd, J=8.2, 6.0 Hz, 2H), 7.41-7.31 (m, 1H), 7.25-7.17 (m, 1H), 7.13 (dd, J=8.6, 2.5 Hz, 2H), 7.00 (t, J=8.4 Hz, 1H), 6.87 (d, J=8.3 Hz, 1H), 6.48 (ddd, J=14.5, 13.7, 7.2 Hz, 2H), 5.83-5.65 (m, 1H), 5.38-5.15 (m, 1H), 4.26-3.94 (m, 3H), 3.95-3.69 (m, 1H), 2.85-2.42 (m, 2H). LCMS: m/z=463.2 [M+H]+.

Example 5: (R)-1-(3-(3-(4-(2-fluoro-3-methoxyphenoxy) phenyl)-7-methyl-1H-pyrazolo [4,3-c]pyridin-1-yl) pyrrolidin-1-yl) prop-2-en-1-one

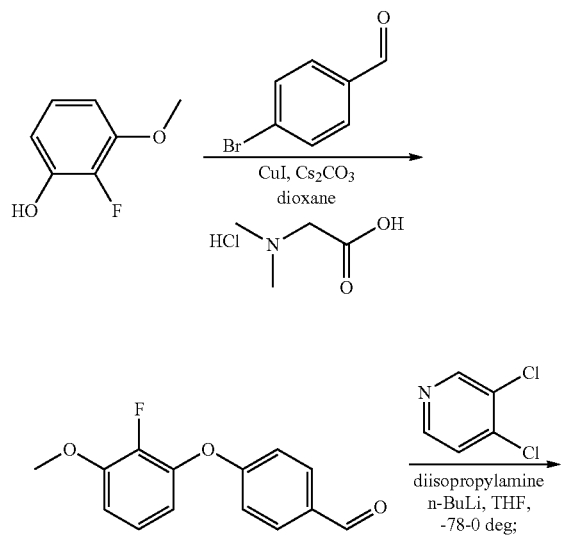

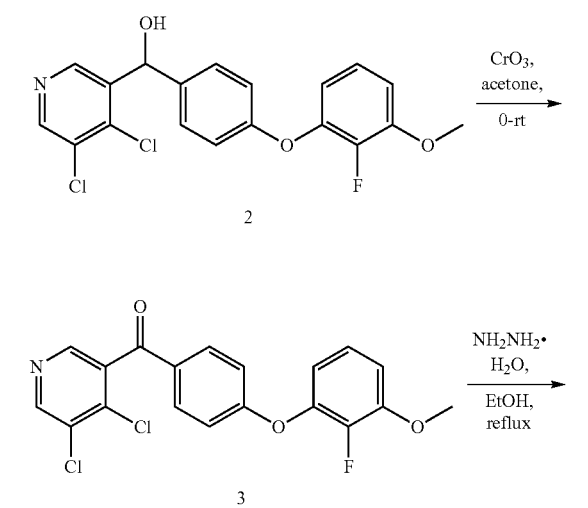

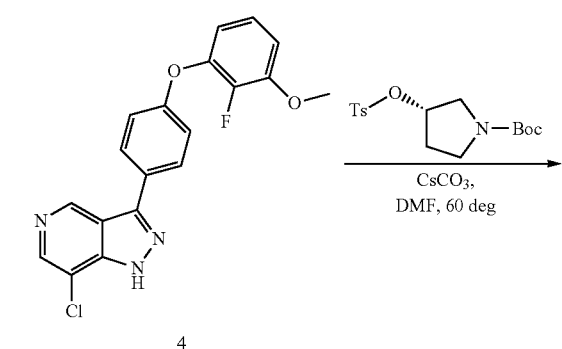

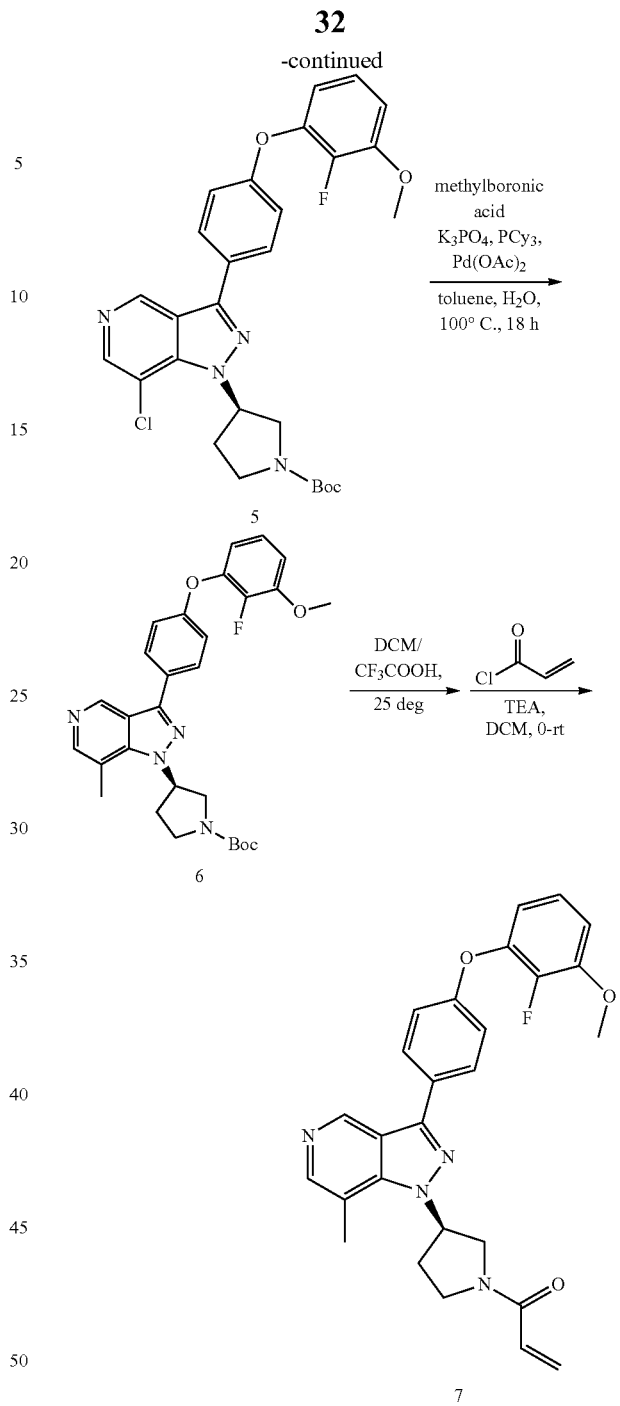

Step A:
4-(2-fluoro-3-methoxyphenoxy)benzaldehyde (1)

To a solution of 4-bromobenzaldehyde (6.99 g, 38 mmol, 1.2 eq) in dioxene (100 mL) was added 2-fluoro-3-methoxyphenol (4.5 g, 32 mmol, 1.0 eq), CuI (0.60 g, 3.2 mmol, 0.1 eq), N,N-Dimethylglycine hydrochloride (1.32 g, 9.5 mmol, 0.3 eq), Cs$_2$CO$_3$ (20.59 g, 60 mmol, 2 eq). The mixture was stirred at 100° C. in N$_2$ for 15 h. The mixture was filtered, contracted and extracted with EtOAc, The organic layer was washed with water and brine, dried with anhydrous Na$_2$SO$_4$, and purified by silica gel column chromatography to give the title product (4.1 g, 52.6%). ¹H-NMR (400 MHz, CDCl₃): δ 9.9 (s, 1H), 7.85-7.83 (m, 2H), 7.26-7.04 (m, 3H), 6.89-6.85 (m, 1H), 6.77-6.73 (m, 1H), 3.92 (s, 3H).

Step B: 4,5-dichloro pyridin-3-yl) (4-(2-fluoro-3-methoxyphenoxy)phenyl)-methanol (2)

To a solution of diisopropylamine (2.1 mL, 15.1 mmol, 1.1 eq) in dry THF (24 mL) at −78° C. was added a 2.5M BuLi solution in hexane (8.2 mL, 20.0 mmol, 1.3 eq). The mixture was allowed to warm to 0° C. and stirred around 1 h. After this time the solution was cooled to −78° C. and 3,4-dichloropyridine (2.0 g, 13.7 mmol, 1 eq) in 5 mL of dry THF was added. The reaction mixture was stirred for additional 4 h, and then the corresponding 4-(2-fluoro-3-methoxyphenoxy)benzaldehyde (3.36 g, 13.7 mmol, 1 eq) was added and the mixture was stirred and allowed to warm to room temperature during overnight. Excess of LDA was destroyed with H₂O (25 mL), and the mixture extracted with Et₂O (3×50 mL). The organic phases were combined, dried over Na₂SO₄, volatile components were removed under vacuum and the residue was purified by column chromatography on silica gel (gradient: DCM/MeOH=200:1-50/1) to give the title product (4.5 g, yield 83.6%). ¹H-NMR (400 MHz, CDCl₃): δ 8.78 (s, 1H), 8.55 (s, 1H), 7.30 (d, J=8.0 Hz, 2H), 7.02 (d, J=8.0 Hz, 2H), 6.98-6.66 (m, 3H), 6.12 (s, 1H), 3.93 (s, 3H). LCMS: m/z=394.1 [M+H]⁺.

Step C: (4,5-dichloro pyridin-3-yl)(4-(2-fluoro-3-methoxyphenoxy)phenyl)-methanone (3)

A solution of 4,5-dichloro pyridin-3-yl) (4-(2-fluoro-3-methoxyphenoxy) phenyl)methanol (2) (1 g, 2.5 mmol) in dry acetone (10 mL) was cooled to 0° C. and CrO₃ (0.92 g, 9.23 mmol) was added carefully in small portions. The resulting solution was stirred at room temperature until complete consumption of the starting material (3 h), after this time the reaction was quenched with 2-propanol (6 mL), and the mixture was stirred during 30 min. A saturated solution of NaHCO₃ (50 mL) was finally added to precipitate the chromium salts that were filtered over celite and washed with CH₂Cl₂ (6×15 mL). The solvent were removed under vacuum and the residue was purified by column chromatography on silica gel (gradient: DCM/MeOH=200: 1), to give the title product (0.69 g, yield 70.7%). LCMS: m/z=392.1 [M+H]⁺.

Step D: 7-chloro-3-(4-(2-fluoro-3-methoxyphenoxy) phenyl)-1H-pyrazolo[4,3-c]pyridine (4)

To a stirred solution (4-(benzyloxy)phenyl)(4-chloropyridin-3-yl)methanone (3) (0.7 g, 1.77 mol) in absolute ethanol (5 ml) was added hydrazine (1.08 g, 17.3 mol). The solution was heated under reflux for 3 h, cooled, the product filtered off and washed consecutively with water and methanol to give the title product (0.54 g, yield 83%). ¹H-NMR (400 MHz, CD₃OD): δ9.30 (s, 1H), 8.37 (s, 1H), 8.01 (d, J=8 Hz, 2H), 7.13-7.3.74 (m, 4H), 7.18 (d, J=8 Hz, 2H), 3.92 (S, 3H). LCMS: m/z=370.1 [M+H]⁺.

Step E: (R)-tert-butyl 3-(7-chloro-3-(4-(2-fluoro-3-methoxyphenoxy)phenyl)-1H-pyrazolo[4,3-c]pyridin-1-yl) pyrrolidine-1-carboxylate (5)

Into a 100 mL 3-necked round-bottom flask, was placed a solution of 3-(4-(benzyloxy)phenyl)-1H-pyrazolo[4,3-c] pyridine (4) (0.52 g, 1.41 mmol) in N,N-dimethylformamide (41 mL), (S)-tert-butyl-3-(tosyloxy)pyrrolidine-1-carboxylate (0.68 g, 1.99 mmol), and Cs₂CO₃ (0.97 g, 2.98 mmol). The resulting solution was stirred for 12 h at 60° C., and then quenched by the addition of 100 mL of water. The resulting solution was extracted with EA and the organic layers combined. The organics were washed with brine, dried over anhydrous NaHCO₃, The solvent were removed under vacuum and the residue was purified by column chromatography on silica gel (gradient: DCM/MeOH=200:1-100:1) to give the title product (0.68 g, yield 90%). LCMS: m/z=539.1 [M+H]⁺.

Step F: ((R)-tert-butyl 3-(3-(4-(2-fluoro-3-methoxyphenoxy) phenyl)-7-methyl-1H-pyrazolo[4,3-c]pyridin-1-yl)pyrrolidine-1-carboxylate (6)

To a solution of (R)-tert-butyl 3-(7-chloro-3-(4-(2-fluoro-3-methoxyphenoxy)phenyl)-1H-pyrazolo[4,3-c]pyridin-1-yl) pyrrolidine-1-carboxylate (100 mg, 0.18 mmol), methylboronic acid (12.2 mg, 0.20 mmol), K₃PO₄. H₂O (102 mg, 0.44 mmol) and tricyclohexylphosphine (10.09 mg, 0.036 mmol) in toluene (10.0 mL) and water (2 mL) under a nitrogen atmosphere was added diacetoxypalladium (5 mg g, 0.018 mmol), The mixture was heated to 100° C. overnight and then cooled to room temperature. Water (100 mL) was added and the mixture extracted with EtOAc, the combined organics were washed with brine, dried over MgSO₄ and concentrated in vacuo to afford the crude compound. the residue was purified with silica gel column chromatography (DCM/MeOH=200:1-50:1) to give the title product (25 mg, yield 26%). LCMS: m/z=519.1 [M+H]⁺.

Step G: (R)-1-(3-(3-(4-(2-fluoro-3-methoxyphenoxy)phenyl)-7-methyl-1H-pyrazolo[4,3-c]pyridin-1-yl)pyrrolidin-1-yl)prop-2-en-1-one (7)

((R)-tert-butyl 3-(3-(4-(2-fluoro-3-methoxyphenoxy)phenyl)-7-methyl-1H-pyrazolo[4,3-c]pyridin-1-yl)pyrrolidine-1-carboxylate (25 mg, 0.048 mmol) were added to CF₃COOH/DCM=4/1 (5 mL) in one portion. The mixture was stirred for about 1 h at rt. Volatile components were removed under vacuum to give the title crude product (20 mg), and directly used in next step without further purification. LCMS: m/z=419 [M+H]⁺.

A solution of Acryloyl chloride (4.3 mg, 0.048 mmol) in DCM (1 mL) was added to a stirred solution of (R)-3-(4-(2-fluoro-3-methoxyphenoxy) phenyl)-7-methyl-1-(pyrrolidin-3-yl)-1H-pyrazolo[4,3-c]pyridine (472-7) (20 mg, 0.048 mmol) and TEA (44 mg, 0.43 mmol) in DCM (5 mL) at 0° C. The reaction mixture was stirred for 1 h, poured onto brine and extracted with DCM. The organic layer was dried, concentrated and recrystallized from DCM/MeOH=100/1 to give the title product (11 mg, yield 50%). ¹H-NMR (400 MHz, CDCl₃): δ 9.18 (br, 1H), 8.21 (br, 1H), 7.89-7.86 (m, 2H), 7.26-7.02 (m, 3H), 6.83-6.49 (m, 2H), 6.43-6.41 (m, 2H), 5.74-5.71 (m, 1H), 5.34-5.29 (m, 1H), 4.13-3.93 (m, 6H), 2.73-2.19 (m, 4H), 2.04-2.00 (m, 2H). LCMS: m/z=473.2 [M+H]⁺.

Example 6: (R)-1-(3-(3-(4-(2-fluoro-3-methoxyphenoxy)phenyl)-7-methoxy-1H-pyrazolo[4,3-c]pyridin-1-yl)piperidin-1-yl)prop-2-en-1-one

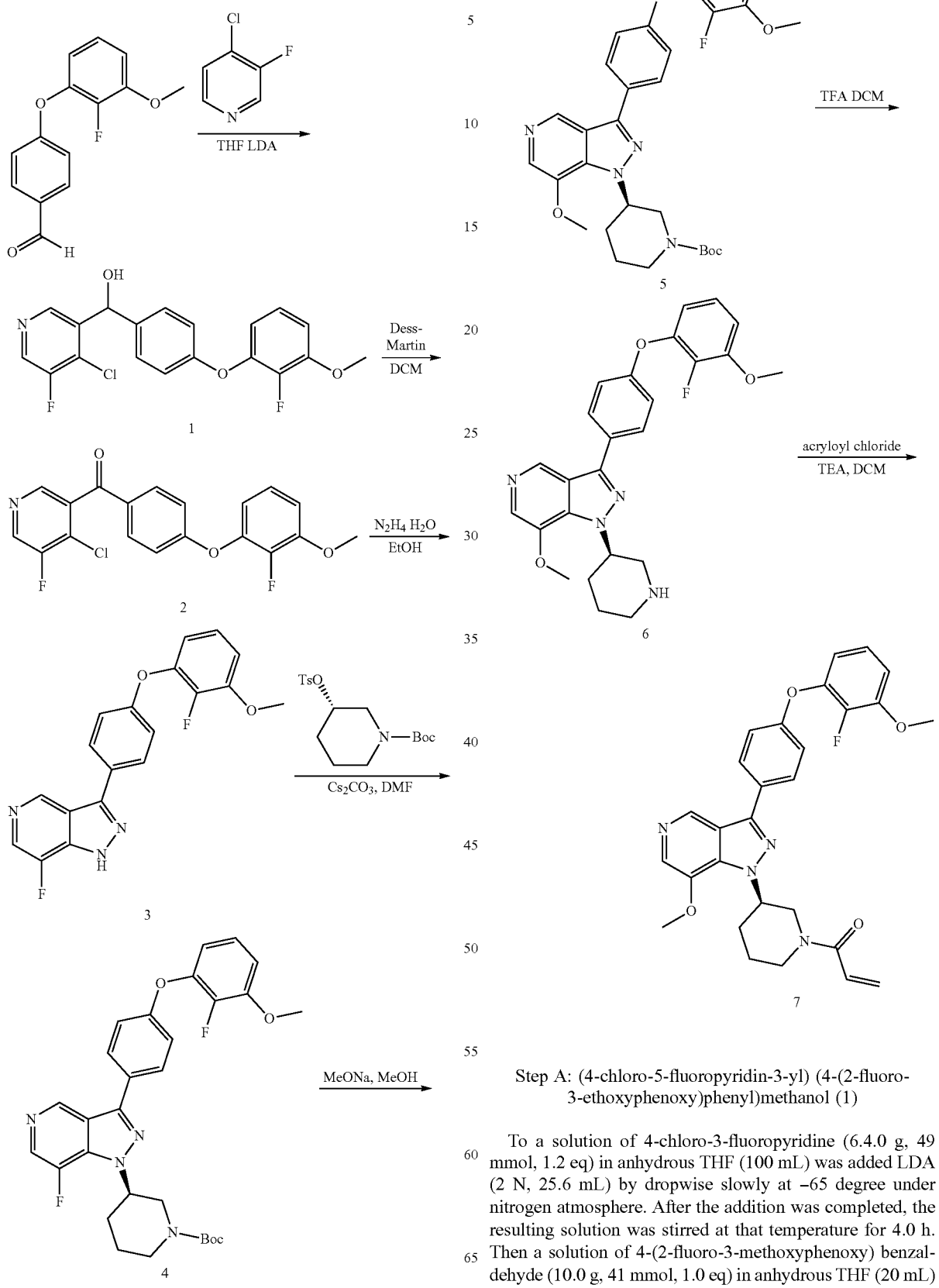

Step A: (4-chloro-5-fluoropyridin-3-yl) (4-(2-fluoro-3-ethoxyphenoxy)phenyl)methanol (1)

To a solution of 4-chloro-3-fluoropyridine (6.4.0 g, 49 mmol, 1.2 eq) in anhydrous THF (100 mL) was added LDA (2 N, 25.6 mL) by dropwise slowly at −65 degree under nitrogen atmosphere. After the addition was completed, the resulting solution was stirred at that temperature for 4.0 h. Then a solution of 4-(2-fluoro-3-methoxyphenoxy) benzaldehyde (10.0 g, 41 mmol, 1.0 eq) in anhydrous THF (20 mL) was added carefully at the same temperature. After the addition, the reaction was stirred at room temperature (15 degree) for 1.0 h, monitored by TLC and LCMS. The reaction mixture was quenched by water, then poured into water, extracted with ethyl acetate, washed with water and brine. The organic layer was dried over anhydrous $Na_2SO_4$, concentrated under vacuum to give crude product 1 and used to next step without further purification. LCMS: m/z=378.1 $[M+H]^+$.

Step B: (4-chloro-5-fluoropyridin-3-yl) (4-(2-fluoro-3-methoxyphenoxy)phenyl) methanone (2)

To a solution of 1 (10.0 g, (crude), 26.53 mmol, 1.0 eq) in DCM was added Dess-Martin (22.5 g, 53.05 mmol, 2.0 eq) by portions slowly under ice bath. The resulting solution was stirred at 15 degree for 4.0 h, monitored by TLC and LCMS. The reaction mixture was added the saturation $NaHCO_3$ solution, then filtrated. The filtrate was poured into water, extracted with DCM, washed with saturation $NaHCO_3$, $Na_2SO_3$ solution, water and brine. The organic solution was dried over anhydrous $Na_2SO_4$, concentrated under vacuum to give crude product 2 (10.0 g) and used to next step without further purification. LCMS: m/z=376.1 $[M+H]^+$.

Step C: 7-fluoro-3-(4-(2-fluoro-3-methoxyphenoxy)phenyl)-1H-pyrazolo[4,3-c]pyridine (3)

To a solution of 2 (48 g, 128 mmol, 1.0 eq) in EtOH (300 mL) was added $N_2H_4 \cdot H_2O$ (64 g, 1.28 mol, 10.0 eq). The resulting solution was stirred at 90 degree for 2.5 h. The reaction was monitored by TLC and LCMS, and the reaction mixture was cooled to room temperature, then filtrated. The cake was washed with EtOH and EA, dried under vacuum to give pure product 3 (33.3 g). $^1$H-NMR (400 MHz, $D_6$-DMSO): δ 9.24-9.23 (d, J=2.0 Hz, 1H), 8.39-8.38 (d, J=2.4 Hz, 1H), 8.08-8.06 (d, J=8.8 Hz, 2H), 7.22-7.17 (m, 1H), 7.14-7.06 (m, 3H), 6.86-6.82 (m, 1H), 3.90 (s, 3H). LCMS: m/z=354.1$[M+H]^+$.

Step D: (R)-tert-butyl 3-(7-fluoro-3-(4-(2-fluoro-3-methoxyphenoxy) phenyl)-1H-pyrazolo[4,3-c]pyridin-1-yl)piperidine-1-carboxylate (4)

A solution of 3 (20 g, 57 mmol, 1.0 eq), (S)-tert-butyl 3-(tosyloxy)piperidine-1-carboxylate (40 g, 113 mmol, 2.0 eq), cesium carbonate (37 g, 113 mmol, 2.0 eq) in DMF (20 mL) was stirred at 60 degree for 60 h. The reaction was monitored by LC-MS. The reaction mixture was cooled to room temperature, poured into water. The mixture was extracted with ethyl acetate, washed with water and brine. The organic layer was dried over anhydrous $Na_2SO_4$, concentrated under vacuum. The product was purified by silica gel column chromatography (DCM:MeOH=200:1 to 150:1) to give 4 (17 g). $^1$H-NMR (400 MHz, $CDCl_3$): δ 9.09 (s, 1H), 8.30-8.29 (d, J=3.2 Hz, 1H), 7.91-7.89 (d, J=8.4 Hz, 2H), 7.14-7.12 (d, J=8.4 Hz, 2H), 7.08-7.03 (m, 1H), 6.84-6.80 (m, 1H), 6.74-6.71 (m, 1H), 4.75-4.73 (m, 1H), 4.13-4.11 (m, 3H), 3.93 (s, 3H), 3.41-3.38 (m, 1H), 2.92-2.86 (m, 1H), 2.44-2.29 (m, 2H), 1.95-1.86 (m, 1H), 1.73-1.70 (m, 1H), 1.47-1.42 (m, 9H). LCMS: m/z=537.2$[M+H]^+$.

Step E: (R)-tert-butyl 3-(3-(4-(2-fluoro-3-methoxyphenoxy) phenyl)-7-methoxy-1H-pyrazolo[4,3-c]pyridin-1-yl)piperidine-1-carboxylate (5)

A solution of 4 (15 g, 28.0 mmol, 1.0 eq), MeONa (15 g, 280 mmol, 10.0 eq) in MeOH (120 mL) was added into 250 mL seal tube was stirred at 100 degree for overnight. The reaction was monitored by TLC and LC-MS. The reaction mixture was cooled to room temperature, poured into water, extracted with ethyl acetate, washed with water and brine. The organic layer was dried over anhydrous $Na_2SO_4$, concentrated under vacuum to give crude product. The product was purified by silica gel column chromatography (DCM:MeOH=150:1 to 100:1) to give 5 (13.2 g). $^1$H-NMR (400 MHz, $CDCl_3$): δ 8.94 (s, 1H), 7.99 (s, 1H), 7.91-7.89 (d, J=8.8 Hz, 2H), 7.13-7.11 (d, J=8.8 Hz, 2H), 7.06-7.01 (m, 1H), 6.82-6.78 (m, 1H), 6.73-6.69 (m, 1H), 5.06-5.04 (m, 1H), 4.14-4.11 (m, 1H), 4.08 (s, 3H), 3.93 (s, 3H), 3.37 (s, 1H), 2.89-2.83 (m, 1H), 2.30-2.24 (m, 2H), 1.92 (s, 1H), 1.70-1.67 (m, 1H), 1.48-1.44 (m, 11H). LCMS: m/z=549.2 $[M+H]^+$.

Step F: (R)-3-(4-(2-fluoro-3-methoxyphenoxy)phenyl)-7-methoxy-1-(piperidin-3-yl)-1H-pyrazolo[4,3-c]pyridine (6)

To a solution of 5 (13 g, 23.7 mmol) in DCM (100 mL) was added TFA (14 mL) at 18 degree for 4.0 h, the reaction was monitored by LC-MS and TLC. The reaction mixture was concentrated under vacuum to give crude product 6 (5.5 g) and used to next step without further purification. LCMS: m/z=449.2$[M+H]^+$.

Step G: (R)-1-(3-(3-(4-(2-fluoro-3-methoxyphenoxy)phenyl)-7-methoxy-1H-pyrazolo[4,3-c]pyridin-1-yl)piperidin-1-yl)prop-2-en-1-one (7)

To a solution of 6 (5.5 g, crude), TEA (2.2 g, 21.9 mmol, 2.0 eq) in anhydrous DCM (50 mL) was added acryloyl chloride (40 mg/mL in anhydrous DCM) at −30 deg. The resulting solution was stirred at 18 degree for 30 min, monitored by LC-MS and TLC. The reaction mixture was quenched by water, and then poured into water, extracted with DCM, washed with water and brine. The organic solution was dried over anhydrous $Na_2SO_4$, concentrated under vacuum. The product was purified by silica gel column chromatography (DCM:MeOH=200:1 to 150:1 to 100:1) to give 7 (3.2 g). $^1$H-NMR (400 MHz, $CDCl_3$): δ 8.95 (s, 1H), 8.00 (s, 1H), 7.91-7.89 (d, J=8.8 Hz, 2H), 7.14-7.11 (d, J=8.4 Hz, 2H), 7.06-7.02 (m, 1H), 6.83-6.79 (m, 1H), 6.73-6.70 (m, 1H), 6.64-6.61 (m, 1H), 6.34-6.30 (m, 1H), 5.73-5.67 (m, 1H), 5.07-4.66 (m, 2H), 4.29-4.06 (m, 4H), 3.93 (m, 3H), 3.625-2.82 (m, 2H), 2.32-1.72 (m, 4H). LCMS: m/z=503.2$[M+H]^+$.

The following additional Examples 7-99 shown in the Table below were prepared following the procedures outlined in the general methods above and detailed in Examples 1-6.

| Entry | Structure | MS(cald) [M + H]+/ MS (found) | Name |
|---|---|---|---|
| 7 | 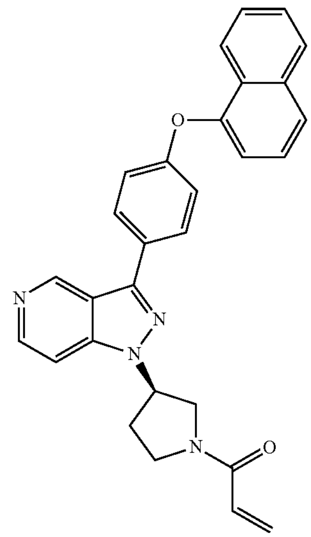 [SMILES: C=CC(=O)N1CC[C@@H](n2nc(-c3ccc(Oc4cccc5ccccc45)cc3)c3cnccc32)C1] | 461.19/ 461.2 | (R)-1-(3-(3-(4-(naphthalen-1-yloxy)phenyl)-1H-pyrazolo[4,3-c]pyridin-1-yl)pyrrolidin-1-yl)prop-2-en-1-one |
| 8 | 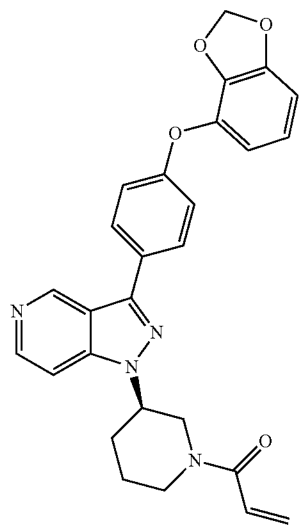 [SMILES: C=CC(=O)N1CCC[C@@H](n2nc(-c3ccc(Oc4cccc5c4OCO5)cc3)c3cnccc32)C1] | 469.18/ 469.2 | (R)-1-(3-(3-(4-(benzo[d][1,3]dioxol-4-yloxy)phenyl)-1H-pyrazolo[4,3-c]pyridin-1-yl)piperidin-1-yl)prop-2-en-1-one |
| 9 | 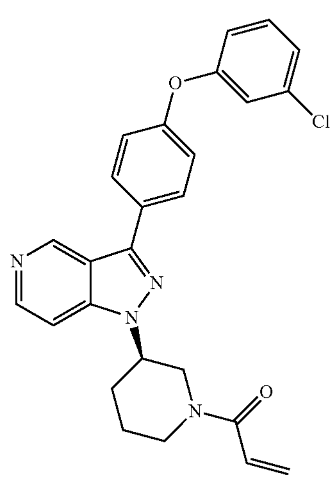 [SMILES: C=CC(=O)N1CCC[C@@H](n2nc(-c3ccc(Oc4cccc(Cl)c4)cc3)c3cnccc32)C1] | 459.15/ 459.2 | (R)-1-(3-(3-(4-(3-chlorophenoxy)phenyl)-1H-pyrazolo[4,3-c]pyridin-1-yl)piperidin-1-yl)prop-2-en-1-one |

-continued

| Entry | Structure | MS(cald) [M + H]+/ MS (found) | Name |
|---|---|---|---|
| 10 | 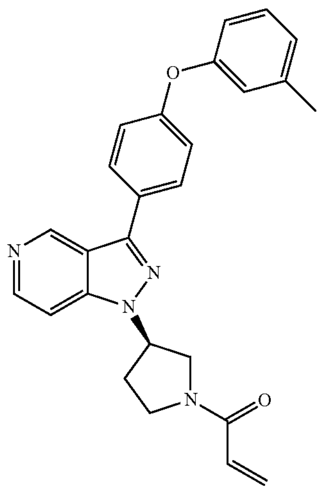 [SMILES: C=CC(=O)N1CC[C@@H](n2nc(-c3ccc(Oc4cccc(C)c4)cc3)c3cnccc32)C1] | 425.19/ 425.2 | (R)-1-(3-(3-(4-(m-tolyloxy)phenyl)-1H-pyrazolo[4,3-c]pyridin-1-yl)pyrrolidin-1-yl)prop-2-en-1-one |
| 11 | 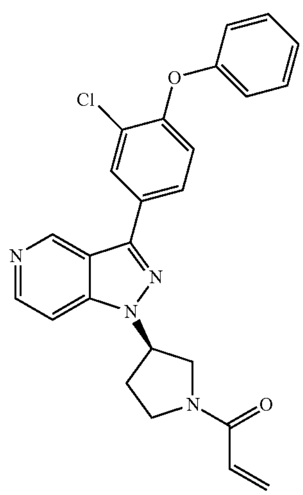 [SMILES: C=CC(=O)N1CC[C@@H](n2nc(-c3ccc(Oc4ccccc4)c(Cl)c3)c3cnccc32)C1] | 445.14/ 445.2 | (R)-1-(3-(3-(3-chloro-4-phenoxyphenyl)-1H-pyrazolo[4,3-c]pyridin-1-yl)pyrrolidin-1-yl)prop-2-en-1-one |
| 12 | 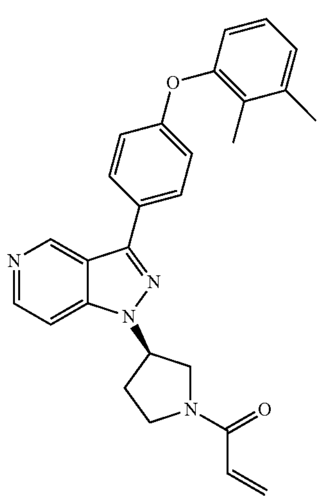 [SMILES: C=CC(=O)N1CC[C@@H](n2nc(-c3ccc(Oc4cccc(C)c4C)cc3)c3cnccc32)C1] | 439.21/ 439.2 | (R)-1-(3-(3-(4-(2,3-dimethylphenoxy)phenyl)-1H-pyrazolo[4,3-c]pyridin-1-yl)pyrrolidin-1-yl)prop-2-en-1-one<br>Exact Mass: 438.21 |

-continued

| Entry | Structure | MS(cald) [M + H]+/ MS (found) | Name |
|---|---|---|---|
| 13 | 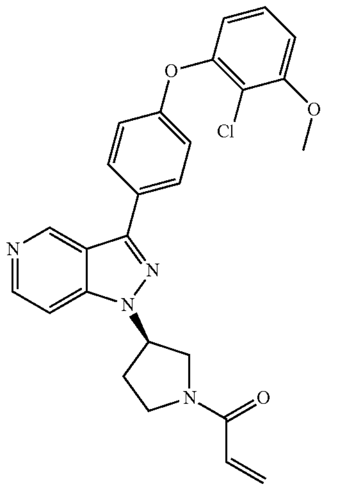 [SMILES: C=CC(=O)N1CC[C@@H](n2nc(-c3ccc(Oc4cccc(OC)c4Cl)cc3)c3cnccc32)C1] | 475.15/ 475.2 | (R)-1-(3-(3-(4-(2-chloro-3-methoxyphenoxy)phenyl)-1H-pyrazolo[4,3-c]pyridin-1-yl)pyrrolidin-1-yl)prop-2-en-1-one |
| 14 | 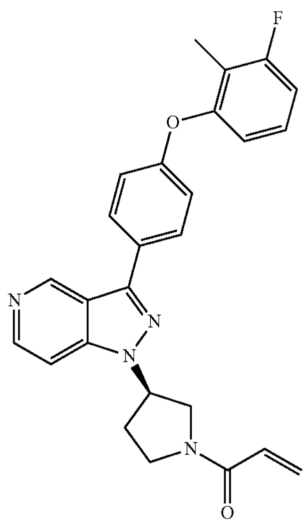 [SMILES: C=CC(=O)N1CC[C@@H](n2nc(-c3ccc(Oc4cccc(F)c4C)cc3)c3cnccc32)C1] | 443.18/ 443.2 | (R)-1-(3-(3-(4-(3-fluoro-2-methylphenoxy)phenyl)-1H-pyrazolo[4,3-c]pyridin-1-yl)pyrrolidin-1-yl)prop-2-en-1-one |
| 15 | 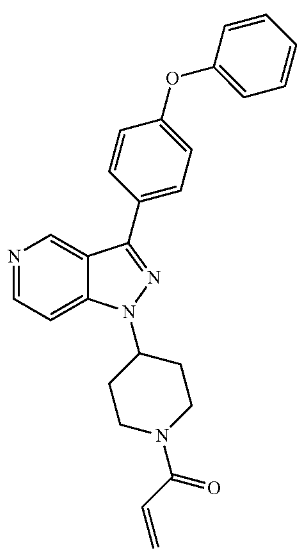 [SMILES: C=CC(=O)N1CCC(n2nc(-c3ccc(Oc4ccccc4)cc3)c3cnccc32)CC1] | 425.19/ 425.2 | 1-(4-(3-(4-phenoxyphenyl)-1H-pyrazolo[4,3-c]pyridin-1-yl)piperidin-1-yl)prop-2-en-1-one |

-continued

| Entry | Structure | MS(cald) [M + H]+/ MS (found) | Name |
|---|---|---|---|
| 16 | 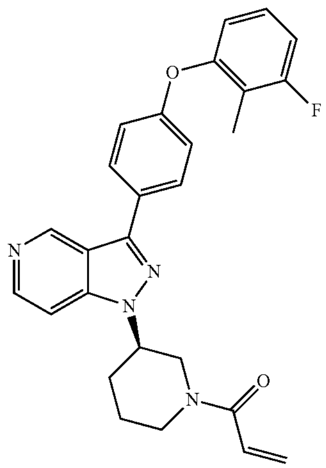 [SMILES: C=CC(=O)N1CCC[C@@H](n2nc(-c3ccc(Oc4cccc(F)c4C)cc3)c3cnccc32)C1] | 457.20/ 457.2 | (R)-1-(3-(3-(4-(3-fluoro-2-methylphenoxy)phenyl)-1H-pyrazolo[4,3-c]pyridin-1-yl)piperidin-1-yl)prop-2-en-1-one |
| 17 | 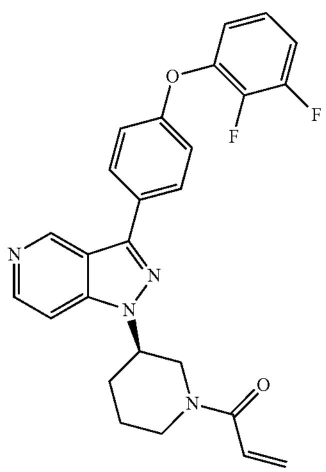 [SMILES: C=CC(=O)N1CCC[C@@H](n2nc(-c3ccc(Oc4cccc(F)c4F)cc3)c3cnccc32)C1] | 461.17/ 461.2 | (R)-1-(3-(3-(4-(2,3-difluorophenoxy)phenyl)-1H-pyrazolo[4,3-c]pyridin-1-yl)piperidin-1-yl)prop-2-en-1-one |
| 18 | 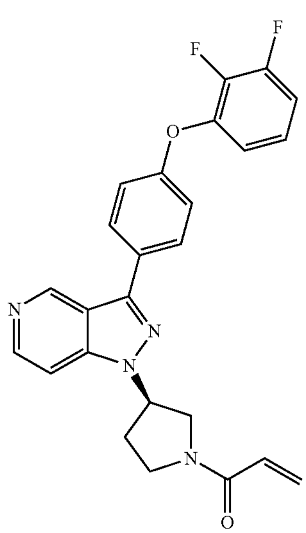 [SMILES: C=CC(=O)N1CC[C@@H](n2nc(-c3ccc(Oc4cccc(F)c4F)cc3)c3cnccc32)C1] | 447.16/ 447.2 | (R)-1-(3-(3-(4-(2,3-difluorophenoxy)phenyl)-1H-pyrazolo[4,3-c]pyridin-1-yl)pyrrolidin-1-yl)prop-2-en-1-one |

-continued

| Entry | Structure | MS(cald) [M + H]+/ MS (found) | Name |
|---|---|---|---|
| 19 | 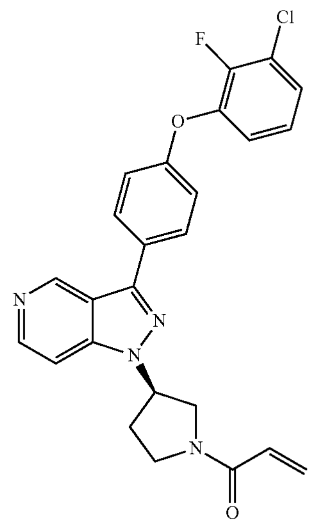 [SMILES: C=CC(=O)N1CC[C@@H](n2nc(-c3ccc(Oc4cccc(Cl)c4F)cc3)c3cnccc32)C1] | 463.13/ 463.1 | (R)-1-(3-(3-(4-(3-chloro-2-fluorophenoxy)phenyl)-1H-pyrazolo[4,3-c]pyridin-1-yl)pyrrolidin-1-yl)prop-2-en-1-one |
| 20 | 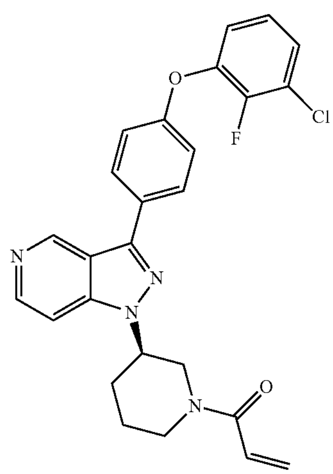 [SMILES: C=CC(=O)N1CCC[C@@H](n2nc(-c3ccc(Oc4cccc(Cl)c4F)cc3)c3cnccc32)C1] | 477.14/ 477.1 | (R)-1-(3-(3-(4-(3-chloro-2-fluorophenoxy)phenyl)-1H-pyrazolo[4,3-c]pyridin-1-yl)piperidin-1-yl)prop-2-en-1-one |
| 21 | 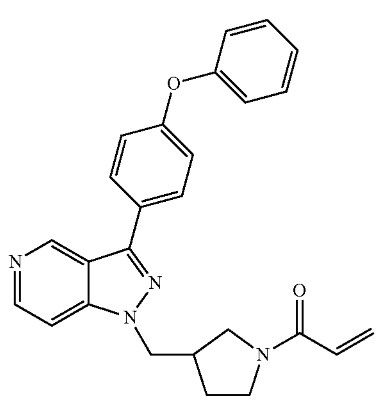 [SMILES: C=CC(=O)N1CCC(Cn2nc(-c3ccc(Oc4ccccc4)cc3)c3cnccc32)C1] | 425.19/ 425.2 | 1-(3-((3-(4-phenoxyphenyl)-1H-pyrazolo[4,3-c]pyridin-1-yl)methyl)pyrrolidin-1-yl)prop-2-en-1-one |

-continued

| Entry | Structure | MS(cald) [M + H]+/ MS (found) | Name |
|---|---|---|---|
| 22 | 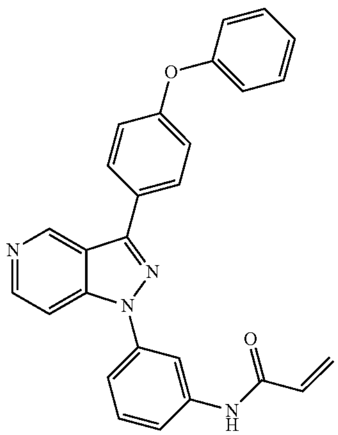 [SMILES: C=CC(=O)Nc1cccc(-n2nc(-c3ccc(Oc4ccccc4)cc3)c3cnccc32)c1] | 433.16/ 433.2 | N-(3-(3-(4-phenoxyphenyl)-1H-pyrazolo[4,3-c]pyridin-1-yl)phenyl)acrylamide |
| 23 | 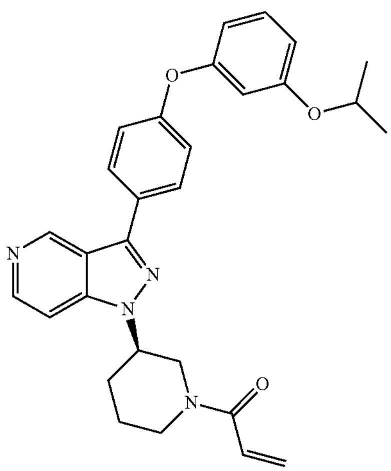 [SMILES: C=CC(=O)N1CCC[C@@H](n2nc(-c3ccc(Oc4cccc(OC(C)C)c4)cc3)c3cnccc32)C1] | 483.23/ 483.2 | (R)-1-(3-(3-(4-(3-isopropoxyphenoxy)phenyl)-1H-pyrazolo[4,3-c]pyridin-1-yl)piperidin-1-yl)prop-2-en-1-one |
| 24 | 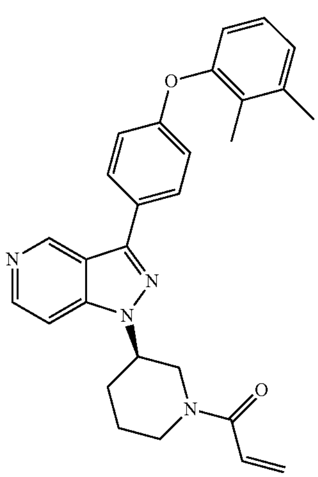 [SMILES: C=CC(=O)N1CCC[C@@H](n2nc(-c3ccc(Oc4cccc(C)c4C)cc3)c3cnccc32)C1] | 453.22/ 453.2 | (R)-1-(3-(3-(4-(2,3-dimethylphenoxy)phenyl)-1H-pyrazolo[4,3-c]pyridin-1-yl)piperidin-1-yl)prop-2-en-1-one |

-continued

| Entry | Structure | MS(cald) [M + H]+/ MS (found) | Name |
| --- | --- | --- | --- |
| 25 | 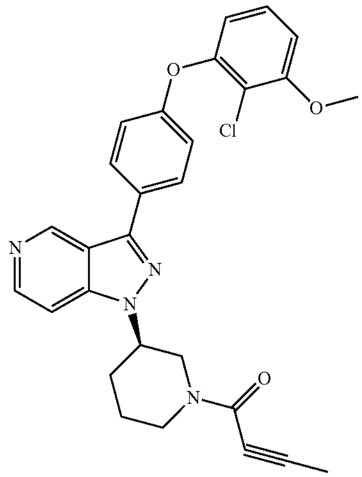 [SMILES: CC#CC(=O)N1CCC[C@@H](n2nc(-c3ccc(Oc4cccc(OC)c4Cl)cc3)c3cnccc32)C1] | 501.16/ 501.2 | (R)-1-(3-(3-(4-(2-chloro-3-methoxyphenoxy)phenyl)-1H-pyrazolo[4,3-c]pyridin-1-yl)piperidin-1-yl)but-2-yn-1-one |
| 26 | 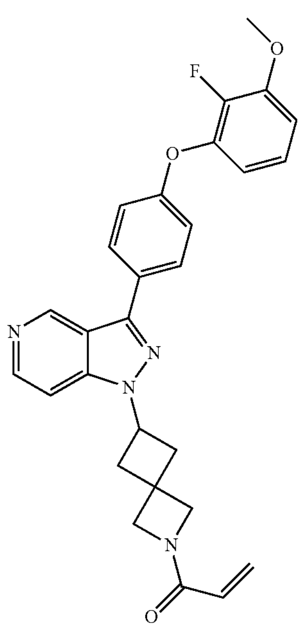 [SMILES: C=CC(=O)N1CC2(CC(n3nc(-c4ccc(Oc5cccc(OC)c5F)cc4)c4cnccc43)C2)C1] | 485.19/ 485.2 | 1-(6-(3-(4-(2-fluoro-3-methoxyphenoxy)phenyl)-1H-pyrazolo[4,3-c]pyridin-1-yl)-2-azaspiro[3.3]heptan-2-yl)prop-2-en-1-one |

| Entry | Structure | MS(cald) [M + H]+/ MS (found) | Name |
|---|---|---|---|
| 27 | 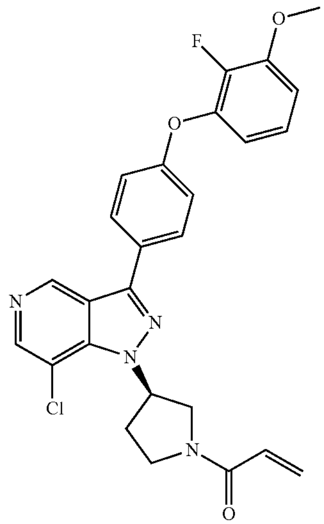 [SMILES: C=CC(=O)N1CC[C@@H](n2nc(-c3ccc(Oc4cccc(OC)c4F)cc3)c3cncc(Cl)c32)C1] | 493.14/ 493.1 | (R)-1-(3-(7-chloro-3-(4-(2-fluoro-3-methoxyphenoxy)phenyl)-1H-pyrazolo[4,3-c]pyridin-1-yl)pyrrolidin-1-yl)prop-2-en-1-one |
| 28 | 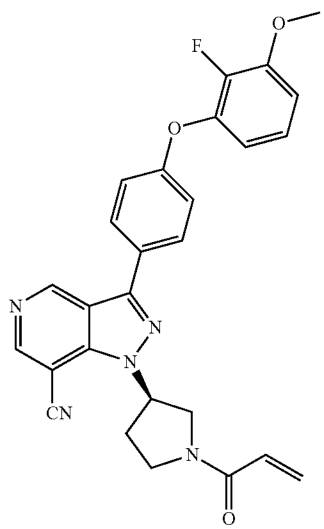 [SMILES: C=CC(=O)N1CC[C@@H](n2nc(-c3ccc(Oc4cccc(OC)c4F)cc3)c3cncc(C#N)c32)C1] | 484.17/ 484.2 | (R)-1-(1-acryloylpyrrolidin-3-yl)-3-(4-(2-fluoro-3-methoxyphenoxy)phenyl)-1H-pyrazolo[4,3-c]pyridine-7-carbonitrile |
| 29 | 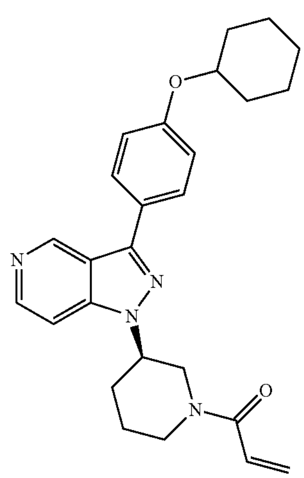 [SMILES: C=CC(=O)N1CCC[C@@H](n2nc(-c3ccc(OC4CCCCC4)cc3)c3cnccc32)C1] | 431.24/ 431.2 | (R)-1-(3-(3-(4-(cyclohexyloxy)phenyl)-1H-pyrazolo[4,3-c]pyridin-1-yl)piperidin-1-yl)prop-2-en-1-one |

-continued

| Entry | Structure | MS(cald) [M + H]⁺/ MS (found) | Name |
|---|---|---|---|
| 30 | 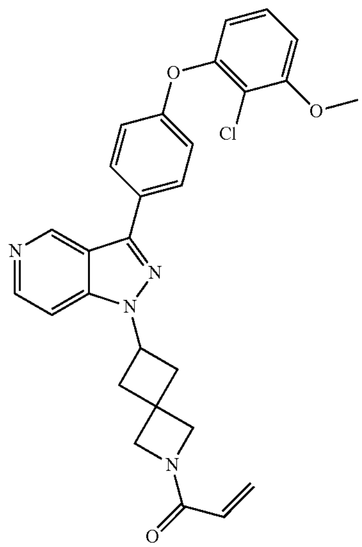 [SMILES: C=CC(=O)N1CC2(CC(n3nc(-c4ccc(Oc5cccc(OC)c5Cl)cc4)c4cnccc43)C2)C1] | 501.16/ 501.2 | 1-(6-(3-(4-(2-chloro-3-methoxyphenoxy)phenyl)-1H-pyrazolo[4,3-c]pyridin-1-yl)-2-azaspiro[3.3]heptan-2-yl)prop-2-en-1-one |
| 31 | 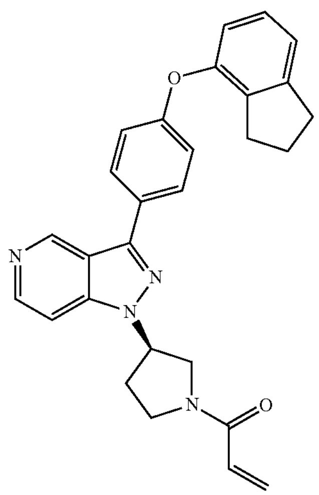 [SMILES: C=CC(=O)N1CC[C@@H](n2nc(-c3ccc(Oc4cccc5c4CCC5)cc3)c3cnccc32)C1] | 451.21/ 451.2 | (R)-1-(3-(3-(4-((2,3-dihydro-1H-inden-4-yl)oxy)phenyl)-1H-pyrazolo[4,3-c]pyridin-1-yl)pyrrolidin-1-yl)prop-2-en-1-one |
| 32 | 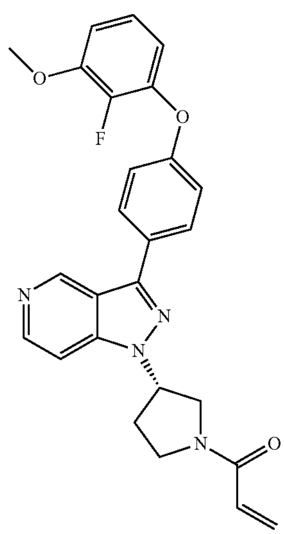 [SMILES: C=CC(=O)N1CC[C@H](n2nc(-c3ccc(Oc4cccc(OC)c4F)cc3)c3cnccc32)C1] | 458.18/ 458.2 | (R)-1-(3-(3-(4-(2-fluoro-3-methoxyphenoxy)phenyl)-1H-pyrazolo[3,4-c]pyridin-1-yl)pyrrolidin-1-yl)prop-2-en-1-one |

-continued

| Entry | Structure | MS(cald) [M + H]+/ MS (found) | Name |
|---|---|---|---|
| 33 | 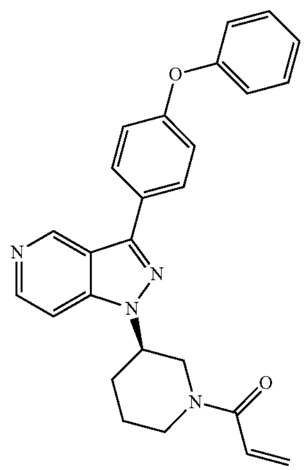 [SMILES: C=CC(=O)N1CCC[C@@H](n2nc(-c3ccc(Oc4ccccc4)cc3)c3cnccc32)C1] | 425.19/ 425.2 | (R)-1-(3-(3-(4-phenoxyphenyl)-1H-pyrazolo[4,3-c]pyridin-1-yl)piperidin-1-yl)prop-2-en-1-one |
| 34 | 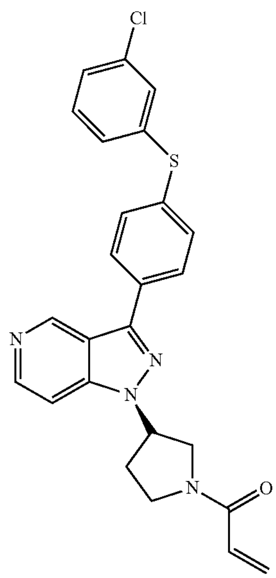 | 460.11/ 460.1 | (S)-1-(3-(3-(4-((3-chlorophenyl)thio)phenyl)-1H-pyrazolo[4,3-c]pyridin-1-yl)pyrrolidin-1-yl)prop-2-en-1-one |
| 35 | 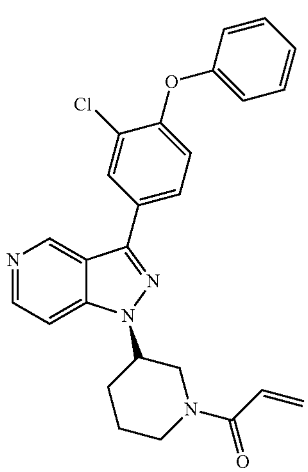 | 459.15 459.2 | (S)-1-(3-(3-(3-chloro-4-phenoxyphenyl)-1H-pyrazolo[4,3-c]pyridin-1-yl)piperidin-1-yl)prop-2-en-1-one |

| Entry | Structure | MS(cald) [M + H]+/ MS (found) | Name |
|---|---|---|---|
| 36 | 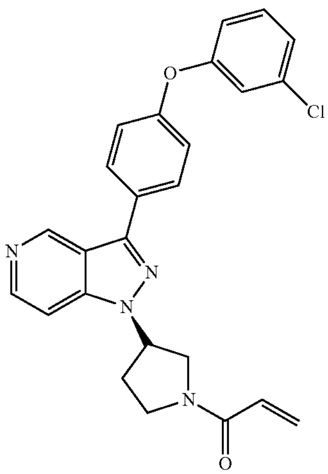 | 445.14/ 445.1 | (S)-1-(3-(3-(4-(3-chlorophenoxy)phenyl)-1H-pyrazolo[4,3-c]pyridin-1-yl)pyrrolidin-1-yl)prop-2-en-1-one |
| 37 | 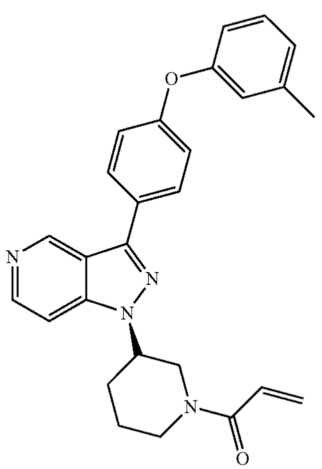 | 439.21/ 439.2 | (S)-1-(3-(3-(4-(m-tolyloxy)phenyl)-1H-pyrazolo[4,3-c]pyridin-1-yl)piperidin-1-yl)prop-2-en-1-one |
| 38 | 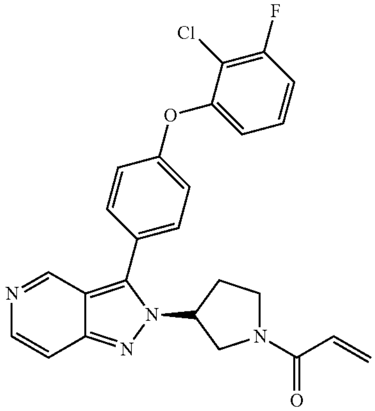 | 463.13/ 463.1 | (R)-1-(3-(3-(4-(2-chloro-3-fluorophenoxy)phenyl)-2H-pyrazolo[4,3-c]pyridin-2-yl)pyrrolidin-1-yl)prop-2-en-1-one |

-continued
| Entry | Structure | MS(cald) [M + H]+/ MS (found) | Name |
|---|---|---|---|
| 39 | 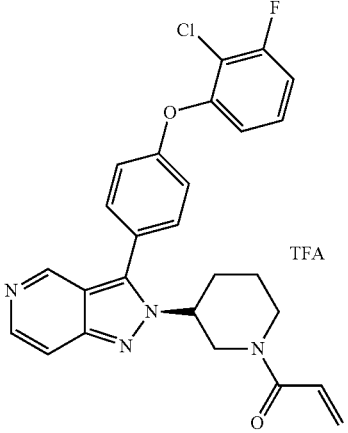 TFA | 477.14/ 477.2 | (R)-1-(3-(3-(4-(2-chloro-3-fluorophenoxy)phenyl)-2H-pyrazolo[4,3-c]pyridin-2-yl)piperidin-1-yl)prop-2-en-1-one |
| 40 | 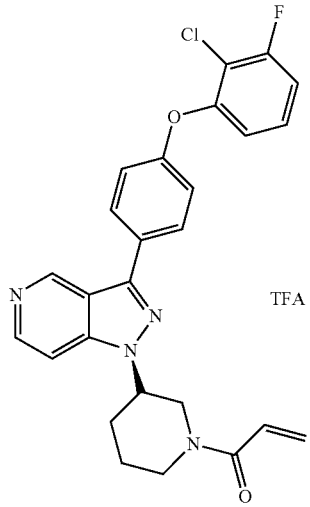 TFA | 477.14/ 477.2 | (S)-1-(3-(3-(4-(2-chloro-3-fluorophenoxy)phenyl)-1H-pyrazolo[4,3-c]pyridin-1-yl)piperidin-1-yl)prop-2-en-1-one |
| 41 | 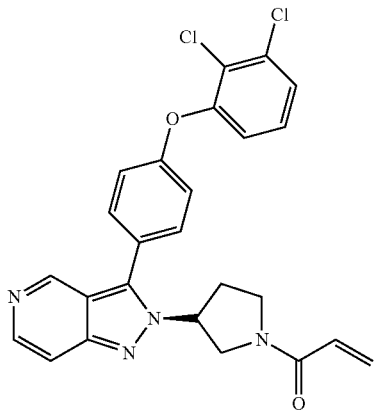 | 479.10/ 479.1 | (R)-1-(3-(3-(4-(2,3-dichlorophenoxy)phenyl)-2H-pyrazolo[4,3-c]pyridin-2-yl)pyrrolidin-1-yl)prop-2-en-1-one |

| Entry | Structure | MS(cald) [M + H]+/ MS (found) | Name |
|---|---|---|---|
| 42 | 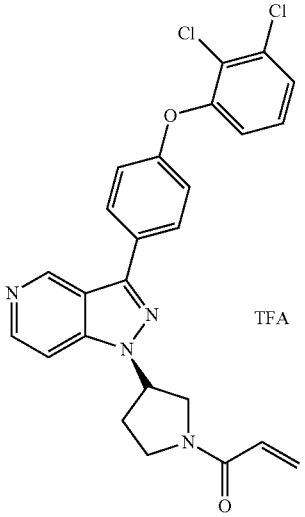 TFA | 479.10/ 479.1 | (S)-1-(3-(3-(4-(2,3-dichlorophenoxy)phenyl)-1H-pyrazolo[4,3-c]pyridin-1-yl)pyrrolidin-1-yl)prop-2-en-1-one |
| 43 | 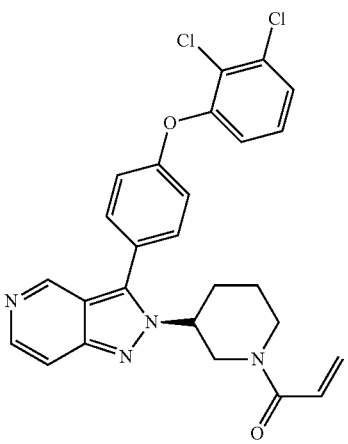 | 493.11/ 493.1 | (R)-1-(3-(3-(4-(2,3-dichlorophenoxy)phenyl)-2H-pyrazolo[4,3-c]pyridin-2-yl)piperidin-1-yl)prop-2-en-1-one |
| 44 | 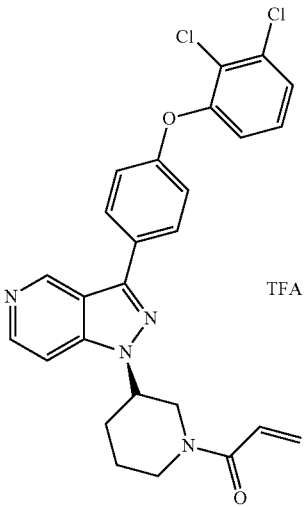 TFA | 493.11/ 493.1 | (S)-1-(3-(3-(4-(2,3-dichlorophenoxy)phenyl)-1H-pyrazolo[4,3-c]pyridin-1-yl)piperidin-1-yl)prop-2-en-1-one |

| Entry | Structure | MS(cald) [M + H]+/ MS (found) | Name |
|---|---|---|---|
| 45 | 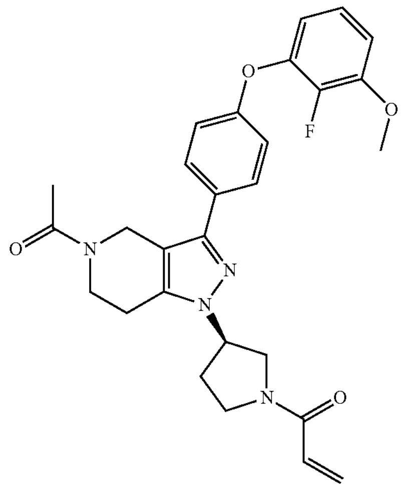 [SMILES: C=CC(=O)N1CC[C@@H](n2nc(-c3ccc(Oc4cccc(OC)c4F)cc3)c3c2CCN(C(C)=O)C3)C1] | 505.22/ 505.2 | (R)-1-(3-(5-acetyl-3-(4-(2-fluoro-3-methoxyphenoxy)phenyl)-4,5,6,7-tetrahydro-1H-pyrazolo[4,3-c]pyridin-1-yl)pyrrolidin-1-yl)prop-2-en-1-one |
| 46 | 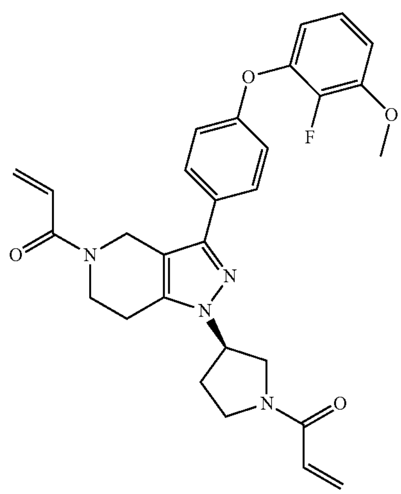 [SMILES: C=CC(=O)N1CCc2c(c(-c3ccc(Oc4cccc(OC)c4F)cc3)nn2[C@@H]2CCN(C(=O)C=C)C2)C1] | 517.22/ 517.2 | (R)-1-(3-(5-acryloyl-3-(4-(2-fluoro-3-methoxyphenoxy)phenyl)-4,5,6,7-tetrahydro-1H-pyrazolo[4,3-c]pyridin-1-yl)pyrrolidin-1-yl)prop-2-en-1-one |
| 47 | 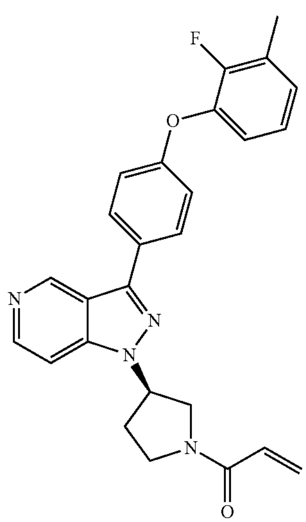 [SMILES: C=CC(=O)N1CC[C@@H](n2nc(-c3ccc(Oc4cccc(C)c4F)cc3)c3cnccc32)C1] | 443.18/ 443.2 | (R)-1-(3-(3-(4-(2-fluoro-3-methylphenoxy)phenyl)-1H-pyrazolo[4,3-c]pyridin-1-yl)pyrrolidin-1-yl)prop-2-en-1-one |

-continued

| Entry | Structure | MS(cald) [M + H]+/ MS (found) | Name |
|---|---|---|---|
| 48 | 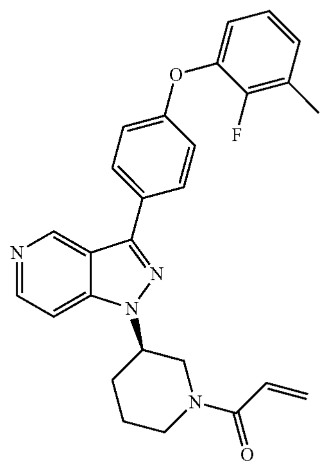 [SMILES: C=CC(=O)N1CCC[C@@H](n2nc(-c3ccc(Oc4cccc(C)c4F)cc3)c3cnccc32)C1] | 457.20/ 457.2 | (R)-1-(3-(3-(4-(2-fluoro-3-methylphenoxy)phenyl)-1H-pyrazolo[4,3-c]pyridin-1-yl)piperidin-1-yl)prop-2-en-1-one |
| 49 | 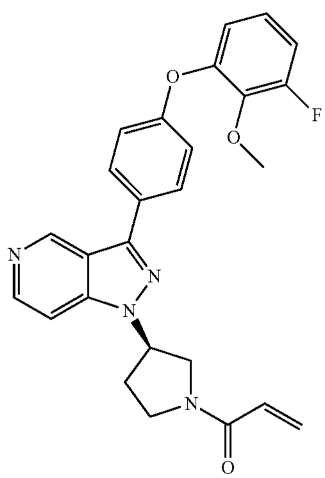 [SMILES: C=CC(=O)N1CC[C@@H](n2nc(-c3ccc(Oc4cccc(F)c4OC)cc3)c3cnccc32)C1] | 459.18/ 459.2 | (R)-1-(3-(3-(4-(3-fluoro-2-methoxyphenoxy)phenyl)-1H-pyrazolo[4,3-c]pyridin-1-yl)pyrrolidin-1-yl)prop-2-en-1-one |
| 50 | 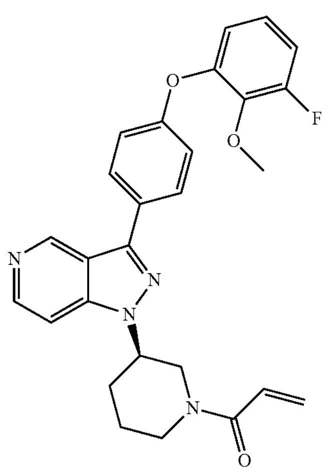 [SMILES: C=CC(=O)N1CCC[C@@H](n2nc(-c3ccc(Oc4cccc(F)c4OC)cc3)c3cnccc32)C1] | 473.19/ 473.2 | (R)-1-(3-(3-(4-(3-fluoro-2-methoxyphenoxy)phenyl)-1H-pyrazolo[4,3-c]pyridin-1-yl)piperidin-1-yl)prop-2-en-1-one |

-continued
| Entry | Structure | MS(cald) [M + H]+/ MS (found) | Name |
|---|---|---|---|
| 51 | 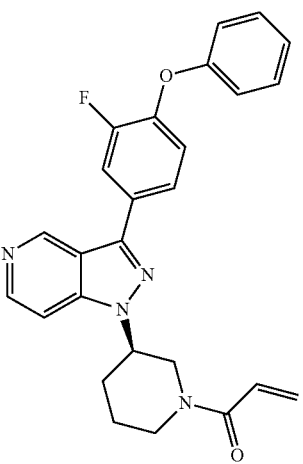 [SMILES: C=CC(=O)N1CCC[C@@H](n2nc(-c3ccc(Oc4ccccc4)c(F)c3)c3cnccc32)C1] | 443.18/ 443.2 | (R)-1-(3-(3-(3-fluoro-4-phenoxyphenyl)-1H-pyrazolo[4,3-c]pyridin-1-yl)piperidin-1-yl)prop-2-en-1-one |
| 52 | 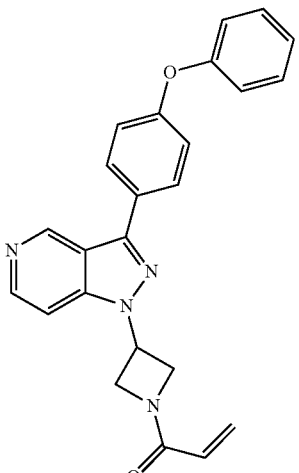 | 397-16/ 397.2 | 1-(3-(3-(4-phenoxyphenyl)-1H-pyrazolo[4,3-c]pyridin-1-yl)azetidin-1-yl)prop-2-en-1-one |
| 53 | 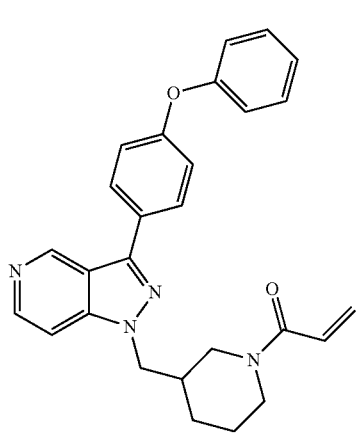 [SMILES: C=CC(=O)N1CCCC(Cn2nc(-c3ccc(Oc4ccccc4)cc3)c3cnccc32)C1] | 439.21/ 439-2 | 1-(3-((3-(4-phenoxyphenyl)-1H-pyrazolo[4,3-c]pyridin-1-yl)methyl)piperidin-1-yl)prop-2-en-1-one |

-continued

| Entry | Structure | MS(cald) [M + H]+/ MS (found) | Name |
|---|---|---|---|
| 54 | 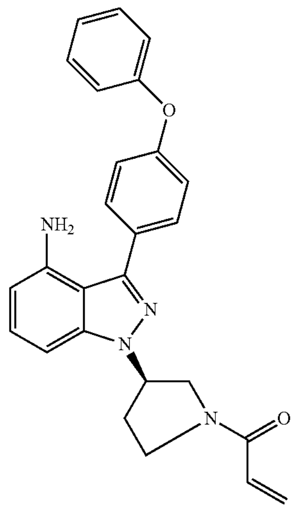 [SMILES: C=CC(=O)N1CC[C@@H](n2nc(-c3ccc(Oc4ccccc4)cc3)c3c(N)cccc32)C1] | 425.19/ 425.2 | (R)-1-(3-(4-amino-3-(4-phenoxyphenyl)-1H-indazol-1-yl)pyrrolidin-1-yl)prop-2-en-1-one |
| 55 | 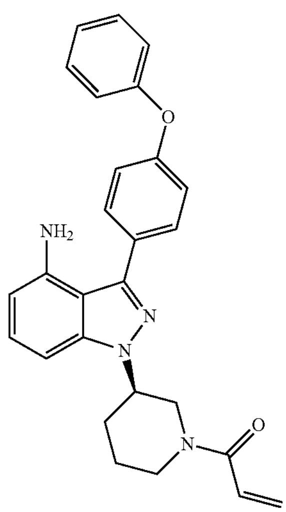 [SMILES: C=CC(=O)N1CCC[C@@H](n2nc(-c3ccc(Oc4ccccc4)cc3)c3c(N)cccc32)C1] | 439.21/ 439.2 | (R)-1-(3-(4-amino-3-(4-phenoxyphenyl)-1H-indazol-1-yl)piperidin-1-yl)prop-2-en-1-one |
| 56 | 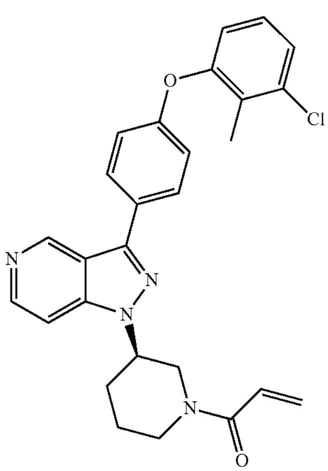 [SMILES: C=CC(=O)N1CCC[C@@H](n2nc(-c3ccc(Oc4cccc(Cl)c4C)cc3)c3cnccc32)C1] | 473.17/ 473.2 | (R)-1-(3-(3-(4-(3-chloro-2-methylphenoxy)phenyl)-1H-pyrazolo[4,3-c]pyridin-1-yl)piperidin-1-yl)prop-2-en-1-one |

-continued

| Entry | Structure | MS(cald) [M + H]+/ MS (found) | Name |
|---|---|---|---|
| 57 | 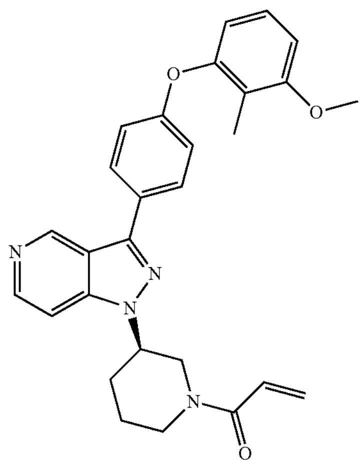 [SMILES: C=CC(=O)N1CCC[C@@H](n2nc(-c3ccc(Oc4cccc(OC)c4C)cc3)c3cnccc32)C1] | 469.22/ 469.2 | (R)-1-(3-(3-(4-(3-methoxy-2-methylphenoxy)phenyl)-1H-pyrazolo[4,3-c]pyridin-1-yl)piperidin-1-yl)prop-2-en-1-one |
| 58 | 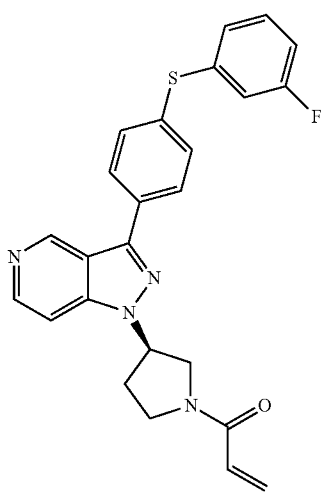 [SMILES: C=CC(=O)N1CC[C@@H](n2nc(-c3ccc(Sc4cccc(F)c4)cc3)c3cnccc32)C1] | 445.14/ 445.1 | (R)-1-(3-(3-(4-((3-fluorophenyl)thio)phenyl)-1H-pyrazolo[4,3-c]pyridin-1-yl)pyrrolidin-1-yl)prop-2-en-1-one |
| 59 | 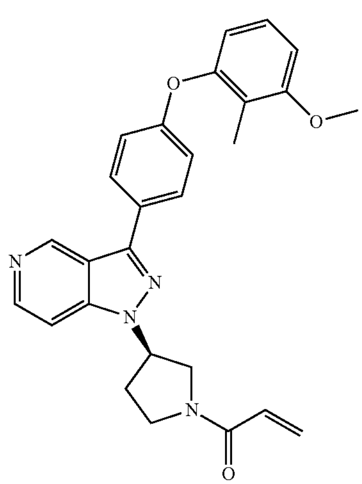 [SMILES: C=CC(=O)N1CC[C@@H](n2nc(-c3ccc(Oc4cccc(OC)c4C)cc3)c3cnccc32)C1] | 455.20/ 455.2 | (R)-1-(3-(3-(4-(3-methoxy-2-methylphenoxy)phenyl)-1H-pyrazolo[4,3-c]pyridin-1-yl)pyrrolidin-1-yl)prop-2-en-1-one |

-continued

| Entry | Structure | MS(cald) [M + H]⁺/ MS (found) | Name |
|---|---|---|---|
| 60 | 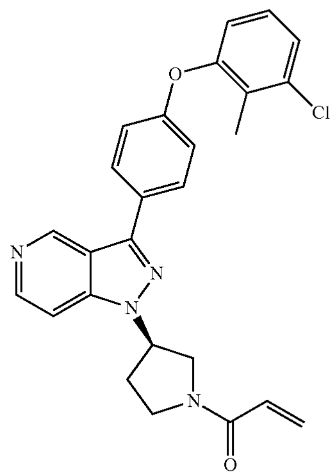 [SMILES: C=CC(=O)N1CC[C@@H](n2nc(-c3ccc(Oc4cccc(Cl)c4C)cc3)c3cnccc32)C1] | 459.15/ 459.2 | (R)-1-(3-(3-(4-(3-chloro-2-methylphenoxy)phenyl)-1H-pyrazolo[4,3-c]pyridin-1-yl)pyrrolidin-1-yl)prop-2-en-1-one |
| 61 | 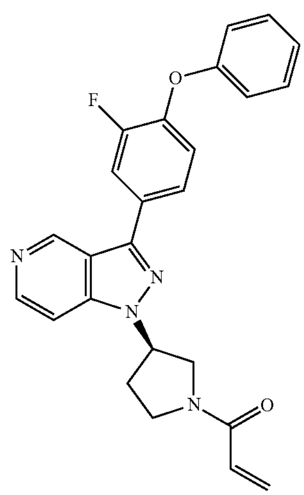 [SMILES: C=CC(=O)N1CC[C@@H](n2nc(-c3ccc(Oc4ccccc4)c(F)c3)c3cnccc32)C1] | 429.16/ 429.2 | (R)-1-(3-(3-(3-fluoro-4-phenoxyphenyl)-1H-pyrazolo[4,3-c]pyridin-1-yl)pyrrolidin-1-yl)prop-2-en-1-one |
| 62 | 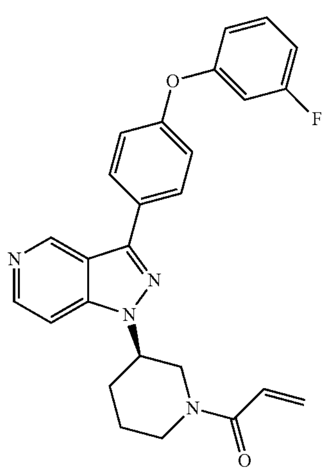 [SMILES: C=CC(=O)N1CCC[C@@H](n2nc(-c3ccc(Oc4cccc(F)c4)cc3)c3cnccc32)C1] | 443.18/ 443.2 | (R)-1-(3-(3-(4-(3-fluorophenoxy)phenyl)-1H-pyrazolo[4,3-c]pyridin-1-yl)piperidin-1-yl)prop-2-en-1-one |

| Entry | Structure | MS(cald) [M + H]+/ MS (found) | Name |
|---|---|---|---|
| 63 | 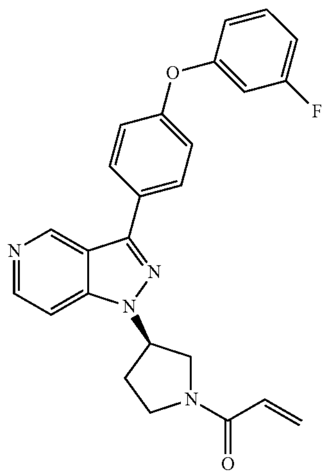 [SMILES: C=CC(=O)N1CC[C@@H](n2nc(-c3ccc(Oc4cccc(F)c4)cc3)c3cnccc32)C1] | 429.16/ 429.2 | (R)-1-(3-(3-(4-(3-fluorophenoxy)phenyl)-1H-pyrazolo[4,3-c]pyridin-1-yl)pyrrolidin-1-yl)prop-2-en-1-one |
| 64 | 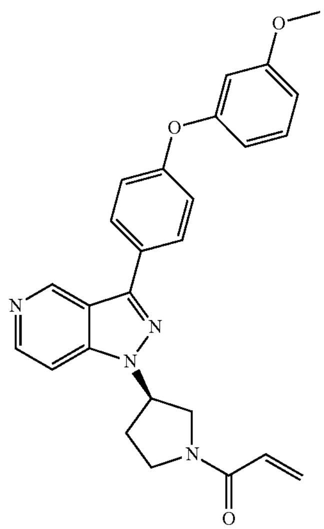 [SMILES: C=CC(=O)N1CC[C@@H](n2nc(-c3ccc(Oc4cccc(OC)c4)cc3)c3cnccc32)C1] | 441.18/ 441.2 | (R)-1-(3-(3-(4-(3-methoxyphenoxy)phenyl)-1H-pyrazolo[4,3-c]pyridin-1-yl)pyrrolidin-1-yl)prop-2-en-1-one |
| 65 | 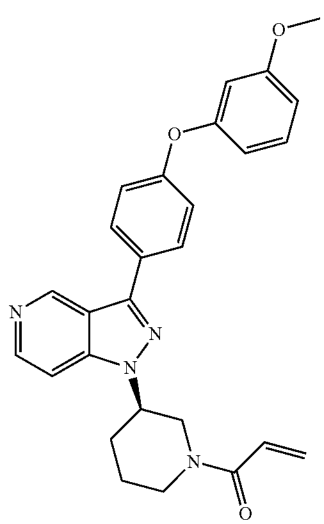 [SMILES: C=CC(=O)N1CCC[C@@H](n2nc(-c3ccc(Oc4cccc(OC)c4)cc3)c3cnccc32)C1] | 455.20/ 455.2 | (R)-1-(3-(3-(4-(3-methoxyphenoxy)phenyl)-1H-pyrazolo[4,3-c]pyridin-1-yl)piperidin-1-yl)prop-2-en-1-one |

-continued

| Entry | Structure | MS(cald) [M + H]+/ MS (found) | Name |
| --- | --- | --- | --- |
| 66 | 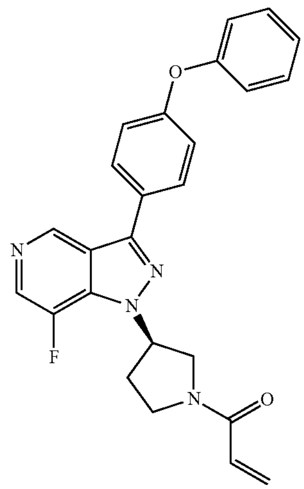 [SMILES: C=CC(=O)N1CC[C@@H](n2nc(-c3ccc(Oc4ccccc4)cc3)c3cncc(F)c32)C1] | 429.46/ 429.1 | ((R)-1-(3-(7-fluoro-3-(4-phenoxyphenyl)-1H-pyrazolo[4,3-c]pyridin-1-yl)pyrrolidin-1-yl)prop-2-en-1-one |
| 67 | 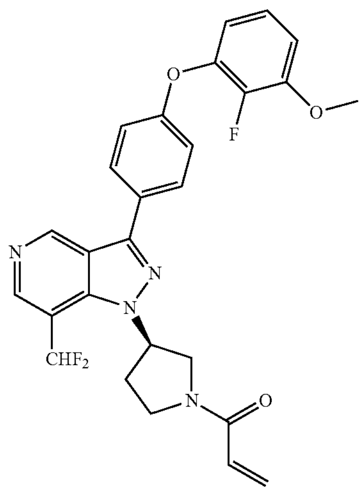 [SMILES: C=CC(=O)N1CC[C@@H](n2nc(-c3ccc(Oc4cccc(OC)c4F)cc3)c3cncc(C(F)F)c32)C1] | 509.49/ 509.1 | (R)-1-(3-(7-(difluoromethyl)-3-(4-(2-fluoro-3-melhoxyphenoxy)phenyl)-1H-pyrazolo[4,3-c]pyridin-1-yl)pyrrolidin-1-yl)prop-2-en-1-one |
| 68 | 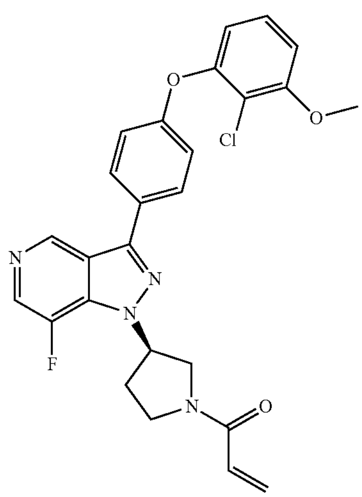 [SMILES: C=CC(=O)N1CC[C@@H](n2nc(-c3ccc(Oc4cccc(OC)c4Cl)cc3)c3cncc(F)c32)C1] | 493.93/ 493.2 | (R)-1-(3-(3-(4-(2-chloro-3-methoxyphenoxy)phenyl)-7-fluoro-1H-pyrazolo[4,3-c]pyridin-1-yl)pyrrolidin-1-yl)prop-2-en-1-one |

| Entry | Structure | MS(cald) [M + H]+/ MS (found) | Name |
|---|---|---|---|
| 69 | 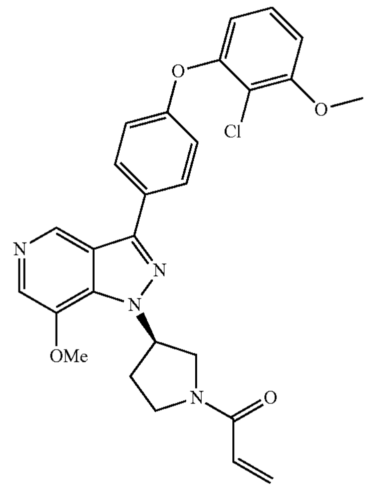 [SMILES: C=CC(=O)N1CC[C@@H](n2nc(-c3ccc(Oc4cccc(OC)c4Cl)cc3)c3cncc(OC)c32)C1] | 505.96/ 505.2 | (R)-1-(3-(3-(4-(2-chloro-3-methoxyphenoxy)phenyl)-7-methoxy-1H-pyrazolo[4,3-c]pyridin-1-yl)pyrrolidin-1-yl)prop-2-en-1-one |
| 70 | 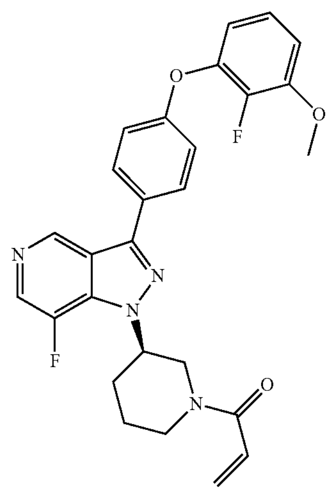 [SMILES: C=CC(=O)N1CCC[C@@H](n2nc(-c3ccc(Oc4cccc(OC)c4F)cc3)c3cncc(F)c32)C1] | 491.5/ 491.1 | (R)-1-(3-(7-fluoro-3-(4-(2-fluoro-3-methoxyphenoxy)phenyl)-1H-pyrazolo[4,3-c]pyridin-1-yl)piperidin-1-yl)prop-2-en-1-one |
| 71 | 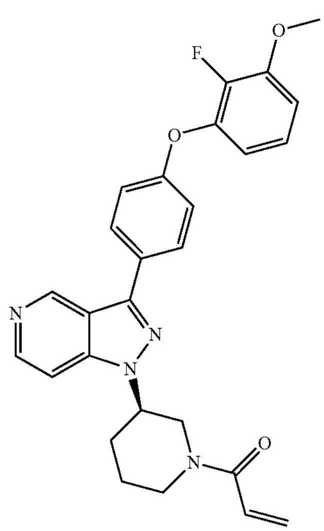 [SMILES: C=CC(=O)N1CCC[C@@H](n2nc(-c3ccc(Oc4cccc(OC)c4F)cc3)c3cnccc32)C1] | 473.19/ 473.2 | (R)-1-(3-(3-(4-(2-fluoro-3-methoxyphenoxy)phenyl)-1H-pyrazolo[4,3-c]pyridin-1-yl)piperidin-1-yl)prop-2-en-1-one |

| Entry | Structure | MS(cald) [M + H]+/MS (found) | Name |
|---|---|---|---|
| 72 | 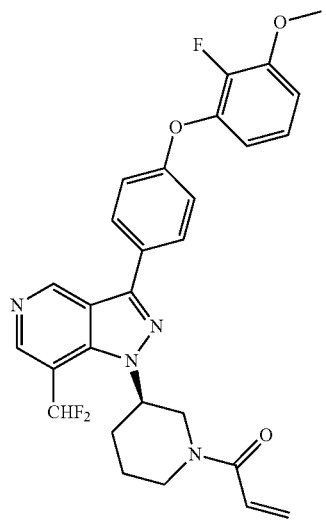 [SMILES: C=CC(=O)N1CCC[C@@H](n2nc(-c3ccc(Oc4cccc(OC)c4F)cc3)c3cncc(C(F)F)c32)C1] | 523.52/523.2 | (R)-1-(3-(7-(difluoromethyl)-3-(4-(2-fluoro-3-methoxyphenoxy)phenyl)-1H-pyrazolo[4,3-c]pyridin-1-yl)piperidin-1-yl)prop-2-en-1-one |
| 73 | 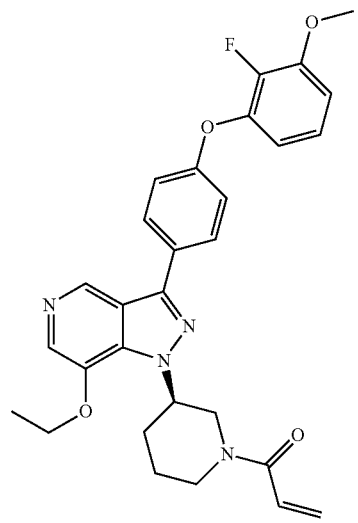 [SMILES: C=CC(=O)N1CCC[C@@H](n2nc(-c3ccc(Oc4cccc(OC)c4F)cc3)c3cncc(OCC)c32)C1] | 517.56/517.2 | (R)-1-(3-(7-ethoxy-3-(4-(2-fluoro-3-methoxyphenoxy)phenyl)-1H-pyrazolo[4,3-c]pyridin-1-yl)piperidin-1-yl)prop-2-en-1-one |
| 74 | 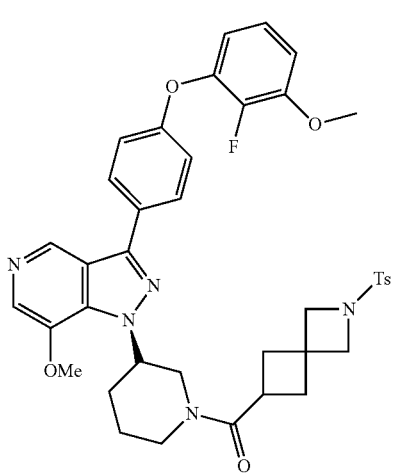 | 726.83/726.3 | (R)-(3-(3-(4-(2-fluoro-3-methoxyphenoxy)phenyl)-7-methoxy-1H-pyrazolo[4,3-c]pyridin-1-yl)piperidin-1-yl)(2-tosyl-2-azaspiro[3.3]heptan-6-yl)methanone |

| Entry | Structure | MS(cald) [M + H]+/ MS (found) | Name |
|---|---|---|---|
| 75 | 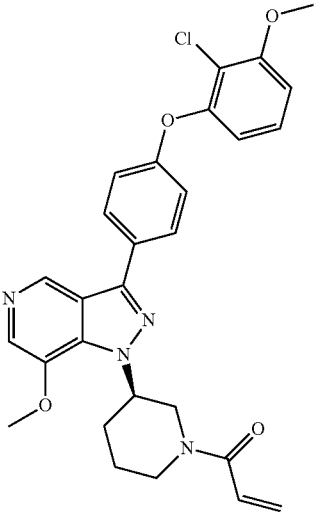 [SMILES: C=CC(=O)N1CCC[C@@H](n2nc(-c3ccc(Oc4cccc(OC)c4Cl)cc3)c3cncc(OC)c32)C1] | 519.99/ 520.1 | (R)-1-(3-(3-(4-(2-chloro-3-methoxyphenoxy)phenyl)-7-methoxy-1H-pyrazolo[4,3-c]pyridin-1-yl)piperidin-1-yl)prop-2-en-1-one |
| 76 | 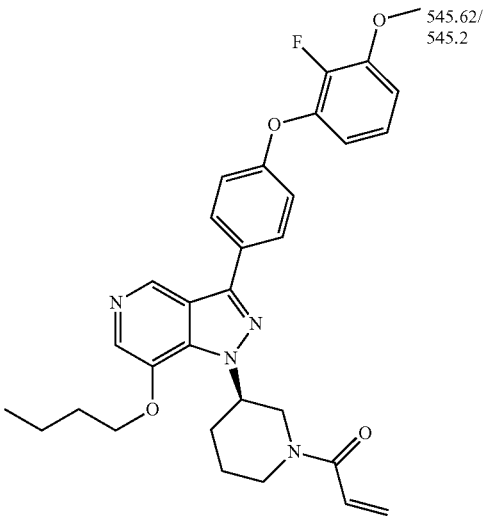 | 545.62/ 545.2 | (R)-1-(3-(7-butoxy-3-(4-(2-fluoro-3-methoxyphenoxy)phenyl)-1H-pyrazolo[4,3-c]pyridin-1-yl)piperidin-1-yl)prop-2-en-1-one |
| 77 | 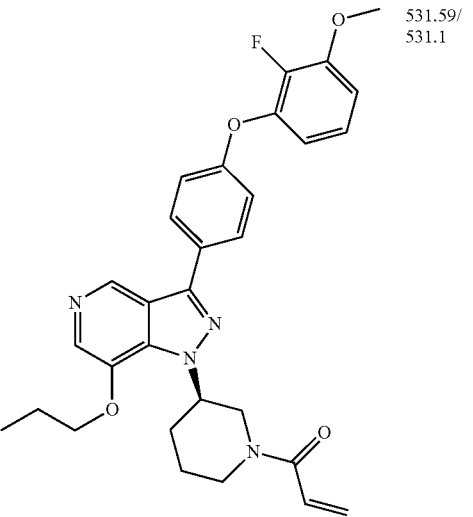 | 531.59/ 531.1 | (R)-1-(3-(3-(4-(2-fluoro-3-methoxyphenoxy)phenyl)-7-propoxy-1H-pyrazolo[4,3-c]pyridin-1-yl)piperidin-1-yl)prop-2-en-1-one |

| Entry | Structure | MS(cald) [M + H]+/ MS (found) | Name |
|---|---|---|---|
| 78 | 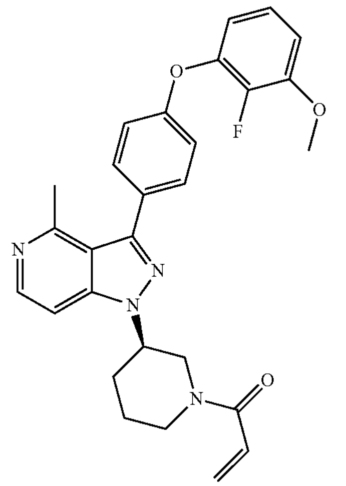 [SMILES: C=CC(=O)N1CCC[C@@H](n2nc(-c3ccc(Oc4cccc(OC)c4F)cc3)c3c(C)nccc32)C1] | 487.54/ 487.1 | (R)-1-(3-(3-(4-(2-fluoro-3-methoxyphenoxy)phenyl)-4-methyl-1H-pyrazolo[4,3-c]pyridin-1-yl)piperidin-1-yl)prop-2-en-1-one |
| 79 | 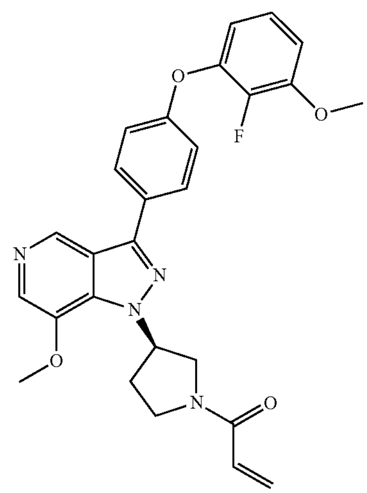 [SMILES: C=CC(=O)N1CC[C@@H](n2nc(-c3ccc(Oc4cccc(OC)c4F)cc3)c3cncc(OC)c32)C1] | 489.51/ 489.2 | (R)-1-(3-(3-(4-(2-fluoro-3-methoxyphenoxy)phenyl)-7-methoxy-1H-pyrazolo[4,3-c]pyridin-1-yl)pyrrolidin-1-yl)prop-2-en-1-one |
| 80 | 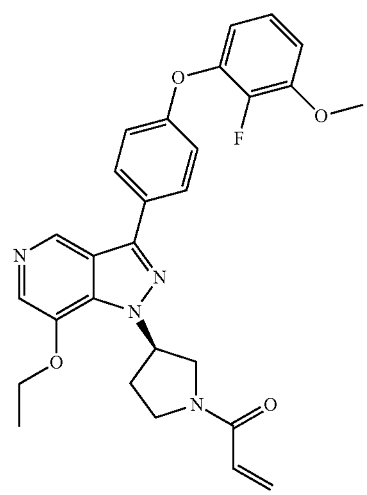 [SMILES: C=CC(=O)N1CC[C@@H](n2nc(-c3ccc(Oc4cccc(OC)c4F)cc3)c3cncc(OCC)c32)C1] | 503.54/ 503.2 | (R)-1-(3-(7-ethoxy-3-(4-(2-fluoro-3-methoxyphenoxy)phenyl)-1H-pyrazolo[4,3-c]pyridin-1-yl)pyrrolidin-1-yl)prop-2-en-1-one |

| Entry | Structure | MS(cald) [M + H]+/ MS (found) | Name |
|---|---|---|---|
| 81 | 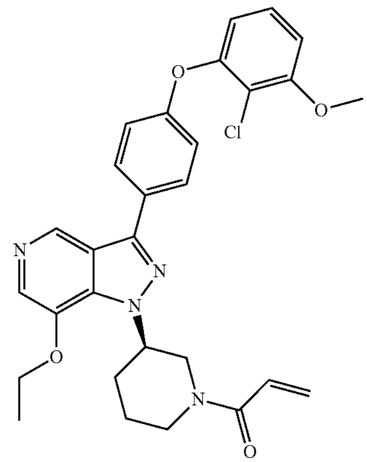 [SMILES: C=CC(=O)N1CCC[C@@H](n2nc(-c3ccc(Oc4cccc(OC)c4Cl)cc3)c3cncc(OCC)c32)C1] | 534.01/ 534.1 | (R)-1-(3-(3-(4-(2-chloro-3-methoxyphenoxy)phenyl)-7-ethoxy-1H-pyrazolo[4,3-c]pyridin-1-yl)piperidin-1-yl)prop-2-en-1-one |
| 82 | 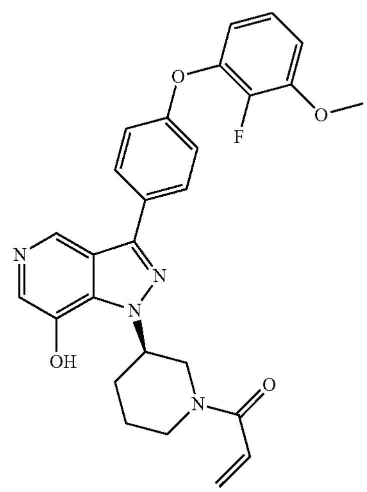 [SMILES: C=CC(=O)N1CCC[C@@H](n2nc(-c3ccc(Oc4cccc(OC)c4F)cc3)c3cncc(O)c32)C1] | 489.51/ 489.2 | (R)-1-(3-(3-(4-(2-fluoro-3-methoxyphenoxy)phenyl)-7-hydroxy-1H-pyrazolo[4,3-c]pyridin-1-yl)piperidin-1-yl)prop-2-en-1-one |
| 83 | 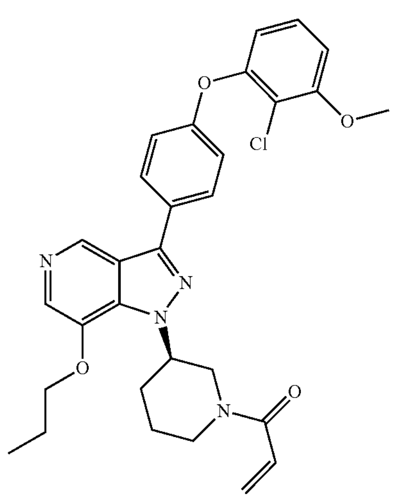 [SMILES: C=CC(=O)N1CCC[C@@H](n2nc(-c3ccc(Oc4cccc(OC)c4Cl)cc3)c3cncc(OCCC)c32)C1] | 548.04/ 548.1 | (R)-1-(3-(3-(4-(2-chloro-3-methoxyphenoxy)phenyl)-7-propoxy-1H-pyrazolo[4,3-c]pyridin-1-yl)piperidin-1-yl)prop-2-en-1-one |

-continued

| Entry | Structure | MS(cald) [M + H]+/ MS (found) | Name |
|---|---|---|---|
| 84 | 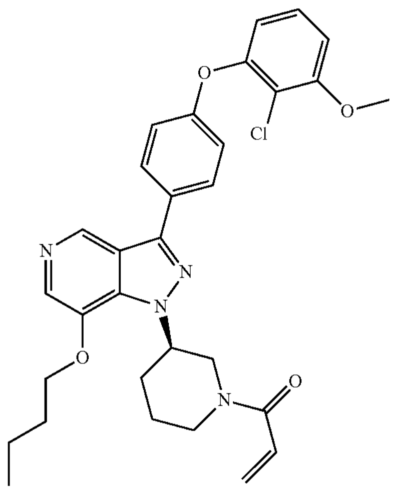 [SMILES: C=CC(=O)N1CCC[C@@H](n2nc(-c3ccc(Oc4cccc(OC)c4Cl)cc3)c3cncc(OCCCC)c32)C1] | 562.07/ 562.0 | (R)-1-(3-(7-butoxy-3-(4-(2-chloro-3-methoxyphenoxy)phenyl)-1H-pyrazolo[4,3-c]pyridin-1-yl)piperidin-1-yl)prop-2-en-1-one |
| 85 | 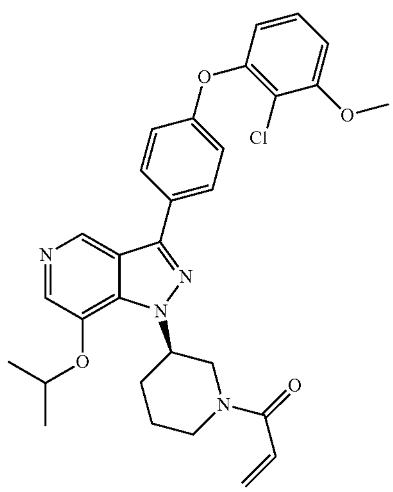 [SMILES: C=CC(=O)N1CCC[C@@H](n2nc(-c3ccc(Oc4cccc(OC)c4Cl)cc3)c3cncc(OC(C)C)c32)C1] | 548.04/ 548.1 | (R)-1-(3-(3-(4-(2-chloro-3-methoxyphenoxy)phenyl)-7-isopropoxy-1H-pyrazolo[4,3-c]pyridin-1-yl)piperidin-1-yl)prop-2-en-1-one |
| 86 | 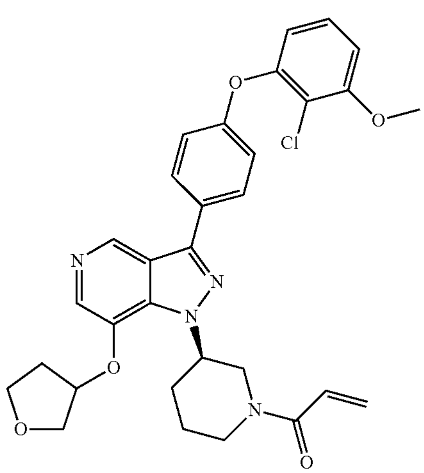 [SMILES: C=CC(=O)N1CCC[C@@H](n2nc(-c3ccc(Oc4cccc(OC)c4Cl)cc3)c3cncc(OC4CCOC4)c32)C1] | 576.05/ 576.0 | 1-((3R)-3-(3-(4-(2-chloro-3-methoxyphenoxy)phenyl)-7-((tetrahydrofuran-3-yl)oxy)-1H-pyrazolo[4,3-c]pyridin-1-yl)piperidin-1-yl)prop-2-en-1-one |

-continued

| Entry | Structure | MS(cald) [M + H]+/ MS (found) | Name |
|---|---|---|---|
| 87 | 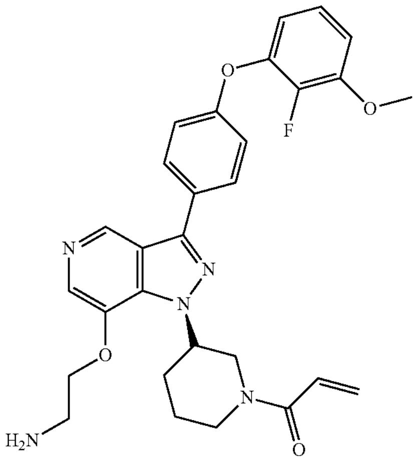 | 532.58/ 532.1 | (R)-1-(3-(7-(2-aminoethoxy)-3-(4-(2-fluoro-3-methoxyphenoxy)phenyl)-1H-pyrazolo[4,3-c]pyridin-1-yl)piperidin-1-yl)prop-2-en-1-one |
| 88 | 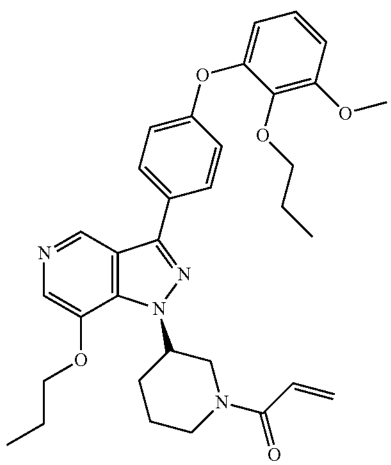 | 571.68/ 571.2 | (R)-1-(3-(3-(4-(3-methoxy-2-propoxyphenoxy)phenyl)-7-propoxy-1H-pyrazolo[4,3-c]pyridin-1-yl)piperidin-1-yl)prop-2-en-1-one |
| 89 | 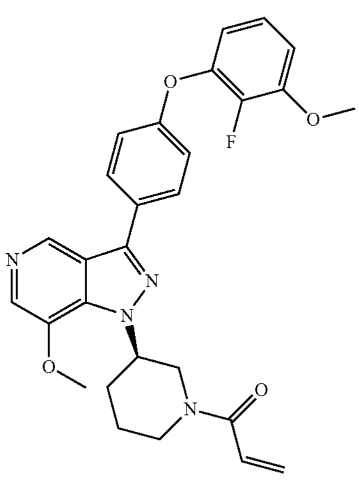 [SMILES: C=CC(=O)N1CCC[C@@H](n2nc(-c3ccc(Oc4cccc(OC)c4F)cc3)c3cncc(OC)c32)C1] | 505.55/ 505.1 | (R)-1-(3-(3-(4-(2-fluoro-3-methoxyphenoxy)phenyl)-7-methoxy-1H-pyrazolo[4,3-c]pyridin-1-yl)piperidin-1-yl)propan-1-one |

| Entry | Structure | MS(cald) [M + H]+/ MS (found) | Name |
|---|---|---|---|
| 90 | 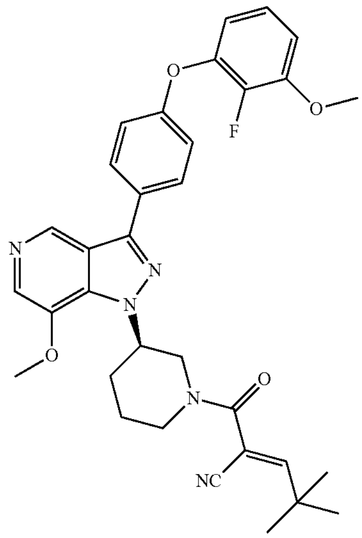 [SMILES: COc1cccc(Oc2ccc(-c3nn([C@@H]4CCCN(C(=O)/C(C#N)=C/C(C)(C)C)C4)c4c(OC)cncc34)cc2)c1F] | 584.65/ 584.2 | (R,E)-2-(3-(3-(4-(2-fluoro-3-methoxyphenoxy)phenyl)-7-methoxy-1H-pyrazolo[4,3-c]pyridin-1-yl) piperidine-1-carbonyl)-4,4-dimethylpent-2-enenitrile |
| 91 | 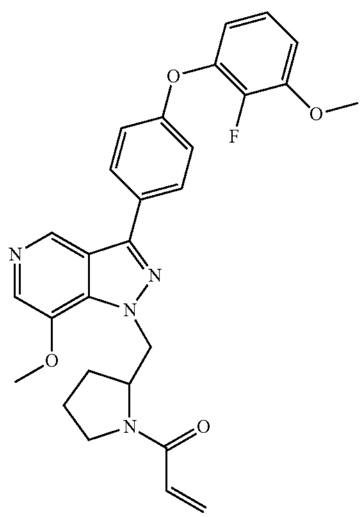 [SMILES: C=CC(=O)N1CCCC1Cn1nc(-c2ccc(Oc3cccc(OC)c3F)cc2)c2cncc(OC)c21] | 503.54/ 503.3 | 1-(2-((3-(4-(2-fluoro-3-methoxyphenoxy)phenyl)-7-methoxy-1H-pyrazolo[4,3-c]pyridin-1-yl)methyl)pyrrolidin-1-yl)prop-2-en-1-one |
| 92 | 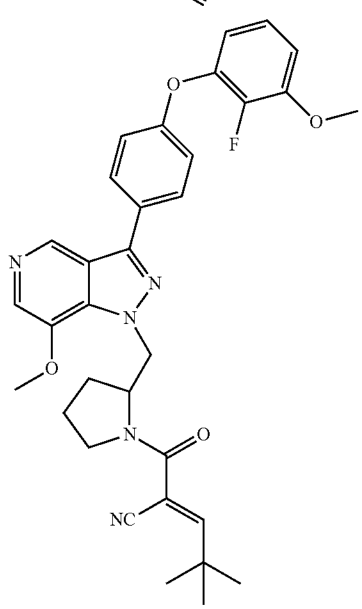 | 584.65/ 584.3 | (E)-2-(2-((3-(4-(2-fluoro-3-methoxyphenoxy)phenyl)-7-methoxy-1H-pyrazolo[4,3-c]pyridin-1-yl)methyl)pyrrolidine-1-carbonyl)-4,4-dimethylpent-2-enenitrile |

| Entry | Structure | MS(cald) [M + H]+/ MS (found) | Name |
|---|---|---|---|
| 93 | 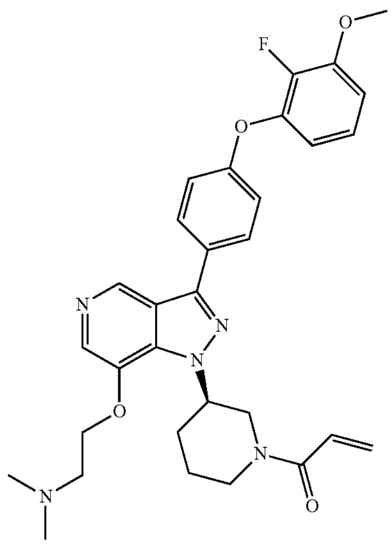 | 560.63/ 560.2 | (R)-1-(3-(7-(2-(dimethylamino)ethoxy)-3-(4-(2-fluoro-3-methoxyphenoxy) phenyl)-1H-pyrazolo[4,3-c]pyridin-1-yl)piperidin-1-yl)prop-2-en-1-one |
| 94 | 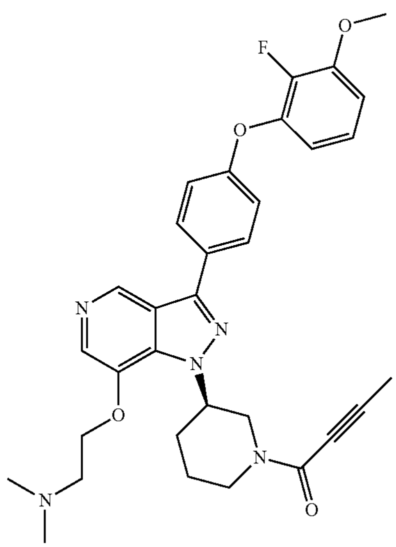 [SMILES: CC#CC(=O)N1CCC[C@@H](n2nc(-c3ccc(Oc4cccc(OC)c4F)cc3)c3cncc(OCCN(C)C)c32)C1] | 572.64/ 572.1 | (R)-1-(3-(7-(2-(dimethylamino)ethoxy)-3-(4-(2-fluoro-3-methoxyphenoxy) phenyl)-1H-pyrazolo[4,3-c]pyridin-1-yl)piperidin-1-yl)but-2-yn-1-one |
| 95 | 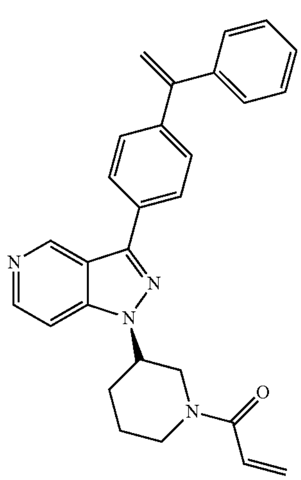 | 435.53/ 435.1 | (S)-1-(3-(3-(4-(1-phenylvinyl)phenyl)-1H-pyrazolo [4,3-c]pyridin-1-yl)piperidin-1-yl)prop-2-en-1-one |

-continued

| Entry | Structure | MS(cald) [M + H]+/ MS (found) | Name |
|---|---|---|---|
| 96 | 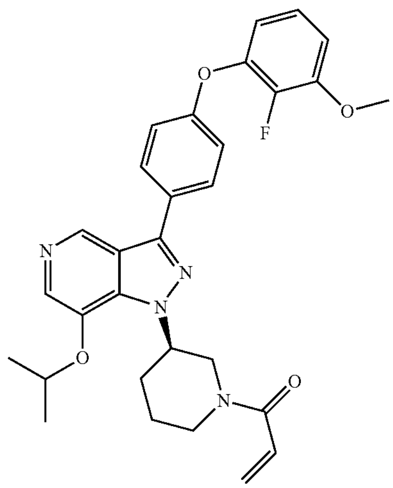 | 531.59/ 531.1 | (R)-1-(3-(3-(4-(2-fluoro-3-methoxyphenoxy)phenyl)-7-isopropoxy-1H-pyrazolo[4,3-c]pyridin-1-yl)piperidin-1-yl)prop-2-en-1-one |
| 97 | 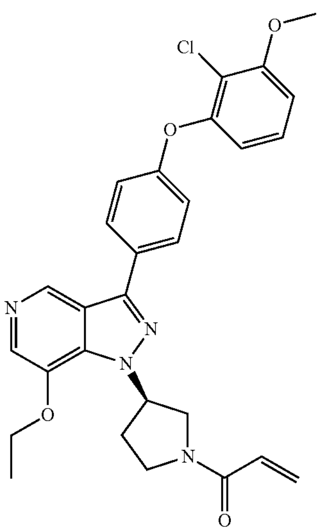 [SMILES: C=CC(=O)N1CC[C@@H](n2nc(-c3ccc(Oc4cccc(OC)c4Cl)cc3)c3cncc(OCC)c32)C1] | 519.99/ 520.0 | (R)-1-(3-(3-(4-(2-chloro-3-methoxyphenoxy)phenyl)-7-ethoxy-1H-pyrazolo[4,3-c]pyridin-1-yl)pyrrolidin-1-yl)prop-2-en-1-one |
| 98 | 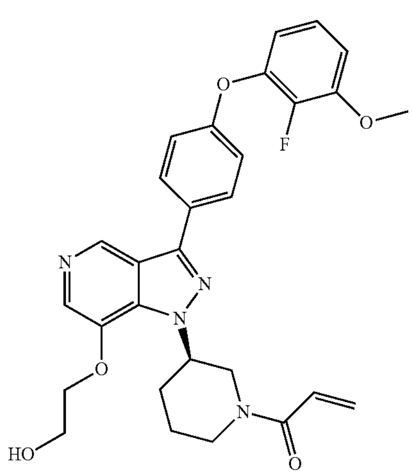 [SMILES: C=CC(=O)N1CCC[C@@H](n2nc(-c3ccc(Oc4cccc(OC)c4F)cc3)c3cncc(OCCO)c32)C1] | 533.56/ 533.1 | (R)-1-(3-(3-(4-(2-fluoro-3-methoxyphenoxy)phenyl)-7-(2-hydroxyethoxy) 1H-pyrazolo[4,3-c]pyridin-1-yl)piperidin-1-yl)prop-2-en-1-one |

| Entry | Structure | MS(cald) [M + H]+/ MS (found) | Name |
|---|---|---|---|
| 99 | 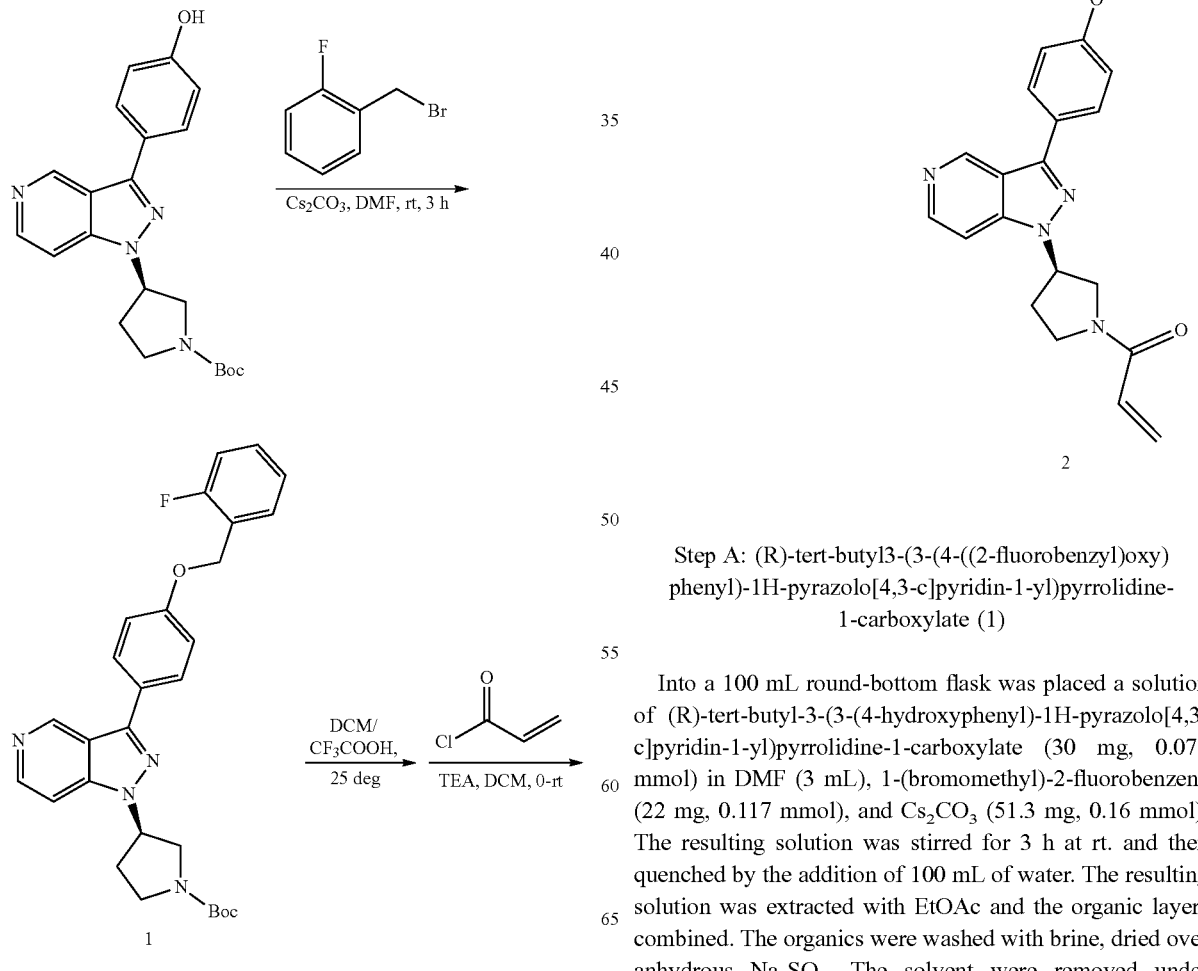 | 559.6/ 559.3 | 1-((3R)-3-(3-(4-(2-fluoro-3-methoxyphenoxy)phenyl)-7-((tetrahydrofuran-3-yl)oxy)-1H-pyrazolo[4,3-c]pyridin-1-yl)piperidin-1-yl)prop-2-en-1-one |

Example 100: (R)-1-(3-(3-(4-((2-fluorobenzyl)oxy)phenyl)-1H-pyrazolo[4,3-c]pyridin-1-yl)pyrrolidin-1-yl)prop-2-en-1-one Step A: (R)-tert-butyl3-(3-(4-((2-fluorobenzyl)oxy)phenyl)-1H-pyrazolo[4,3-c]pyridin-1-yl)pyrrolidine-1-carboxylate (1)

Into a 100 mL round-bottom flask was placed a solution of (R)-tert-butyl-3-(3-(4-hydroxyphenyl)-1H-pyrazolo[4,3-c]pyridin-1-yl)pyrrolidine-1-carboxylate (30 mg, 0.078 mmol) in DMF (3 mL), 1-(bromomethyl)-2-fluorobenzene (22 mg, 0.117 mmol), and Cs$_2$CO$_3$ (51.3 mg, 0.16 mmol). The resulting solution was stirred for 3 h at rt. and then quenched by the addition of 100 mL of water. The resulting solution was extracted with EtOAc and the organic layers combined. The organics were washed with brine, dried over anhydrous Na$_2$SO$_4$, The solvent were removed under vacuum and the residue was purified by column chromatography on silica gel (gradient: DCM/MeOH=200:1-100:1) to give the title product (30 mg, yield 80%). LCMS: m/z=489.2 [M+H]+.

Step B: (R)-1-(3-(3-(4-((2-fluorobenzyl)oxy)phenyl)-1H-pyrazolo[4,3-c]pyridin-1-yl) pyrrolidin-1-yl)prop-2-en-1-one (2)

((R)-tert-butyl 3-(3-(4-(2-fluoro-3-methoxyphenoxy)phenyl)-7-methyl-1H-pyrazolo[4,3-c]pyridin-1-yl)pyrrolidine-1-carboxylate (30 mg, 0.061 mmol) were added to CF₃COOH/DCM=4/1 (5 mL) in one portion. The mixture was stirred for about 1 h at rt. Volatile components were removed under vacuum to give the title product of crude product (24 mg), and directly used in next step without further purification. LCMS: m/z=389.2 [M+H]+.

A solution of Acryloyl chloride (5.5 mg, 0.061 mmol) in DCM (1 mL) was added to a stirred solution of (R)-3-(4-((2-fluorobenzyl)oxy)phenyl)-1-(pyrrolidin-3-yl)-1H-pyrazolo[4,3-c]pyridine (24 mg, 0.061 mmol) and TEA (44 mg, 0.43 mmol) in DCM (5 mL) at 0° C. The reaction mixture was stirred for 1 h, poured onto brine and extracted with DCM. The organic layer was dried, concentrated and recrystallized from DCM/MeOH=100/1 to give the title product (13 mg, yield 50%). ¹H-NMR (400 MHz, CDCl₃): δ 9.18 (br, 1H), 8.48 (br, 1H), 7.93-7.89 (m, 2H), 7.55-7.52 (m, 1H), 7.34-7.26 (m, 2H), 7.20-7.09 (m, 4H), 6.52-6.40 (m, 2H), 5.75-5.70 (m, 1H), 5.27-5.23 (m, 1H), 5.22 (s, 1H), 4.16-4.07 (m, 3H), 3.82-3.80 (m, 1H), 2.89-2.49 (m, 2H). LCMS: m/z=443.2 [M+H]+.

The following additional Example 101, 102 shown in the Table below were prepared following the procedures outlined in the general methods above and detailed in Example 100.

| Entry | Structure | MS(cald) [M + H]+/MS (found) | Name |
|---|---|---|---|
| 101 | 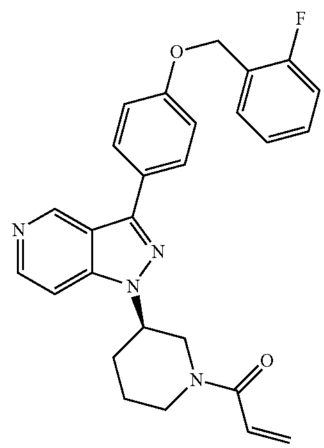 [SMILES: C=CC(=O)N1CCC[C@@H](n2nc(-c3ccc(OCc4ccccc4F)cc3)c3cnccc32)C1] | 457.20/457.2 | (R)-1-(3-(3-(4-((2-fluorobenzyl)oxy)phenyl)-1H-pyrazolo[4,3-c]pyridin-1-yl)piperidin-1-yl)prop-2-en-1-one |
| 102 | 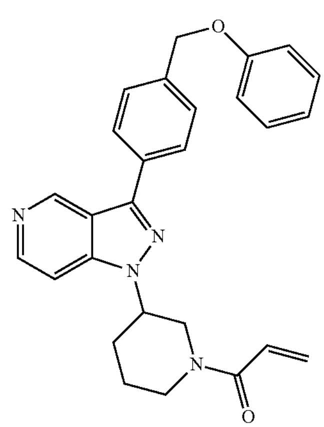 [SMILES: C=CC(=O)N1CCCC(n2nc(-c3ccc(COc4ccccc4)cc3)c3cnccc32)C1] | 438.52/438.00 | (R)-1-(3-(3-(4-(phenoxymethyl)phenyl)-1H-indazol-1-yl)piperidin-1-yl)prop-2-en-1-one |

Example 103: (R)-4-(1-(1-acryloylpyrrolidin-3-yl)-1H-pyrazolo[4,3-c]pyridin-3-yl)-N-(3-methoxybenzyl)benzamide

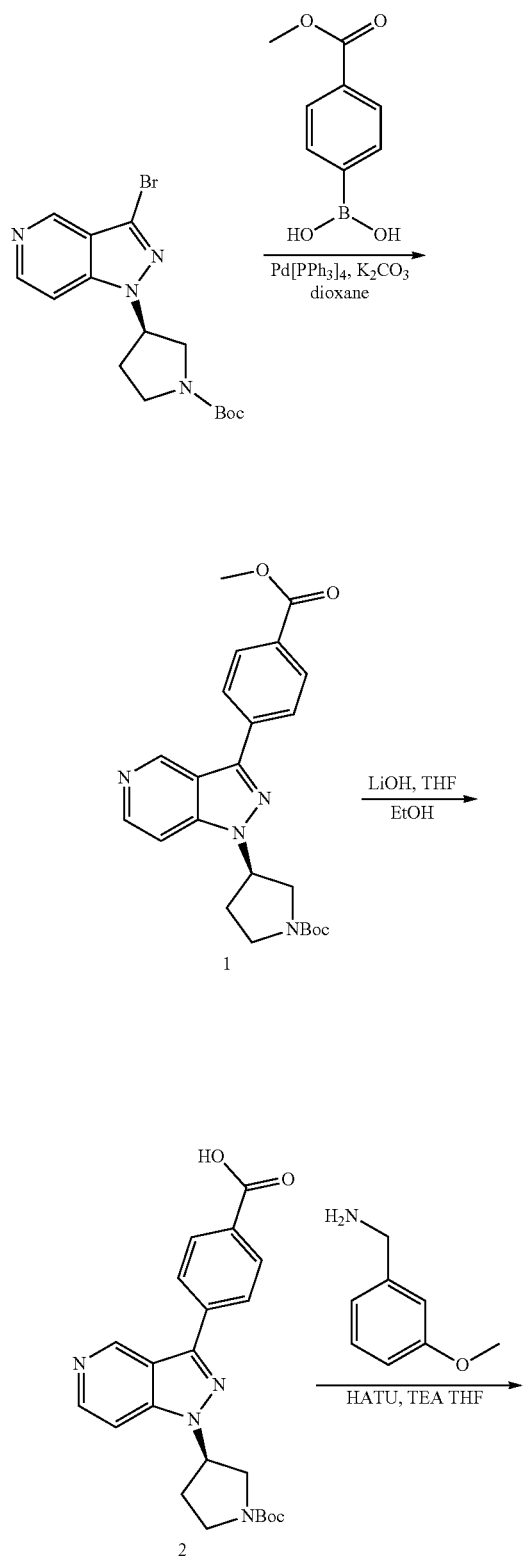

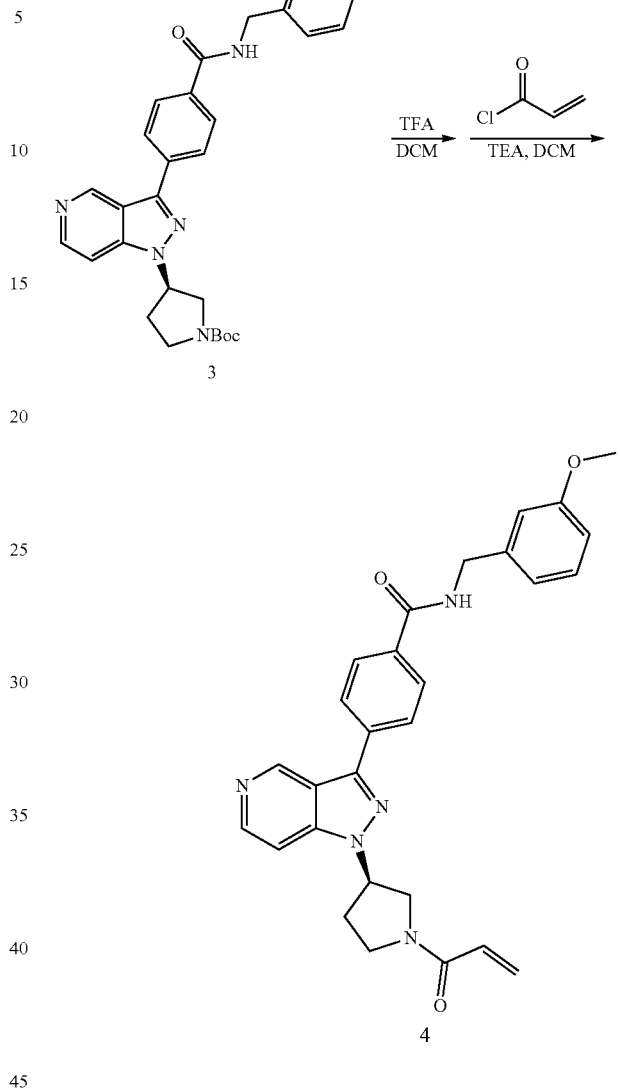

Step A: (R)-tert-butyl 3-(3-(4-(methoxycarbonyl)phenyl)-1H-pyrazolo[4,3-c]pyridin-1-yl)pyrrolidine-1-carboxylate (1)

To a solution of (R)-tert-butyl 3-(3-bromo-1H-pyrazolo[4,3-c]pyridin-1-yl)pyrrolidine-1-carboxylate (105 mg, 0.286 mmol, 1.0 eq) and (4-(methoxycarbonyl)phenyl)boronic acid (77 mg, 0.429 mmol, 1.5 eq) in dioxane (8.0 mL) and water (1.0 mL), was added $K_2CO_3$ (79 mg, 0.572 mmol, 2.0 eq) and $(Ph_3P)_4Pd$ (20 mg) under $N_2$ with stirring. The mixture was refluxed for 5.5 h until the material was disappeared. The reaction mixture was cooled to room temperature. The dioxane was removed by rotary evaporation. The residue was poured into water and extracted with EA. The organic layer was dried over $Na_2SO_4$, filtered and the solvent was removed by vacuum and the residue was purified with flash silica gel chromatography (DCM:MeOH=100:1-50:1) to give the title product (90 mg, yield 77.4%). ¹H-NMR (400 MHz, CDCl₃): δ 9.45 (s, 1H), 8.53 (s, 1H), 8.19 (d, J=8.4 Hz, 2H), 8.04-8.11 (m, 3H), 5.20 (s, 1H), 3.97 (s, 3H), 3.93 (s, 3H), 3.61 (s, 1H), 2.62-2.66 (m, 1H), 2.46 (d, J=6.0 Hz, 1H), 1.48 (s, 9H). LCMS: m/z=423 [M+H]⁺.

Step B: (R)-4-(1-(1-(tert-butoxycarbonyl)pyrrolidin-3-yl)-1H-pyrazolo[4,3-c]pyridin-3-yl)benzoic acid (2)

To a solution of 1 (90 mg, 0.213 mmol, 1.0 eq) in THF (5.0 mL) and EtOH (5.0 mL), LiOH (45 mg, 1.067 mmol, 5.0 eq) was added. The mixture was stirred at room temperature until the start material disappeared, added water, then 1 N HCl was added to adjust to pH=5.0, then the mixture was extracted with EA, The organic layer was washed with water and brine, dried with anhydrous Na₂SO₄, filtered and concentrated give the title crude product 2 (75 mg, 86.2%) used next step without purification. LCMS: m/z=409 [M+H]⁺.

Step C: (R)-tert-butyl 3-(3-(4-((3-methoxybenzyl)carbamoyl)phenyl)-1H-pyrazolo[4,3-c]pyridin-1-yl)pyrrolidine-1-carboxylate (3)

Into a 50 mL round-bottom flask, was placed a solution of 2 (75 mg, 0.184 mmol, 1.0 eq) in THF (5.0 mL), (3-methoxyphenyl)methanamine (38 mg, 0.276 mmol, 1.5 eq), and TEA (47 mg, 0.460 mmol, 2.5 eq), HATU (84 mg, 0.221 mmol, 1.2 eq). The resulting solution was stirred for 1.5 h at room temperature. The reaction mixture was quenched with 30 mL water. The resulting solution was extracted with EA (20 mL*3) and the organic layers were combined and washed with brine, dried over anhydrous Na₂SO₄, The solvent were removed under vacuum and the residue was purified by silica gel column chromatography (DCM/MeOH=100:1-50:1) to give the title product (85 mg, yield 87.7%). ¹H-NMR (400 MHz, CDCl₃): δ 9.37 (s, 1H), 8.48 (s, 1H), 8.07 (d, J=7.6 Hz, 1H), 7.94 (d, J=7.6 Hz, 1H), 7.38 (s, 1H), 7.26-7.32 (m, 1H), 6.94-6.99 (m, 2H), 6.86 (d, J=8.4 Hz, 1H), 6.48 (s, 1H), 5.19 (s, 1H), 4.67 (d, J=5.2 Hz, 2H), 3.78-3.93 (m, 6H), 3.60 (s, 1H), 2.64 (d, J=6.0 Hz, 1H), 2.46 (d, J=7.6 Hz, 1H), 1.47 (s, 9H). LCMS: m/z=528 [M+H]⁺.

Step D: (R)-4-(1-(1-acryloylpyrrolidin-3-yl)-1H-pyrazolo[4,3-c]pyridin-3-yl)-N-(3-methoxybenzyl)benzamide (4)

Intermediate 3 (85 mg, 0.157 mmol, 1.0 eq) were dissolved in DCM (8.0 mL), added TFA (1.5 mL) in one portion. The mixture was stirred for about 1.5 h at rt. Volatile components were removed under vacuum to give the title product of crude product TFA salt, and directly used in next step without further purification. The crude product was dissolved in DCM (7.0 mL), added TEA to the solution until PH=8.0, then added Acryloyl chloride (17 mg, 0.188 mmol, 1.2 eq) in DCM (1.0 mL) dropwise to the solution. The reaction mixture was stirred for 0.5 h, poured onto water and extracted with DCM. The organic layer was dried with anhydrous Na₂SO₄, filtered and concentrated, the residue was purified with silica gel plate (DCM/MeOH=50:1) to give the title product (20 mg, yield 25.8%). ¹H-NMR (400 MHz, CD₃OD): δ 9.82 (s, 1H), 8.62 (s, 1H), 8.35 (d, J=6.0 Hz, 1H), 8.18 (d, J=8.0 Hz, 2H), 8.08 (d, J=8.0 Hz, 2H), 7.25-7.29 (m, 1H), 6.97 (d, J=8.0 Hz, 2H), 6.84 (d, J=8.0 Hz, 1H), 6.61-6.79 (m, 1H), 6.32-6.38 (m, 1H), 5.77-5.85 (m, 2H), 4.60 (s, 2H), 4.28 (d, J=4.0 Hz, 1H), 4.00 (d, J=6.8 Hz, 1H), 3.80 (s, 3H), 2.62-2.75 (m, 2H). LCMS: m/z=482.2 [M+H]⁺.

The following additional Example 104-105 shown in the Table below were prepared following the procedures outlined in the general methods above and detailed in Example 103.

| Entry | Structure | MS(cald) [M+ H]⁺/ MS (found) | Name |
|---|---|---|---|
| 104 | 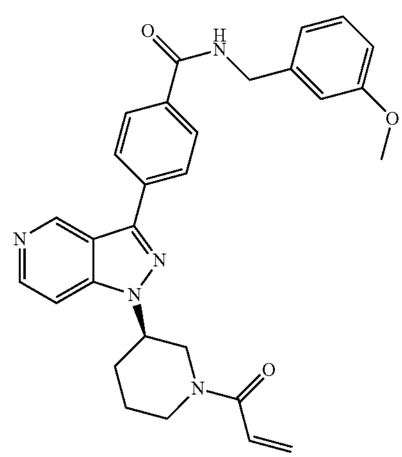 [SMILES: C=CC(=O)N1CCC[C@@H](n2nc(-c3ccc(C(=O)NCc4cccc(OC)c4)cc3)c3cnccc32)C1] | 496.23/ 496.2 | (R)-4-(1-(1-acryloylpiperidin-3-yl)-1H-pyrazolo[4,3-c]pyridin-3-yl)-N-(3-methoxybenzyl)benzamide |

| Entry | Structure | MS(cald) [M+ H]+/ MS (found) | Name |
|---|---|---|---|
| 105 | 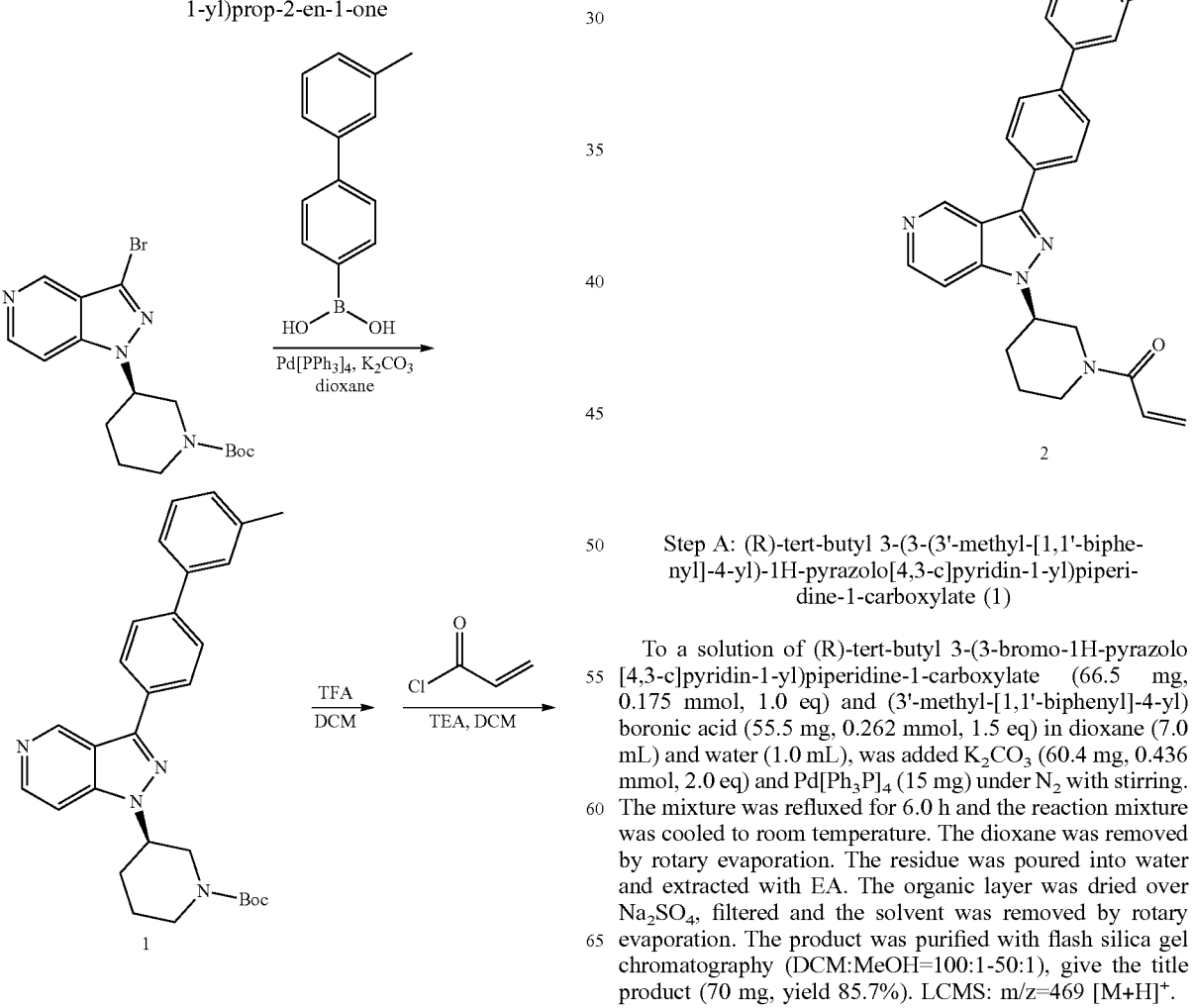 | 465.52/ 465.2 | (R)-4-(1-(1-(but-2-ynoyl)piperidin-3-yl)-1H-pyrazolo[4,3-c]pyridin-3-yl)-N-(pyridin-2-yl)benzamide |

Example 106: (R)-1-(3-(3-(3'-methyl-[1,1'-biphenyl]-4-yl)-1H-pyrazolo[4,3-c]pyridin-1-yl)piperidin-1-yl)prop-2-en-1-one

Step A: (R)-tert-butyl 3-(3-(3'-methyl-[1,1'-biphenyl]-4-yl)-1H-pyrazolo[4,3-c]pyridin-1-yl)piperidine-1-carboxylate (1)

To a solution of (R)-tert-butyl 3-(3-bromo-1H-pyrazolo[4,3-c]pyridin-1-yl)piperidine-1-carboxylate (66.5 mg, 0.175 mmol, 1.0 eq) and (3'-methyl-[1,1'-biphenyl]-4-yl) boronic acid (55.5 mg, 0.262 mmol, 1.5 eq) in dioxane (7.0 mL) and water (1.0 mL), was added K$_2$CO$_3$ (60.4 mg, 0.436 mmol, 2.0 eq) and Pd[Ph$_3$P]$_4$ (15 mg) under N$_2$ with stirring. The mixture was refluxed for 6.0 h and the reaction mixture was cooled to room temperature. The dioxane was removed by rotary evaporation. The residue was poured into water and extracted with EA. The organic layer was dried over Na$_2$SO$_4$, filtered and the solvent was removed by rotary evaporation. The product was purified with flash silica gel chromatography (DCM:MeOH=100:1-50:1), give the title product (70 mg, yield 85.7%). LCMS: m/z=469 [M+H]$^+$.

Step B: (R)-1-(3-(3-(3'-methyl-[1,1'-biphenyl]-4-yl)-1H-pyrazolo[4,3-c]pyridin-1-yl)piperidin-1-yl)prop-2-en-1-one (2)

Intermediate 1 (70 mg, 0.15 mmol, 1.0 eq) were dissolved in DCM (5.0 mL), added TFA (1.0 mL) in one portion. The mixture was stirred for about 1.5 h at rt. Volatile components were removed under vacuum to give the title crude product TFA salt, and directly used in next step without further purification. The crude product was dissolved in DCM (5.0 mL), added TEA until PH=8.0, then added Acryloyl chloride (20 mg, 0.224 mmol, 1.5 eq) in DCM (1.0 mL) dropwise to the solution. The reaction mixture was stirred for 0.5 h, poured onto water and extracted with DCM. The organic layer was dried with anhydrous $Na_2SO_4$, filtered and concentrated, the residue was purified with silica gel plate (DCM/MeOH=50:1) to give the title product (20 mg, yield 31.7%). $^1$H-NMR (400 MHz, $CDCl_3$): δ 9.40 (s, 1H), 8.48 (s, 1H), 8.06 (d, J=8.0 Hz, 2H), 7.76 (d, J=8.4 Hz, 2H), 7.35-7.48 (m, 4H), 7.20 (d, J=7.6 Hz, 1H), 6.56-6.69 (m, 1H), 6.34-6.39 (m, 1H), 5.70-5.78 (m, 1H), 4.95 (d, J=11.2 Hz, 0.5H), 4.66 (d, J=7.2 Hz, 0.5H), 4.50 (d, J=10.4 Hz, 1H), 4.08-4.23 (m, 1H), 3.84 (s, 0.5H), 3.21-3.30 (m, 1H), 2.93 (s, 0.5), 2.30 (d, J=11.2 Hz, 1H), 1.74 (s, 1H). LCMS: m/z=423 [M+H]$^+$.

The following additional Examples 107-115 shown in the Table below were prepared following the procedures outlined in the general methods above and detailed in Examples 106.

| Entry | Structure | MS(cald) [M + H]$^+$/ MS (found) | Name |
|---|---|---|---|
| 107 | 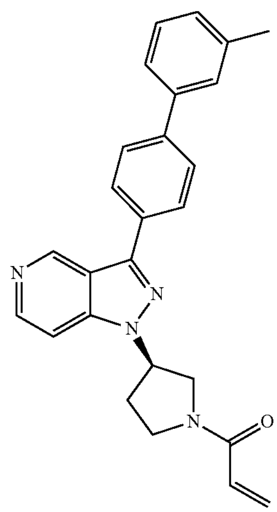 [SMILES: C=CC(=O)N1CC[C@@H](n2nc(-c3ccc(-c4cccc(C)c4)cc3)c3cnccc32)C1] | 409.20/ 409.2 | (R)-1-(3-(3-(3'-methyl-[1,1'-biphenyl]-4-yl)-1H-pyrazolo[4,3-c]pyridin-1-yl)pyrrolidin-1-yl)prop-2-en-1-one |
| 108 | 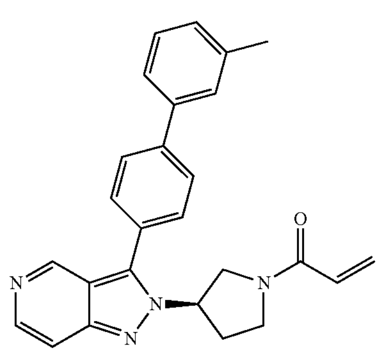 [SMILES: C=CC(=O)N1CC[C@@H](n2nc3ccncc3c2-c2ccc(-c3cccc(C)c3)cc2)C1] | 409.20/ 409.2 | (R)-1-(3-(3-(3'-methyl-[1,1'-biphenyl]-4-yl)-2H-pyrazolo[4,3-c]pyridin-2-yl)pyrrolidin-1-yl)prop-2-en-1-one |

| Entry | Structure | MS(cald) [M + H]+/ MS (found) | Name |
| --- | --- | --- | --- |
| 109 | 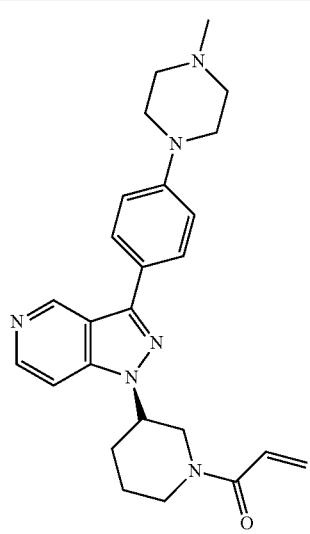 | 431.55/ 431.1 | (R)-1-(3-(3-(4-(4-methylpiperazin-1-yl)phenyl)-1H-pyrazolo[4,3-c]pyridin-1-yl)piperidin-1-yl)prop-2-en-1-one |
| 110 | 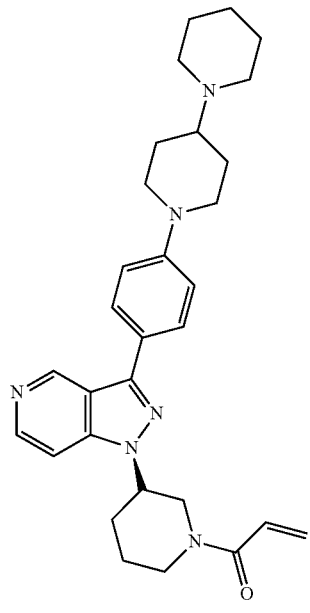 | 499.66/ 499.3 | (R)-1-(3-(3-(4-([1,4'-bipiperidin]-1'-yl)phenyl)-1H-pyrazolo[4,3-c]pyridin-1-yl)piperidin-1-yl)prop-2-en-1-one |

-continued

| Entry | Structure | MS(cald) [M + H]+/ MS (found) | Name |
|---|---|---|---|
| 111 | 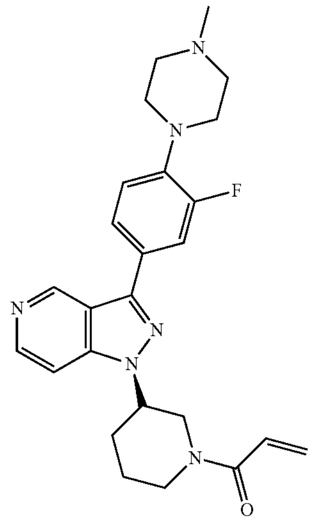 | 449.54/ 449.1 | (R)-1-(3-(3-(3-fluoro-4-(4-methylpiperazin-1-yl)phenyl)-1H-pyrazolo[4,3-c]pyridin-1-yl)piperidin-1-yl)prop-2-en-1-one |
| 112 | 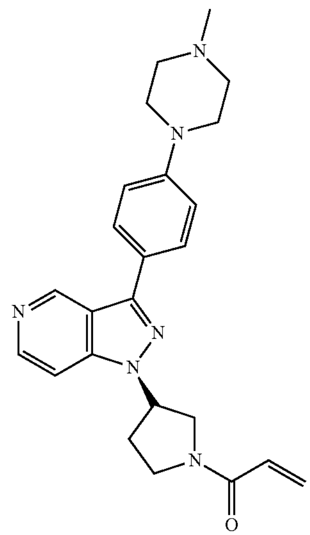 | 417.52/ 417.1 | (R)-1-(3-(3-(4-(4-methylpiperazin-1-yl)phenyl)-1H-pyrazolo[4,3-c]pyridin-1-yl)pyrrolidin-1-yl)prop-2-en-1-one |
| 113 | 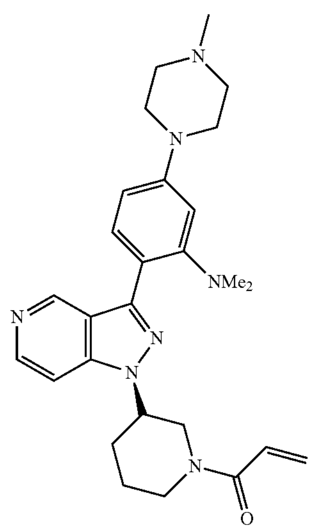 | 461.57/ 461.3 | (R)-1-(3-(3-(2-methoxy-4-(4-methylpiperazin-1-yl)phenyl)-1H-pyrazolo[4,3-c]pyridin-1-yl)piperidin-1-yl)prop-2-en-1-one |

| Entry | Structure | MS(cald) [M + H]+/ MS (found) | Name |
|---|---|---|---|
| 114 | 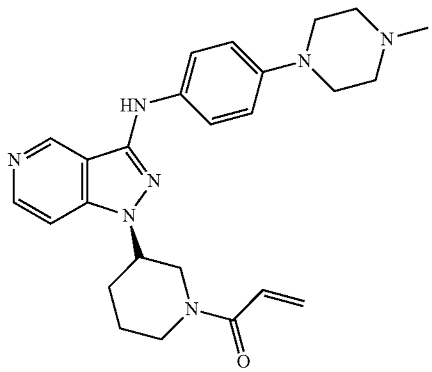 | 446.56/ 446.1 | (R)-1-(3-(3-((4-(4-methylpiperazin-1-yl)phenyl)amino)-1H-pyrazolo[4,3-c]pyridin-1-yl)piperidin-1-yl)prop-2-en-1-one |
| 115 | 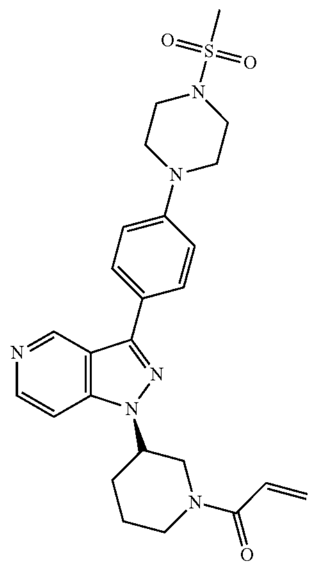 | 495.61/ 495.2 | (R)-1-(3-(3-(4-(4-(methylsulfonyl)piperazin-1-yl)phenyl)-1H-pyrazolo[4,3-c]pyridin-1-yl)piperidin-1-yl)prop-2-en-1-one |
Example 116: N-{4-[1-(1-Acryloyl-pyrrolidin-3-yl)-1H-pyrazolo[4,3-c]pyridin-3-yl]-phenyl}-3-trifluoromethyl-benzamide
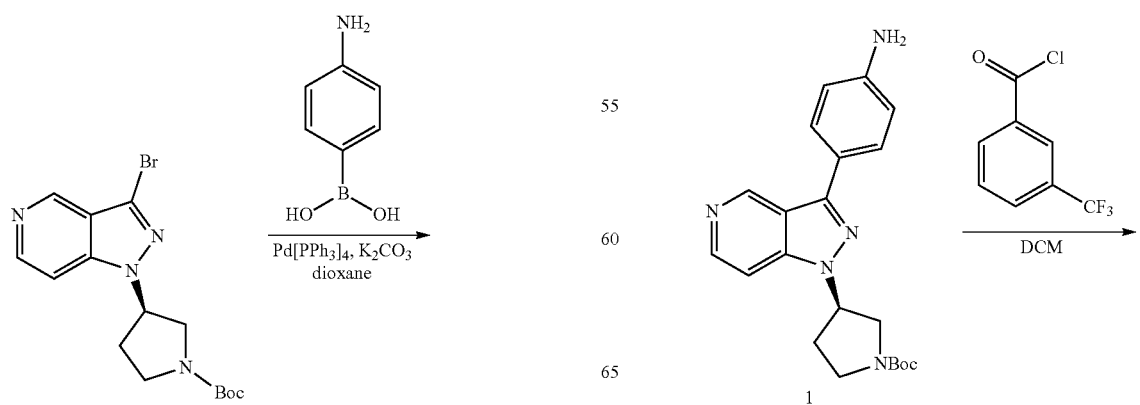

-continued

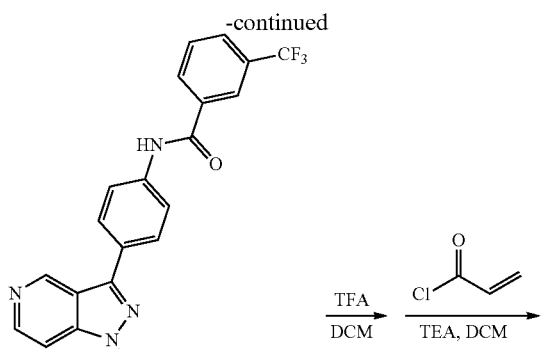

2

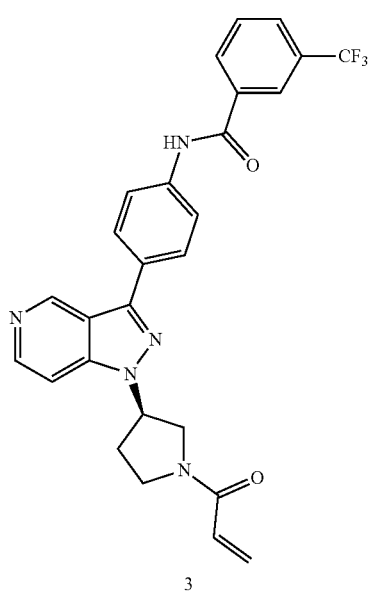

3

Step A: (R)-tert-butyl 3-(3-(4-aminophenyl)-1H-pyrazolo[4,3-c]pyridin-1-yl)pyrrolidine-1-carboxylate (1)

To a solution of (R)-tert-butyl 3-(3-bromo-1H-pyrazolo[4,3-c]pyridin-1-yl)pyrrolidine-1-carboxylate (77 mg, 0.209 mmol, 1.0 eq) and (4-aminophenyl)-boronic acid (57 mg, 0.418 mmol, 2.0 eq) in dioxane (8.0 mL) and water (1.0 mL), was added $K_2CO_3$ (87 mg, 0.628 mmol, 3.0 eq) and $(Ph_3P)_4Pd$ (20 mg) under $N_2$ with stirring. The mixture was refluxed for 5.5 h until the material was disappeared. The reaction mixture was cooled to room temperature. The dioxane was removed by rotary evaporation. The residue was poured into water and extracted with EA. The organic layer was dried over $Na_2SO_4$, filtered and the solvent was removed by vacuum and the residue was purified by flash silica gel chromatography (DCM:MeOH=100:1-50:1), give the title product (77 mg, yield 96.8%). LCMS: m/z=380 [M+H]$^+$.

Step B: (R)-tert-butyl3-(3-(4-((3-(trifluoromethyl)phenyl)amino)phenyl)-1H-pyrazolo[4,3-c]pyridin-1-yl)pyrrolidine-1-carboxylate (2)

To a solution of 1 (77 mg, 0.203 mmol, 1.0 eq) in DCM (5.0 mL), 3-(trifluoromethyl)benzoyl chloride (51 mg, 0.243 mmol, 1.2 eq) which was dissolved in DCM (2.0 mL) added, dropwise. The mixture was stirred at room temperature for 2.0 h, added water, then the mixture was extracted with DCM, The organic layer was washed with water and brine, dried with anhydrous $Na_2SO_4$, filtered and concentrated, The product was purified with flash silica gel chromatography (DCM:MeOH=100:1-50:1), give the title product (60 mg, 56.5%)._LCMS: m/z=524 [M+H]$^+$.

Step C: (R)-1-(3-(3-(4-((3-(trifluoromethyl)phenyl)amino)phenyl)-1H-pyrazolo[4,3-c]pyridin-1-yl)pyrrolidin-1-yl)prop-2-en-1-one (3)

Intermediate 2 (60 mg, 0.115 mmol, 1.0 eq) were dissolved in DCM (8.0 mL), added TFA (1.0 mL) in one portion. The mixture was stirred for about 1.5 h at rt. Volatile components were removed under vacuum to give the title crude product TFA salt, and directly used in next step without further purification. The crude product was dissolved in DCM (5.0 mL), added TEA until PH=8.0, then added Acryloyl chloride (12 mg, 0.133 mmol, 1.2 eq) in DCM (1.0 mL) drop wise to the solution. The reaction mixture was stirred for 0.5 h, poured onto water and extracted with DCM. The organic layer was dried with anhydrous $Na_2SO_4$, filtered and concentrated, the residue was purified with silica gel plate (DCM/MeOH=50:1) to give the title product (19 mg, yield 34.7%). $^1$H-NMR (400 MHz, CDCl$_3$): δ 9.34 (d, J=14.0 Hz, 1H), 9.09 (d, J=6.0 Hz, 1H), 8.15-8.47 (m, 3H), 7.77-7.95 (m, 5H), 7.58-7.62 (m, 1H), 7.35-7.39 (m, 1H), 6.37-6.54 (m, 2H), 5.69-5.75 (m, 1H), 5.21-5.30 (m, 1H), 4.38 (d, J=9.6 Hz, 1H), 4.01-4.18 (m, 3H), 3.80-3.85 (m, 1H), 2.47-2.75 (m, 2H). LCMS: m/z=506.2 [M+H]$^+$.

The following additional Example 117 shown in the Table below were prepared following the procedures outlined in the general methods above and detailed in Example 116.

| Entry | Structure | MS(cald) [M + H]+/ MS (found) | Name |
|---|---|---|---|
| 117 | 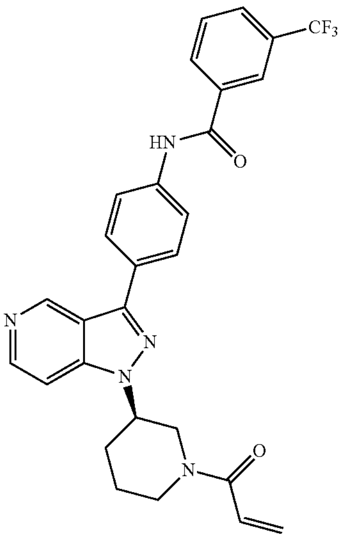 [SMILES: C=CC(=O)N1CCC[C@@H](n2nc(-c3ccc(NC(=O)c4cccc(C(F)(F)F)c4)cc3)c3cnccc32)C1] | 520.19/ 520.2 | (R)-N-(4-(1-(1-acryloylpiperidin-3-yl)-1H-pyrazolo[4,3-c]pyridin-3-yl)phenyl)-3-(trifluoromethyl)benzamide |

The following additional Other examples 118-123 in the Table below were prepared following the procedures in the general methods from above or reported literature.

| Entry | Structure | MS(cald) [M + H]+/ MS (found) | Name |
|---|---|---|---|
| 118 | 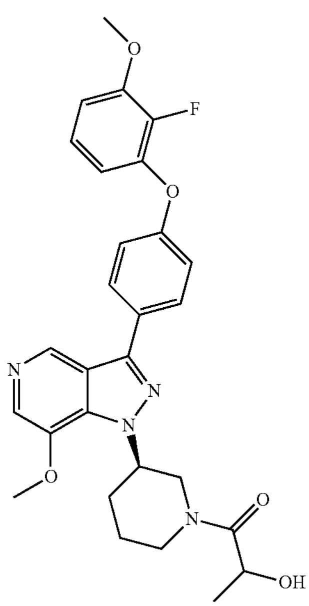 [SMILES: COc1cccc(Oc2ccc(-c3nn([C@@H]4CCCN(C(=O)C(C)O)C4)c4c(OC)cncc34)cc2)c1F] | 521.55/521.1 | 1-((R)-3-(3-(4-(2-fluoro-3-methoxyphenoxy)phenyl)-7-methoxy-1H-pyrazolo[4,3-c]pyridin-1-yl)piperidin-1-yl)-2-hydroxypropan-1-one |

-continued

| Entry | Structure | MS(cald) [M + H]+/ MS (found) | Name |
|---|---|---|---|
| 119 | 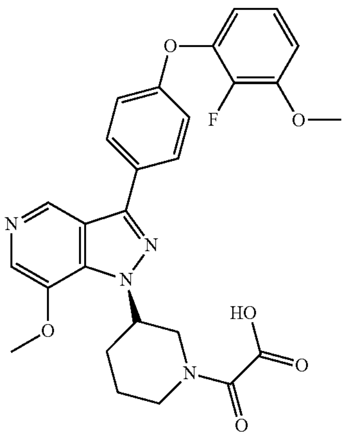 | 521.51/521.2 | (R)-2-(3-(3-(4-(2-fluoro-3-methoxyphenoxy)phenyl)-7-methoxy-1H-pyrazolo[4,3-c]pyridin-1-yl)piperidin-1-yl)-2-oxoacetic acid |
| 120 | 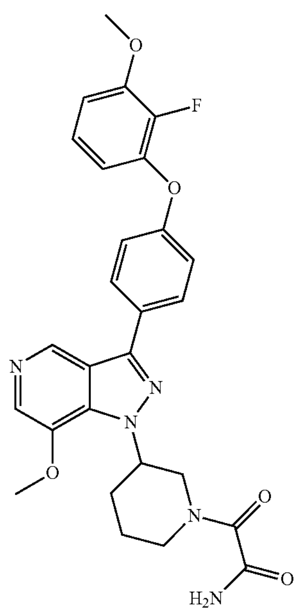 [SMILES: COc1cccc(Oc2ccc(-c3nn(C4CCCN(C(=O)C(N)=O)C4)c4c(OC)cncc34)cc2)c1F] | 520.52/520.5 | (R)-2-(3-(3-(4-(2-fluoro-3-methoxyphenoxy)phenyl)-7-methoxy-1H-pyrazolo[4,3-c]pyridin-1-yl)piperidin-1-yl)-2-oxoacetamide |
| 121 | 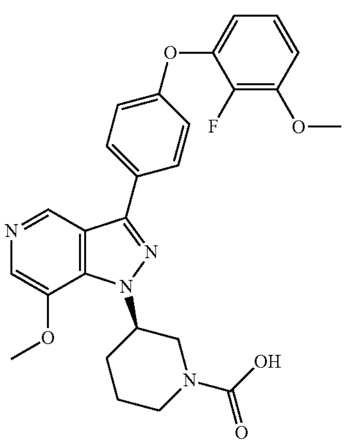 [SMILES: COc1cccc(Oc2ccc(-c3nn([C@@H]4CCCN(C(=O)O)C4)c4c(OC)cncc34)cc2)c1F] | 492.51/492.2 | (3R)-3-(3-(4-(2-fluoro-3-methoxyphenoxy)phenyl)-7-methoxy-1H-pyrazolo[4,3-c]pyridin-1-yl)cyclohexanecarboxylic acid |

| Entry | Structure | MS(cald) [M + H]⁺/ MS (found) | Name |
|---|---|---|---|
| 122 | 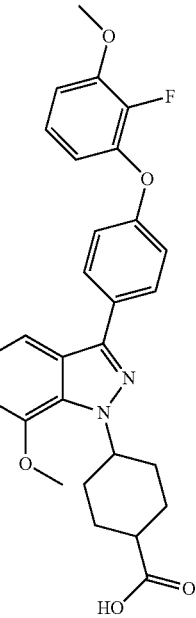 | 492.51/492.2 | 4-(3-(4-(2-fluoro-3-methoxyphenoxy)phenyl)-7-methoxy-1H-pyrazolo[4,3-c]pyridin-1-yl)cyclohexanecarboxylic acid |
| 123 | 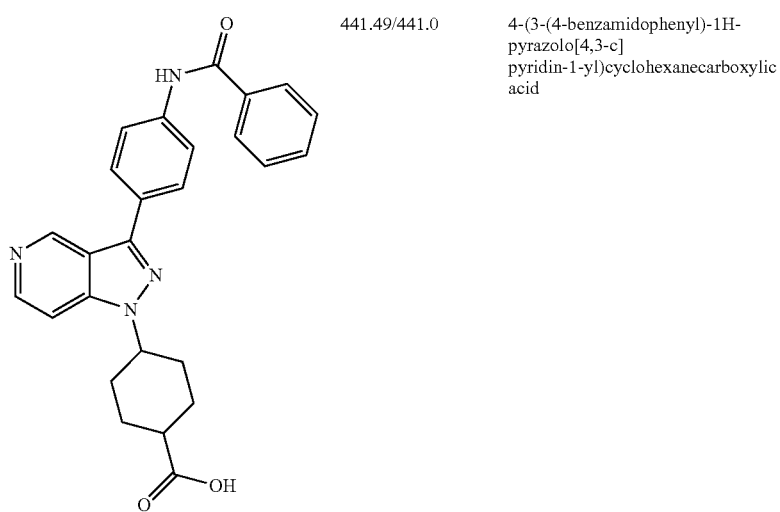 | 441.49/441.0 | 4-(3-(4-benzamidophenyl)-1H-pyrazolo[4,3-c]pyridin-1-yl)cyclohexanecarboxylic acid |

-continued

| Entry | Structure | MS(cald) [M + H]+/ MS (found) | Name |
|---|---|---|---|
| 124 | 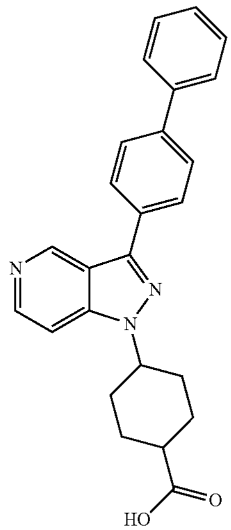 [SMILES: O=C(O)C1CCC(n2nc(-c3ccc(-c4ccccc4)cc3)c3cnccc32)CC1] | 398.47/398.1 | 4-(3-([1,1'-biphenyl]-4-yl)-1H-pyrazolo[4,3-c]pyridin-1-yl)cyclohexanecarboxylic acid |
| 125 | 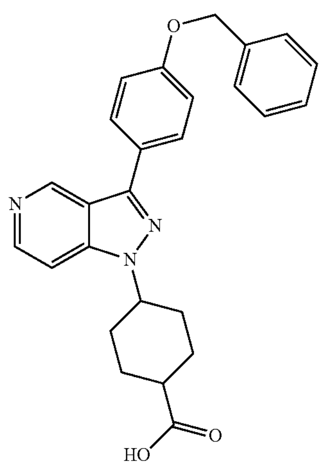 [SMILES: O=C(O)C1CCC(n2nc(-c3ccc(OCc4ccccc4)cc3)c3cnccc32)CC1] | 428.50/428.2 | 4-(3-(4-(benzyloxy)phenyl)-1H-pyrazolo[4,3-c]pyridin-1-yl)cyclohexanecarboxylic acid |
| 126 | 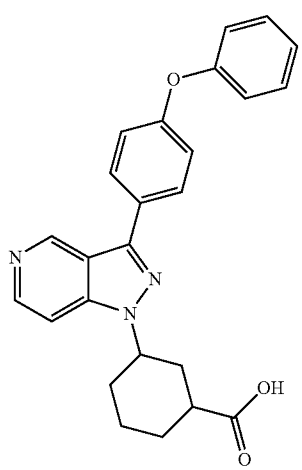 [SMILES: O=C(O)C1CCCC(n2nc(-c3ccc(Oc4ccccc4)cc3)c3cnccc32)C1] | 414.47/414.1 | 3-(3-(4-phenoxyphenyl)-1H-pyrazolo[4,3-c]pyridin-1-yl)cyclohexanecarboxylic acid |

Btk Kinase Assay and Other Kinases Assay

Btk kinase activity was determined using a homogenous time resolved fluorescence (HTRF) methodology. Measurements were performed in a reaction volume of 15 μL using 384-well assay plates. Kinase enzyme, inhibitor, ATP and 1 μM peptide substrate were incubated in a reaction buffer compose of Hepes 50 mM (pH7.0), NaN3 0.02%, BSA 0.01%, Orthocanadate 0.1 mM. After one hour, the kinase reaction was quenched by the addition of Eμ-labeled antibody and XL-665 in 1×Detection buffer containing 60 mM EDTA (Cisbio), and the mixture was allowed to incubate for one hour. The HTRF signal was measured on a multimode plate reader (EnVision® Multilabel Reader, Perkin Elmer) with an excitation wavelength ($\lambda_{Ex}$) of 330 nm and detection wavelengths ($\lambda_{Em}$) of 615 and 665 nm. Activity was determined by the ratio of the fluorescence at 665 nm to that at 615 nm. For each compound, enzyme activity as measured at various concentrations of compound, Negative control reactions were performed in the absence of inhibitor in two replicates and eight no enzyme controls were used to determine baseline fluorescence levels. $IC_{50S}$ were obtained according to the equation:

$$Y=100/(1+10^{((Log\ IC50-X)*HillSlope))}.$$

For BTK assay, [ATP]=80 μM, BTK=3.4 nM.
For LYN assay, [ATP]=20 μM, LYN=0.12 nM. For LCK assay, [ATP]=20 μM, LCK=0.2 nM. For BLK assay, [ATP]=20 μM, BLK=0.6 nM.

Example 127

The following Table shows the activity of selected compounds of this invention in the BTK inhibition assay. The compound numbers correspond to the compound numbers in previous Tables. Compounds having an activity designated as "A" provided an IC50≤10 nM; Compounds having an activity designated as "B" provided an $IC_{50}$ 10-100 nM; Compounds having an activity designated as "C" provided an $IC_{50}$ 100-1000 nM; Compounds having an activity designated as "D" provided an $IC_{50}$ 1000-10000 nM; Compounds having an activity designated as "E" provided an $IC_{50}$≥10000 nM.

BTK Inhibition Data

| Compound # | BTK Inhibition | Compound # | BTK Inhibition | Compound # | BTK Inhibition | Compound # | BTK Inhibition |
|---|---|---|---|---|---|---|---|
| 1 | A | 2 | A | 3 | A | 4 | A |
| 5 | A | 6 | A | 7 | B | 8 | C |
| 9 | B | 10 | B | 11 | A | 12 | B |
| 13 | A | 14 | B | 15 | C | 16 | B |
| 17 | A | 18 | A | 19 | A | 20 | A |
| 21 | B | 22 | B | 23 | B | 24 | A |
| 25 | C | 26 | A | 27 | B | 28 | A |
| 29 | B | 30 | C | 31 | B | 32 | B |
| 33 | A | 34 | C | 35 | B | 36 | B |
| 37 | B | 38 | B | 39 | B | 40 | B |
| 41 | A | 42 | A | 43 | A | 44 | A |
| 45 | D | 46 | E | 47 | A | 48 | B |
| 49 | B | 50 | B | 51 | B | 52 | B |
| 53 | B | 54 | B | 55 | B | 56 | B |
| 57 | B | 58 | A | 59 | B | 60 | B |
| 61 | A | 62 | A | 63 | A | 64 | A |
| 65 | B | 66 | A | 67 | A | 68 | A |
| 69 | A | 70 | A | 71 | A | 72 | B |
| 73 | A | 74 | C | 75 | A | 76 | A |
| 77 | A | 78 | A | 79 | A | 80 | A |
| 81 | A | 82 | A | 83 | A | 84 | A |
| 85 | A | 86 | A | 87 | B | 88 | B |
| 89 | C | 90 | B | 91 | A | 92 | B |
| 93 | A | 94 | B | 95 | B | 96 | B |
| 97 | A | 98 | A | 99 | A | 100 | B |
| 101 | B | 102 | B | 103 | C | 104 | C |
| 105 | C | 106 | C | 107 | B | 108 | C |
| 109 | C | 110 | B | 111 | C | 112 | C |
| 113 | C | 114 | D | 115 | C | 116 | B |
| 117 | B | 118 | B | 119 | B | 120 | B |
| 121 | B | 122 | A | 123 | E | 124 | E |
| 125 | N/A | 126 | N/A | | | | |

Example 128

The following Table shows the activity of selected compounds of this invention in the BTK, BLK, LYN, LCK inhibition assay. The compound numbers correspond to the compound numbers in previous Tables. Compounds having an activity designated as "A" provided an $IC_{50}$≤10 nM; Compounds having an activity designated as "B" provided an $IC_{50}$ 10-100 nM; Compounds having an activity designated as "C" provided an $IC_{50}$ 100-1000 nM; Compounds having an activity designated as "D" provided an $IC_{50}$ 1000-10000 nM; Compounds having an activity designated as "E" provided an $IC_{50}$≤10000 nM; N/A is not available.

TABLE 2

| Compound | BTK $IC_{50}$ | BLK $IC_{50}$ | LYN $IC_{50}$ | LCK $IC_{50}$ | EGFR $IC_{50}$ |
|---|---|---|---|---|---|
| 1 | A | A | E | D | C |
| 6 | A | B | D | D | C |

Calcium FluxAssay

Calcium flux fluorescence-based assays were performed in aFDSS7000EX (Hamamatsu Photonics) fluorometric imaging plate reader according to manufacturer instructions. Compounds to be assayed were dissolved in DMSO, diluted to appropriate concentrations in $Ca^{2+}$ buffer ranging from 0 to 10 μM (at a dilution factor of 0.1), added 5 μl (6×) to each well (the final DMSO concentration was 0.1% in each well). Then 12.5 ΞL 2× dye loading solution (Fluo-4 NW Calcium Assay Kits, Invitrogen) was added per well of a 384-well plate. Afterwards, actively growing Ramos cells (ATCC) in RPM1640 medium supplemented with 10% FBS (Invitrogen) were washed and re-plated in assay buffer (from Fluo-4 NW Calcium Assay Kits, Invitrogen) to approximately 6.4× $10^6$/ml (80000 cells/12.5 μL in 384-well plates). The plates were incubated at 37° C. for 30 minutes, then at room temperature for an additional 30 minutes. The plates were now ready to be used in an experiment. Immediately after the transfer and a 10-s recording of baseline fluorescence, the compound treated cells were stimulated with a goat anti-human IgM antibody (10 μg/ml; Jackson Immuno Research) and read in a FDSS for 240 seconds. Difference between the signal and that at baseline, designated adjusted relative fluorescence unit, was calculated by using a custom Excel (Microsoft, Redmond, Wash.) template to determine IgM-induced calcium influx and its inhibition by compounds. The table belows show the result. Compounds having an activity designated as "A" provided an $IC_{50}$≤10 nM; Compounds having an activity designated as "B"

provided an $IC_{50}$ 10-100 nM; Compounds having an activity designated as "C" provided an $IC_{50}$ 100-1000 nM;

TABLE 3

| Compound | Ramos Ca Flux (nM) |
|---|---|
| Example 1 | B |
| Example 2 | B |
| Example 3 | B |
| Example 4 | B |
| Example 6 | B |
| Example 11 | C |
| Example 17 | B |
| Example 18 | B |
| Example 19 | B |
| Example 20 | B |
| Example 41 | B |
| Example 43 | B |
| Example 58 | B |
| Example 61 | C |
| Example 62 | C |
| Example 63 | C |
| Example 64 | B |

Btk Occupancy in Cellular Assays

For PCI-33380 labeling of human B cells, $10^6$ Jeko-1 cells were pre-incubated with compound for 1.5 h before labeling. Then cells were treated with PCI-33380 at 5 µM for 1 h. Washed, lysed in Ripa buffer containing sample reducing agent, and analyzed by SDS/PAGE and fluorescent gel scanning using a Typhoon scanner 9500 (GE Healthcare) (Ex, 532 nm; Em, 555 nm). The gel was then blotted and total Btk levels detected by standard Western blot with Btk antibody (CST). By using the fluorescently tagged derivative PCI-33380, we found that 25 nM of compound 77; 50 nM of compound 3, 78, 79, 80, 83, 100 nM of Compound 2, 4, 17, 41, 43, 69, 71, 73, 98 and 99 were sufficient to fully occupy the active site of Btk in human mantle cell lymphoma cell lines Jeko-1 cells in culture.

Btk Occupancy In Vivo

For analysis of Btk occupancy in Babc/L mice following oral dosing of compounds after 4 hours. Isolating peripheral blood mononuclear cells (PBMCs) with mouse peripheral blood separation kit (Hao Yang Biological Manufacture CO., LTD, Tianjin) were collected from Babc/L mice (1 ml blood from two mice). Spleens were processed to splenocytes followed by 5 min incubation in red blood cell lysing buffer (from mouse peripheral blood separation kit). PBMCs or splenocytes were then PCI-33380-labeled and lysates analyzed by fluorescent gel scanning as described in cellular assays. Compound 2, 3, 4, 71 were achieved full occupancy at 10 mg/kg single oral dose in all Babc/L mice. Compound 73, 91 were achieved full occupancy at 5 mg/kg single oral dose in all Babc/L mice.

What is claimed is:

1. A compound of Formula (I) having the following structure:

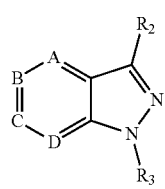

(I)

wherein:

A is $CR^1$;

B, C, and D are each N or C—H, with the proviso that only one or two of A, B, C, and D can be N;

$R^1$ is hydrogen, OH, CN, NHOH or $CONH_2$;

$R^2$ is

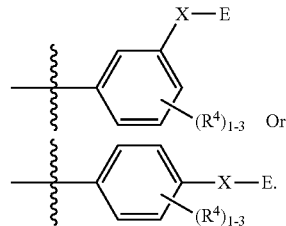

—X-E is one of the following:

(1) X is O, $OCR^aR^b$, $CR^aR^bO$, S(O), $S(O)_2$, $CR^aR^b$, $NR^c(C{=}O)$, $C{=}ONR^c$ or a bond; and E is a hydrogen, an aryl or a heteroaryl substituted with one to three $R^5$ substituents;

or a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or (2) —X-E is hydrogen, halogen, —$OR^a$, —$O(CH_2)_{1-4}$ $R^a$, —CN, —$NO_2$;

$R^4$ and $R^5$ are each independently selected from the group consisting of hydrogen, halogen, hydroxy, cyano, $OCF_3$, $OCF_2H$, $C_{1-6}$ alkyl, optionally substituted with one to five fluorines, $C_{3-6}$ cycloalkyl, optionally substituted with one to five fluorines, $C_{1-4}$alkoxy, optionally substituted with one to five fluorines, $C_{1-4}$ alkylthio, optionally substituted with one to five fluorines, $C_{1-4}$ alkylsulfonyl, optionally substituted with one to five fluorines, carboxy, $C_{1-4}$ alkyloxycarbonyl, and $C_{1-4}$ alkylcarbonyl;

$R^a$ and $R^b$ are each independently hydrogen, fluorine, or $C_{1-3}$ alkyl, optionally substituted with one to five fluorines;

$R^c$ is hydrogen or $C_{1-3}$ alkyl, optionally substituted with one to five fluorines;

$R^3$ is a group having a double bond,

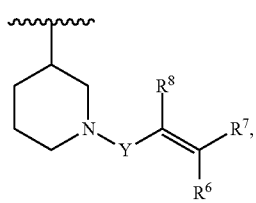 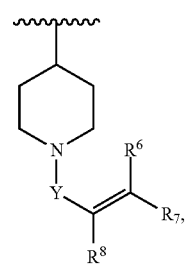

133

-continued

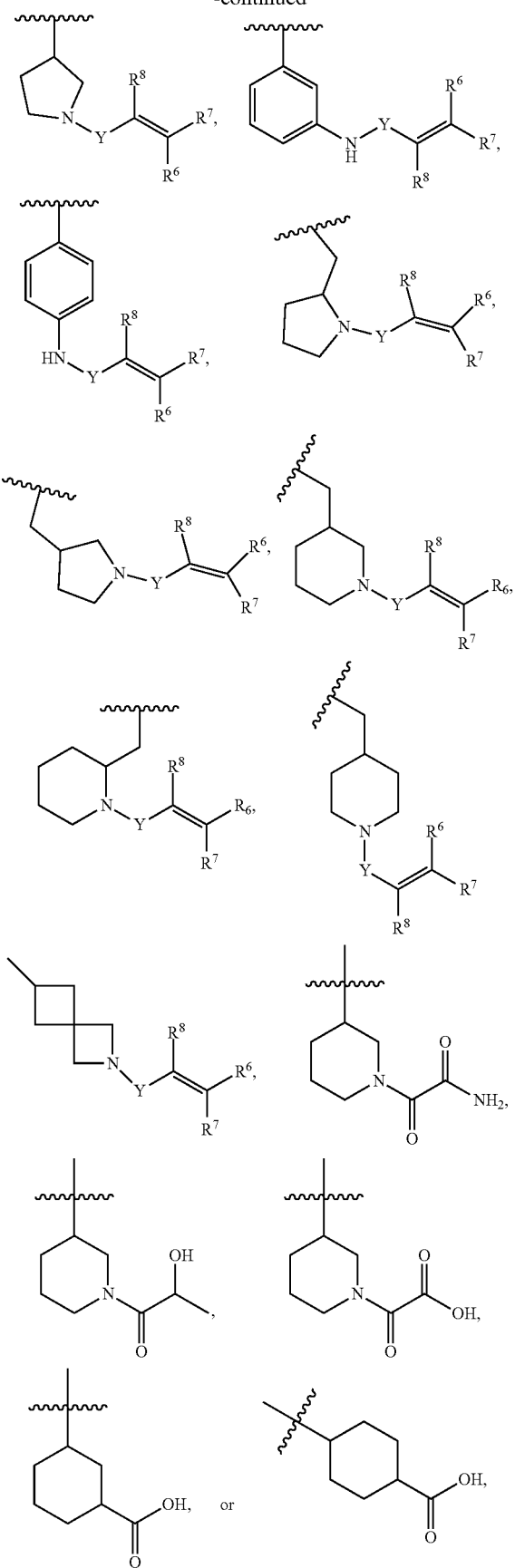

134

Y is C(=O), OC(=O), NHC(=O), S=O, S(=O)$_2$, or NHS(=O)$_2$, and

R$^6$, R$^7$, R$^8$ are each independently hydrogen, halogen, CN, C$_{1-4}$ alkyl, C$_{1-6}$ alkoxyalkyl, C$_{1-8}$ alkylaminoalkyl, or C$_{1-4}$ alkylphenyl; or R$^7$ and R$^8$ taken together form a bond:

a tautomer thereof, a pharmaceutically acceptable solvate thereof, or a pharmaceutically acceptable prodrug thereof.

2. The compound of claim 1, E is selected from aryl, heteroaryl, carbocyclyl, heterocyclyl, any of which is optionally substituted with one to three R$^5$ substituents.

3. The compound of claim 1, wherein one of B, C, and D is N.

4. The compound of claim 1, wherein B is N, and C and D are C—H.

5. A compound according to claim 1 selected from the group consisting of:

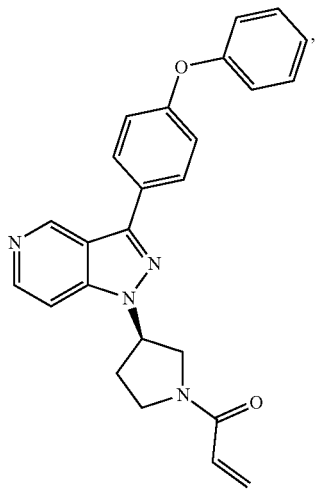

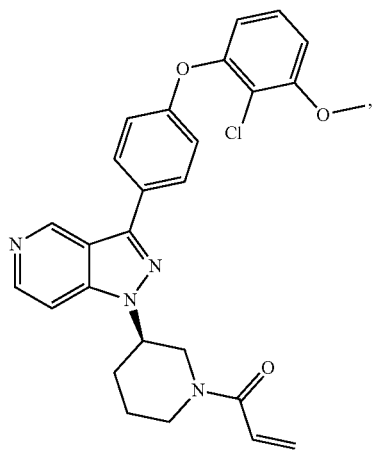

135
-continued
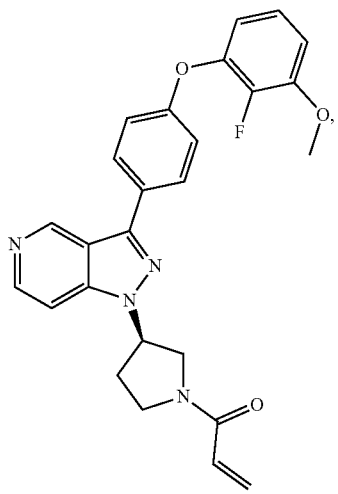
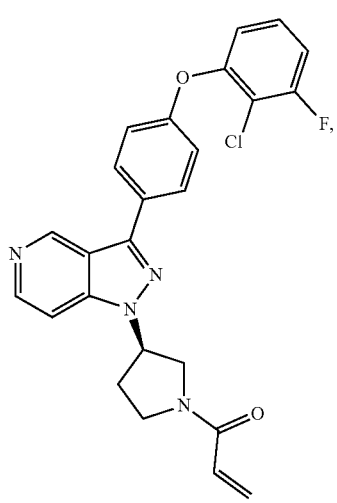
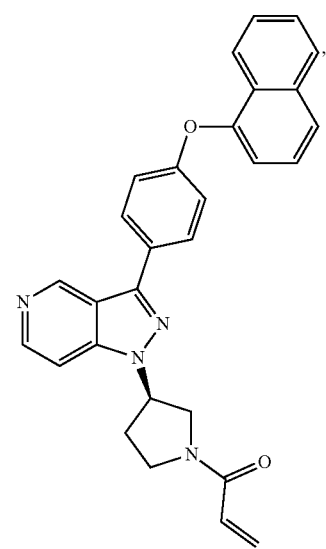
136
-continued
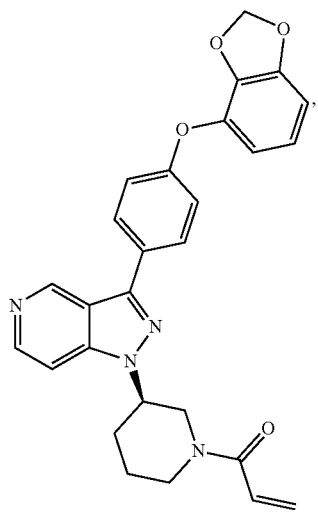
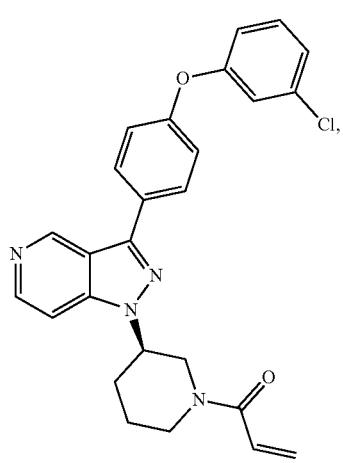
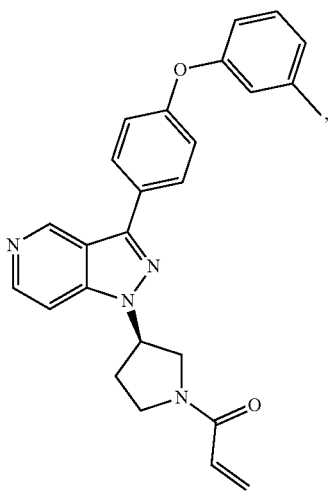

137
-continued
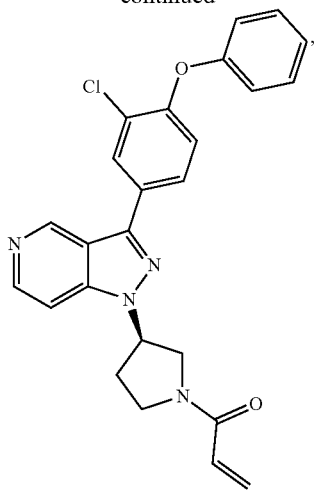
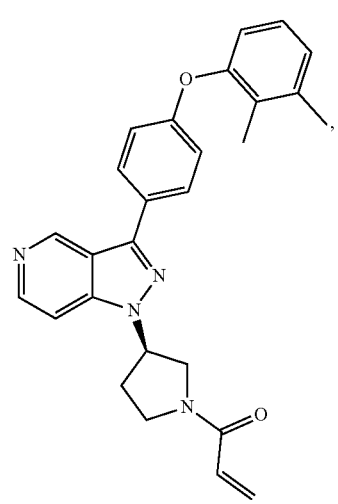
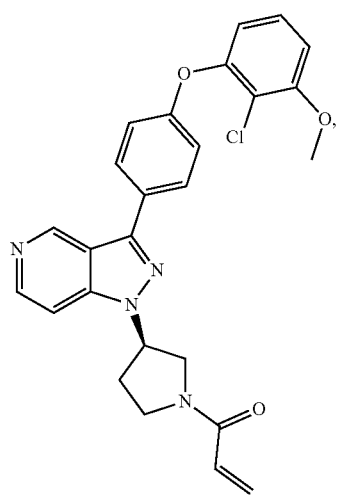
138
-continued
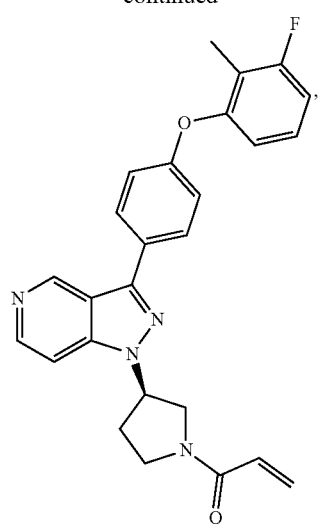
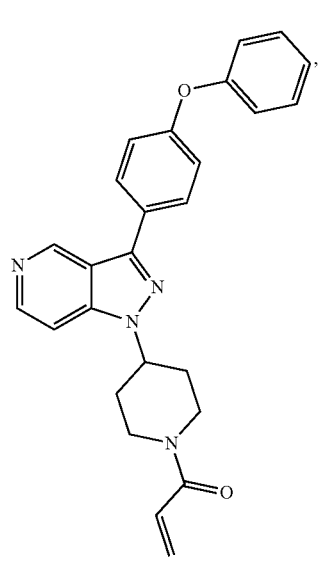
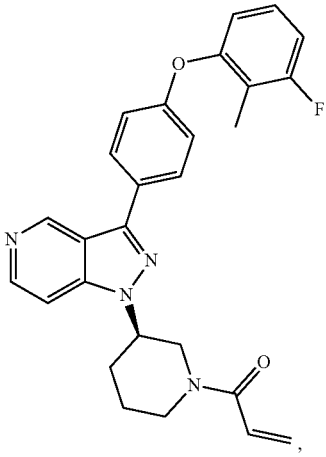

139
-continued
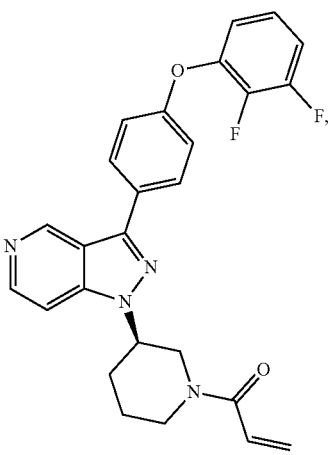
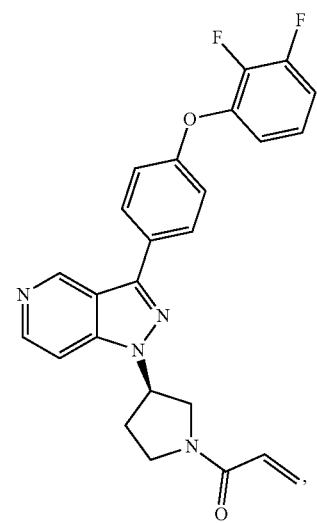
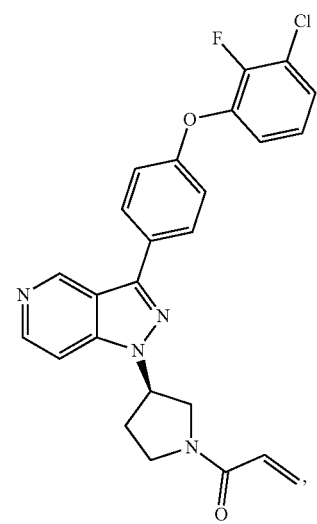
140
-continued
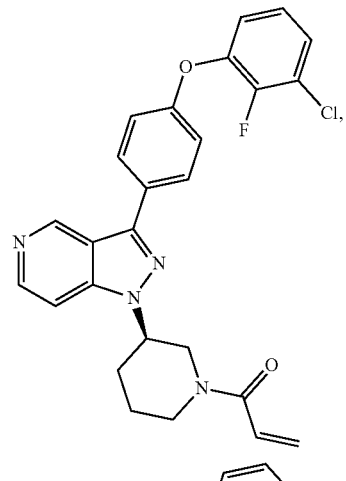
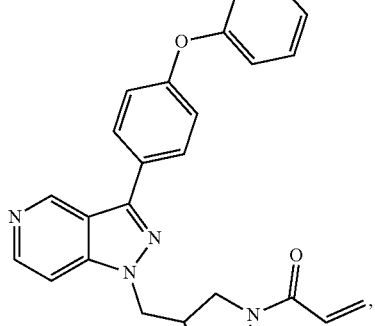
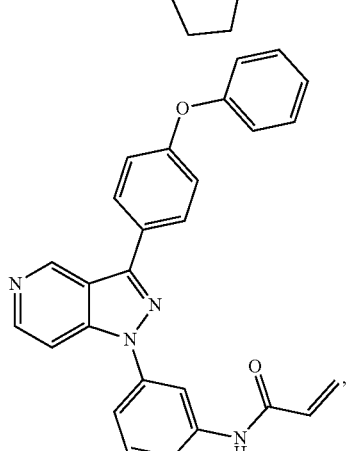
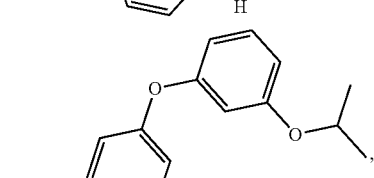
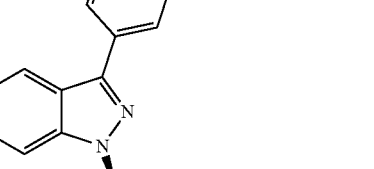
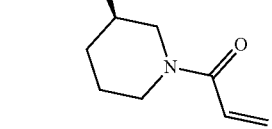

141
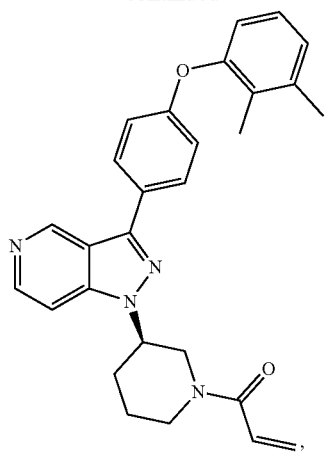
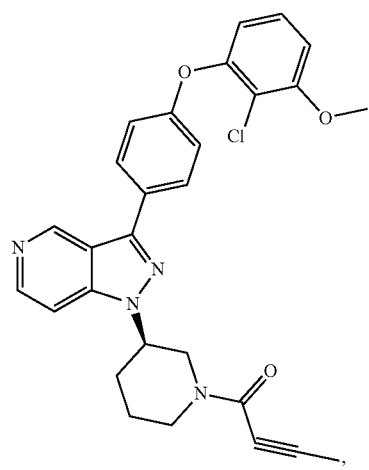
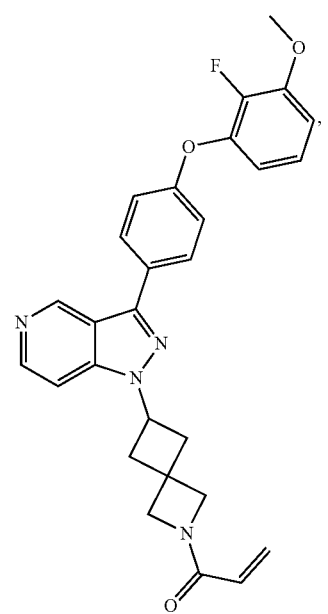
142
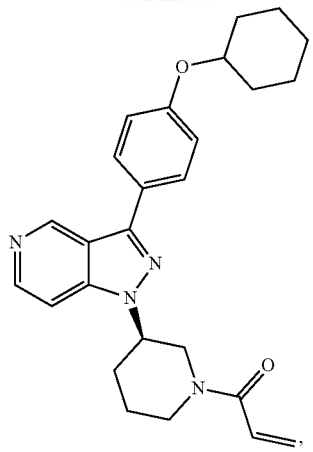
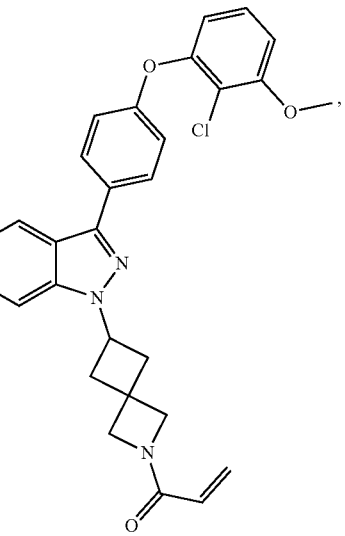
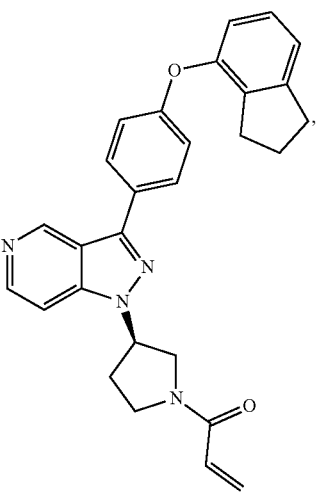

143
-continued
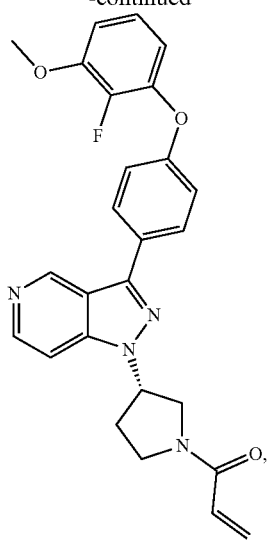
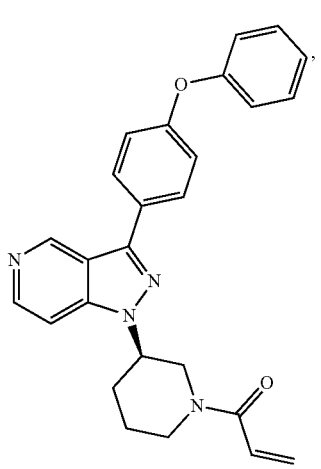
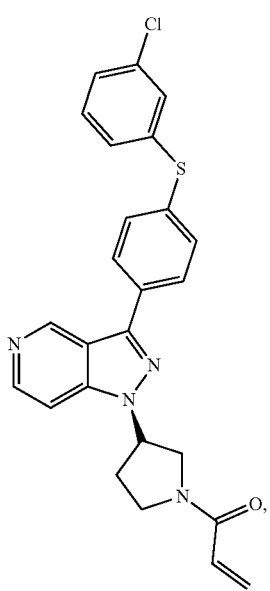
144
-continued
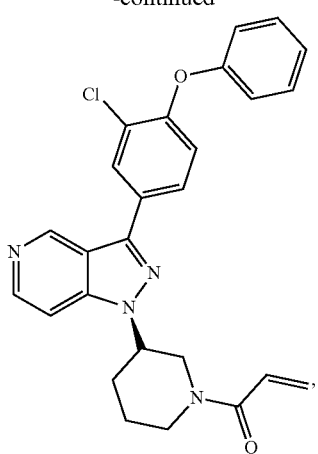
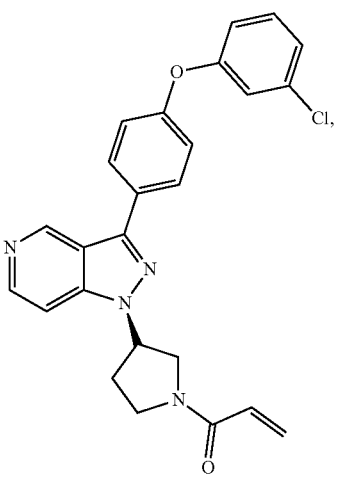
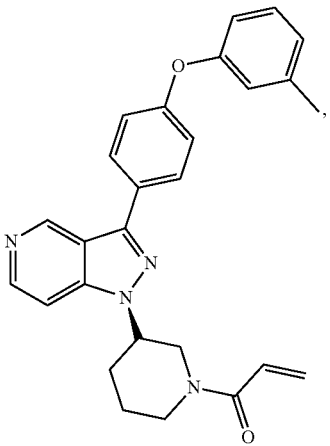

145
-continued
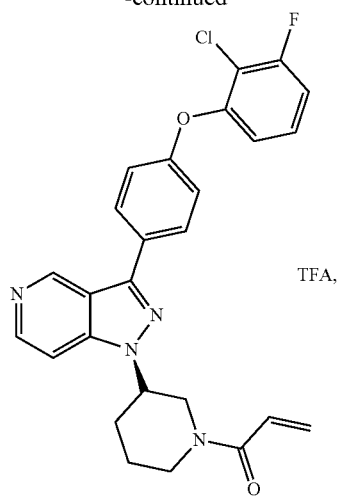
TFA,
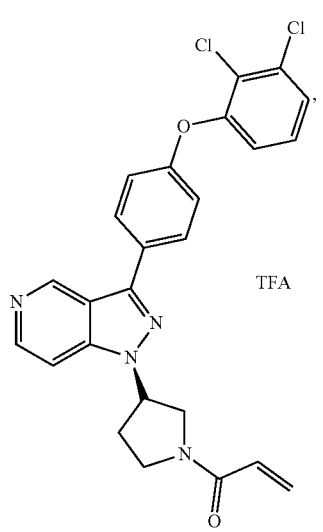
TFA
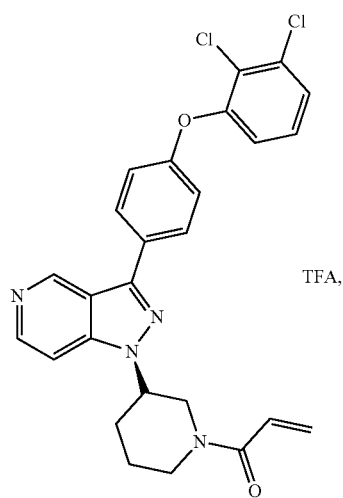
TFA,
146
-continued
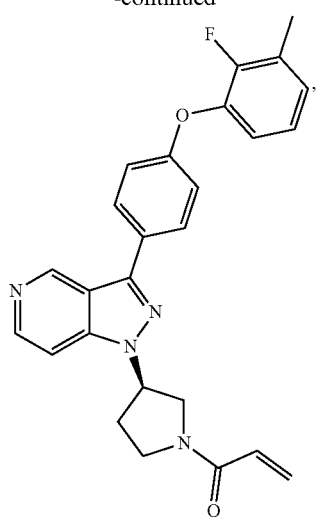
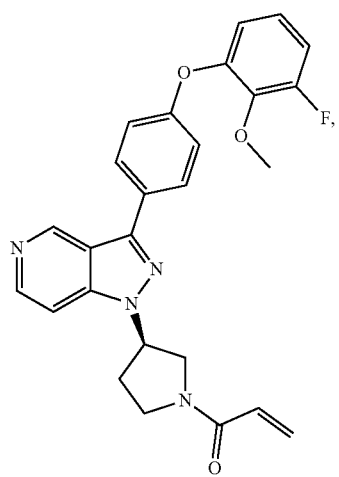

147
-continued
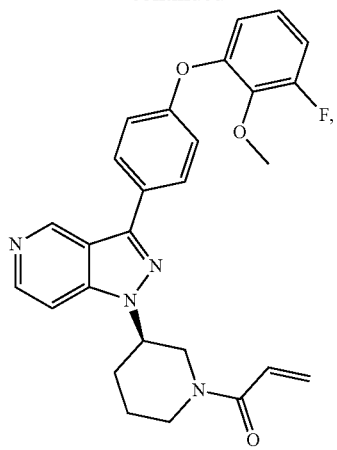
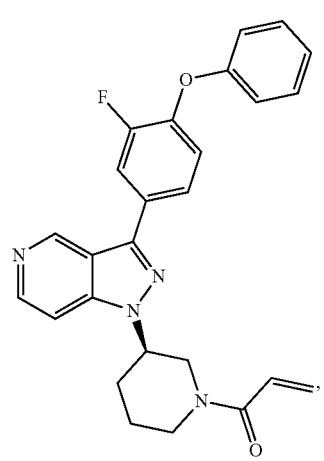
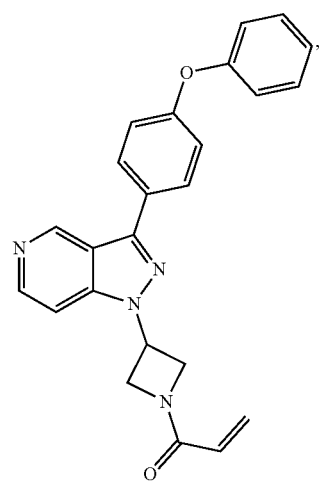
148
-continued
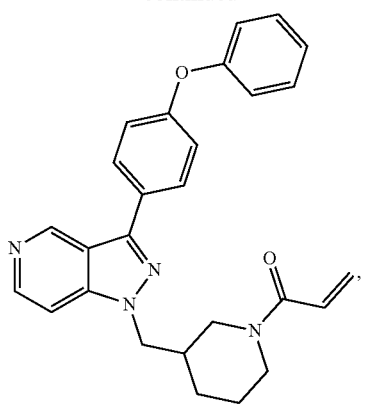
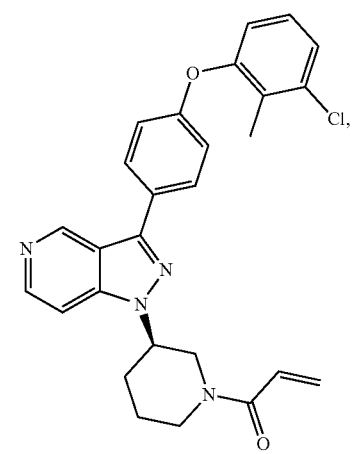
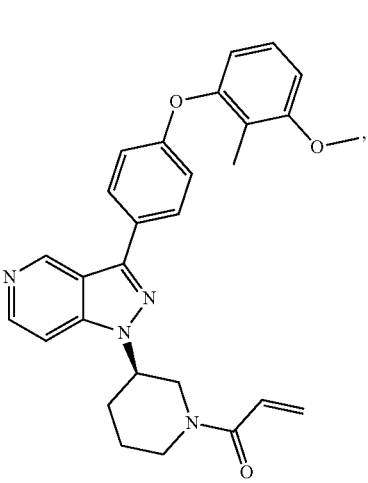

149
-continued
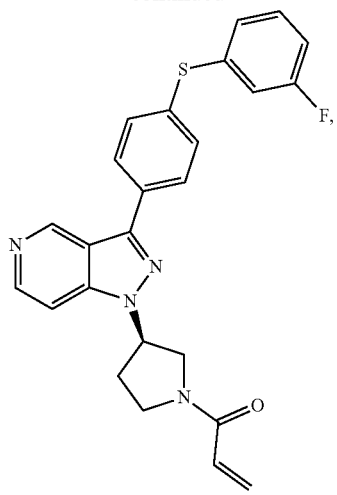
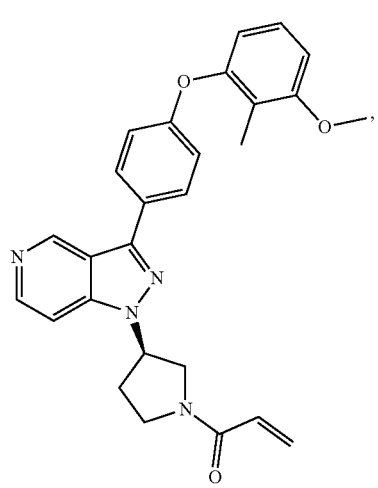
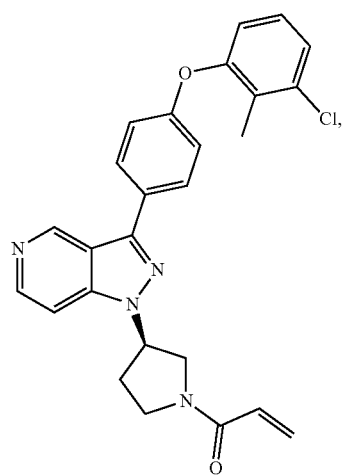
150
-continued
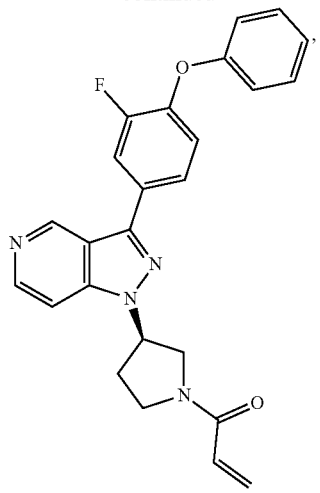
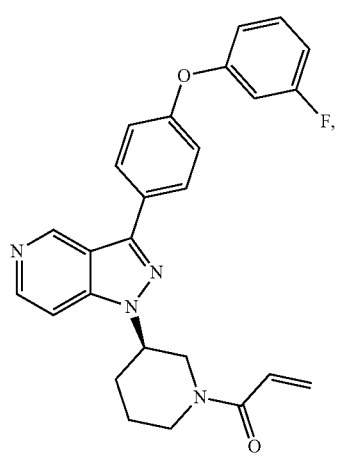
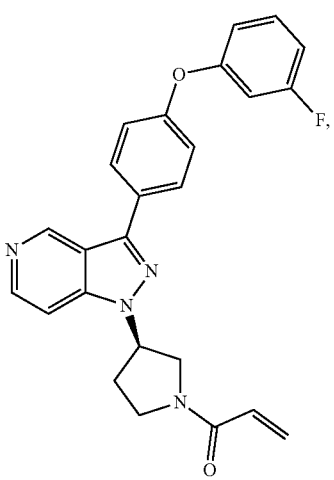

151
-continued
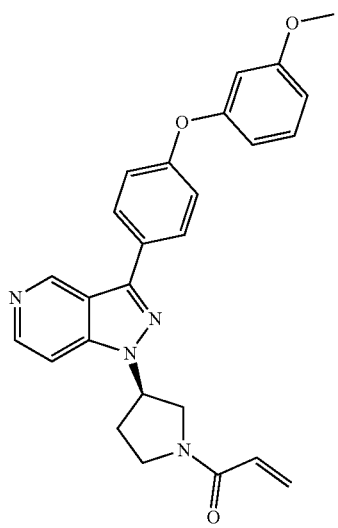
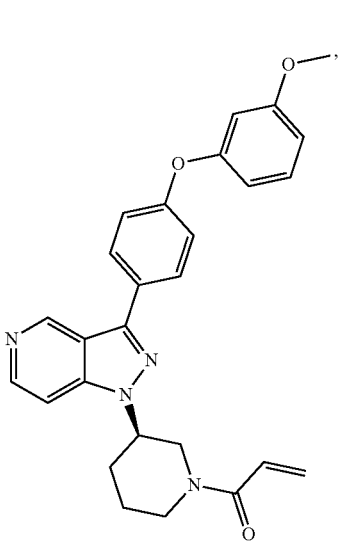
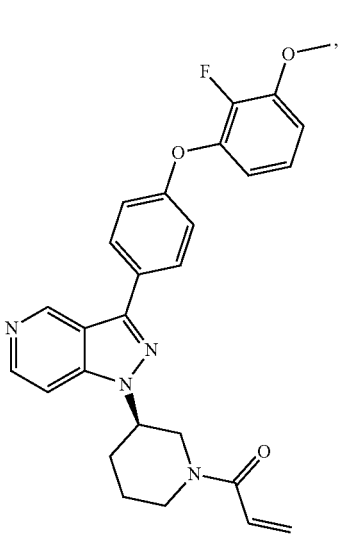
152
-continued
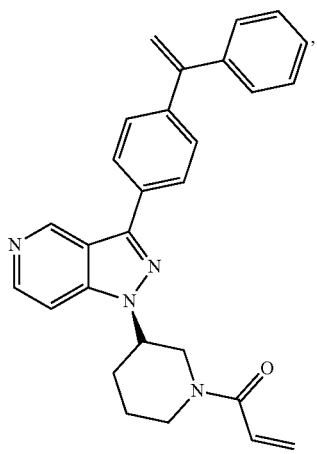
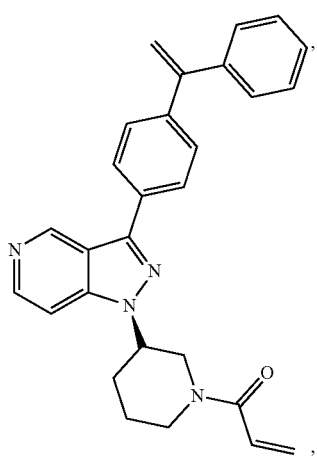
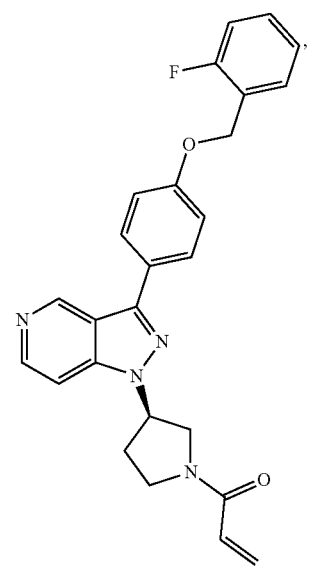

153
-continued
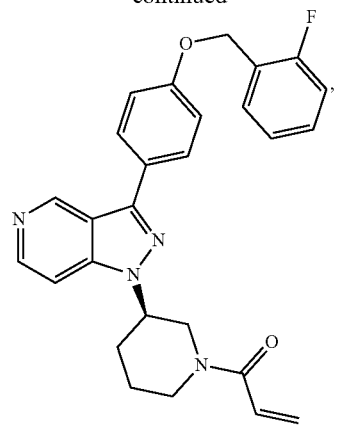
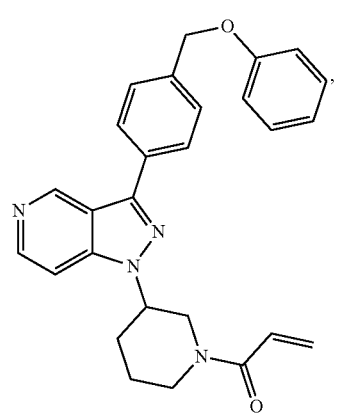
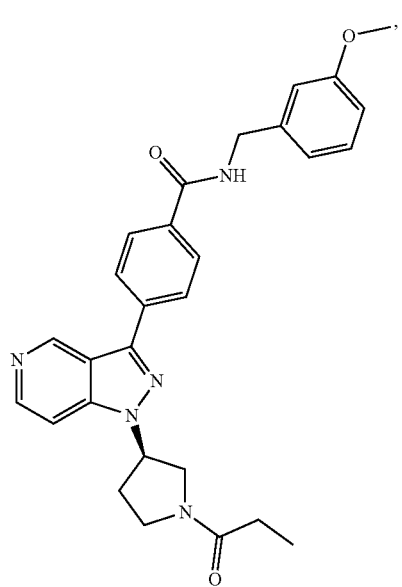
154
-continued
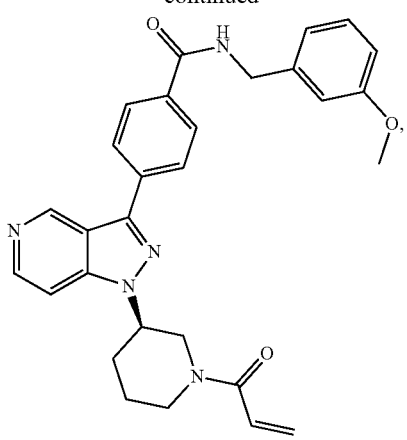
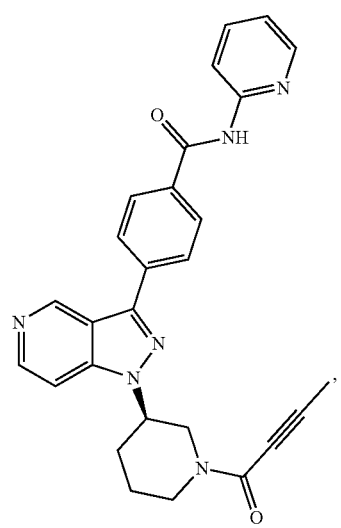
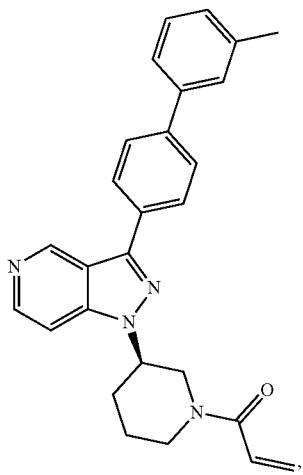

155
-continued
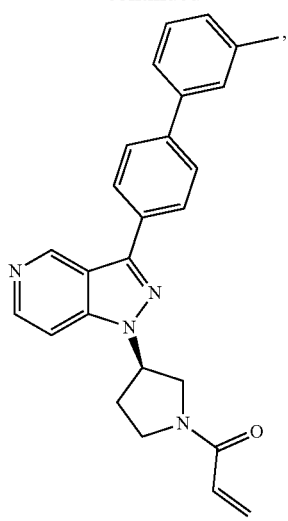
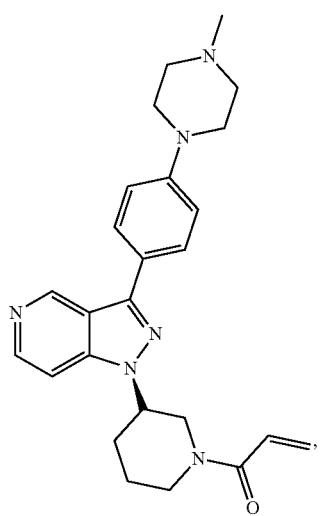
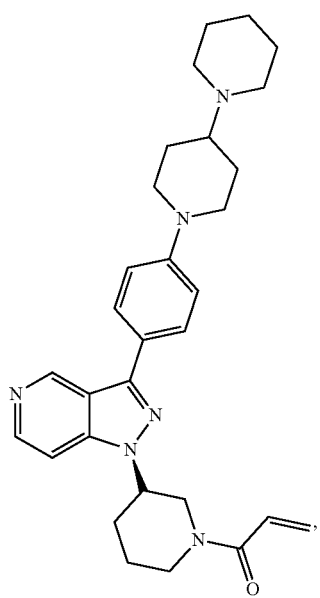
156
-continued
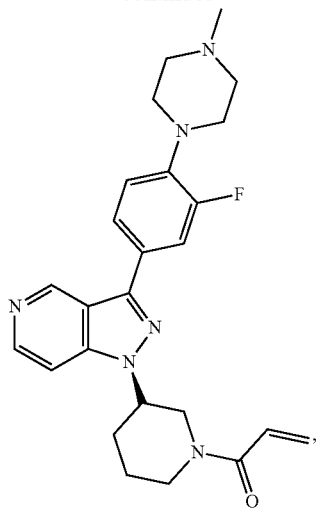
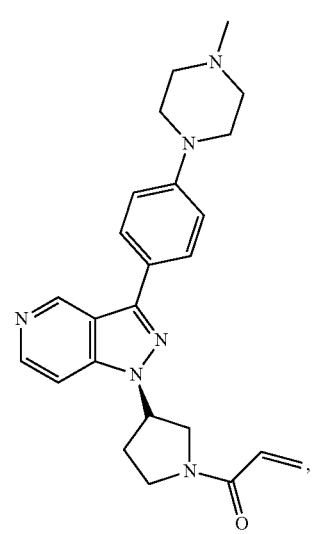
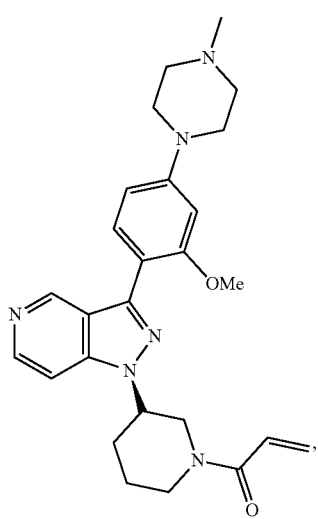

157
-continued
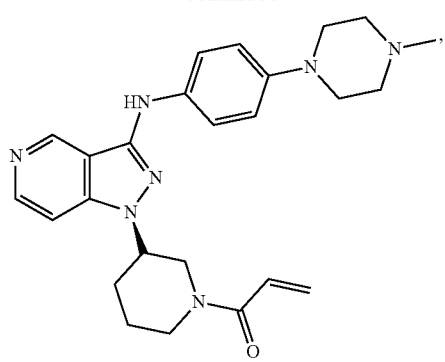
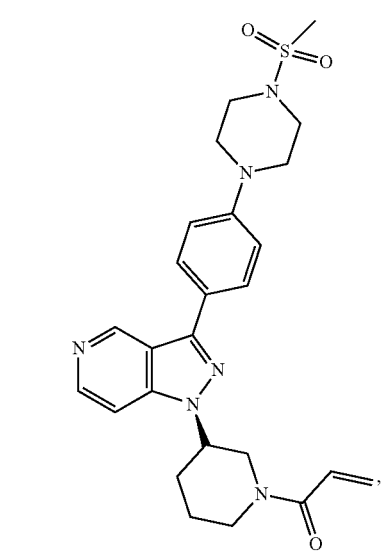
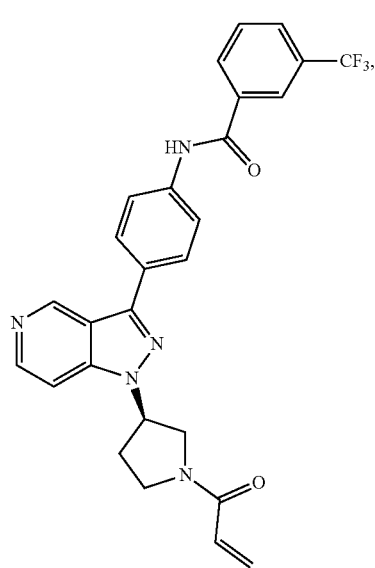
158
-continued
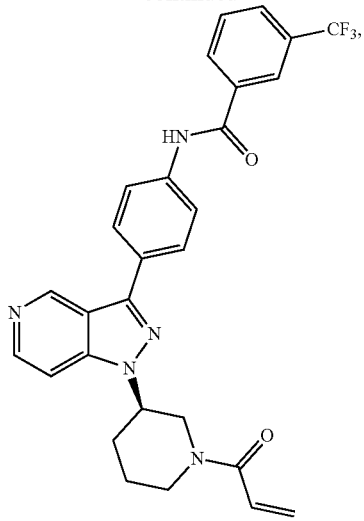
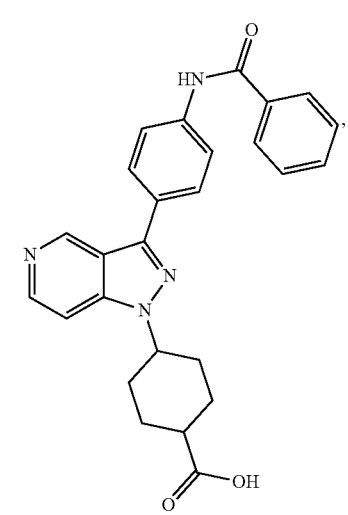
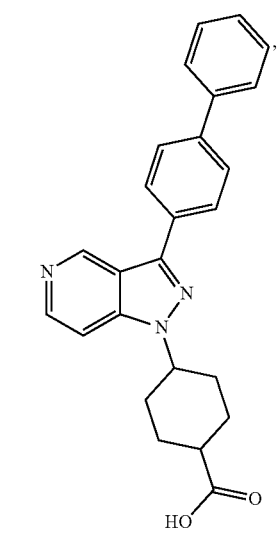

159
-continued
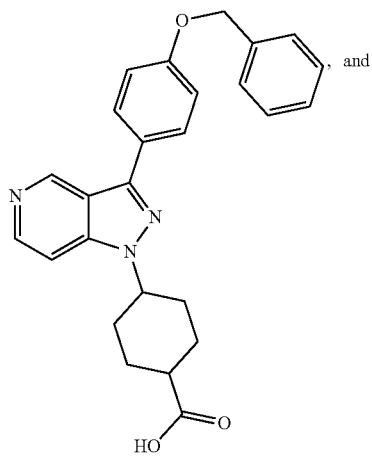
, and
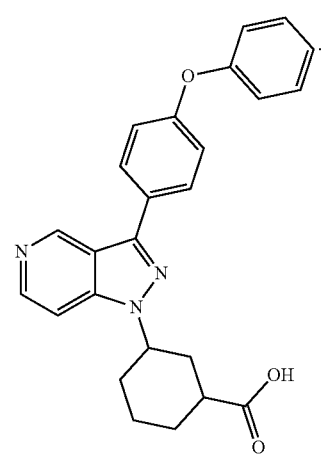
6. A compound selected from the group consisting of:
160
-continued
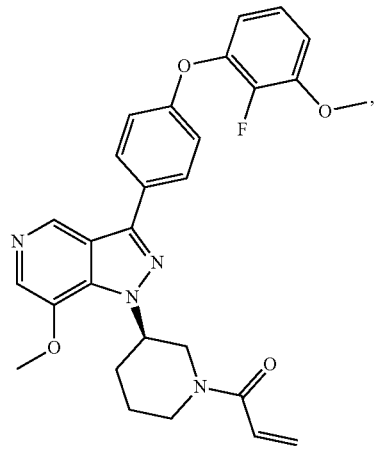
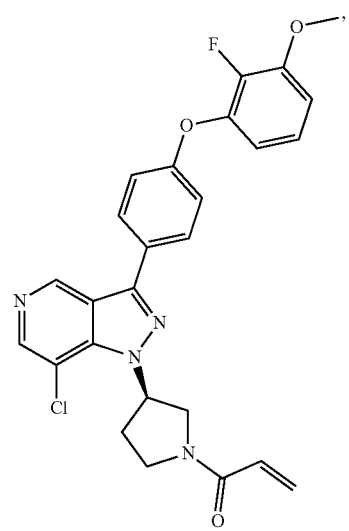
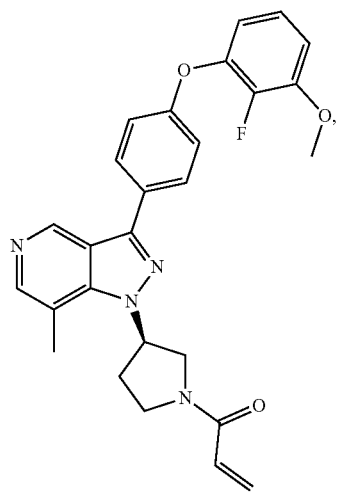
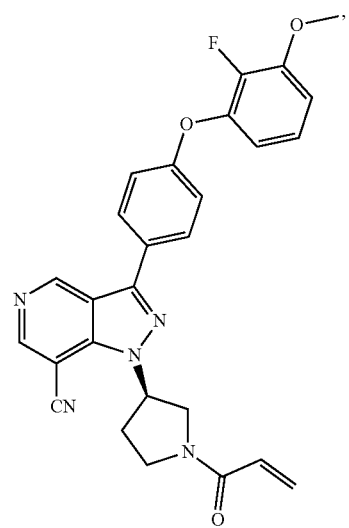

-continued
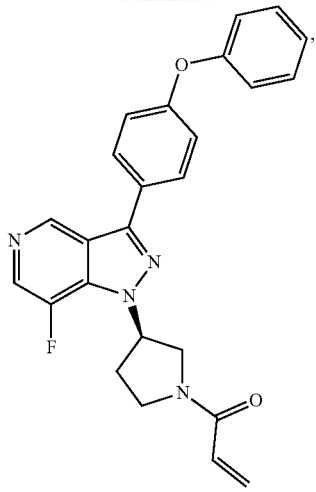
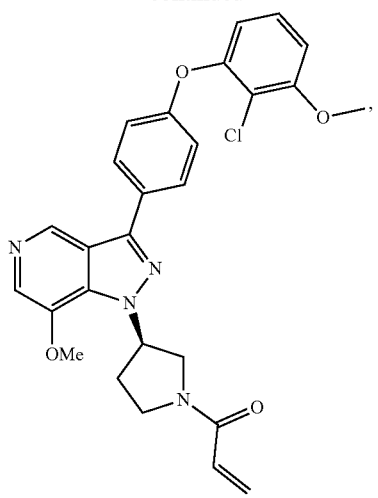
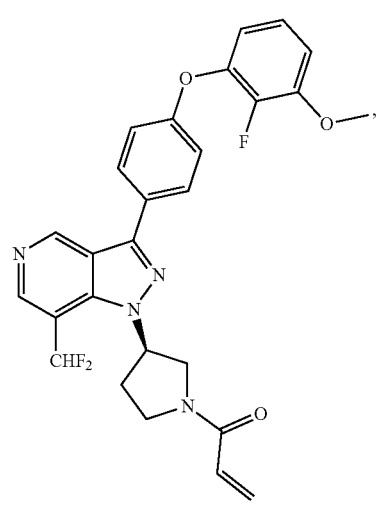
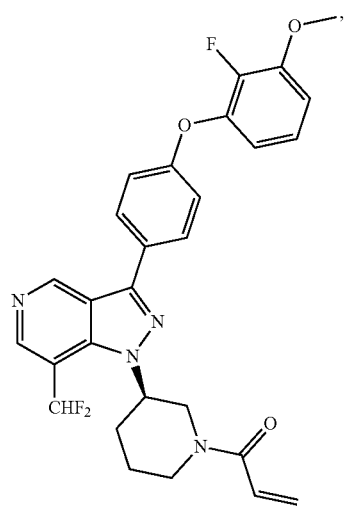
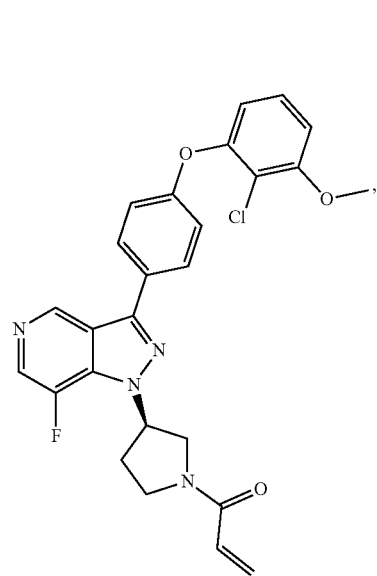
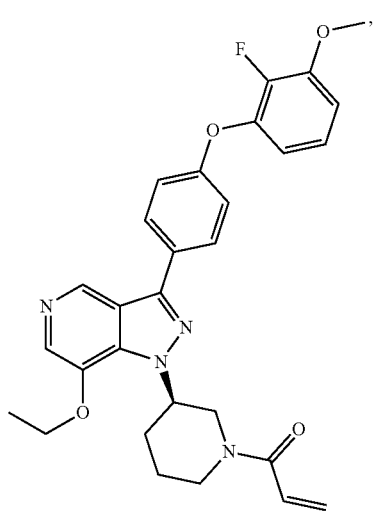

163
-continued
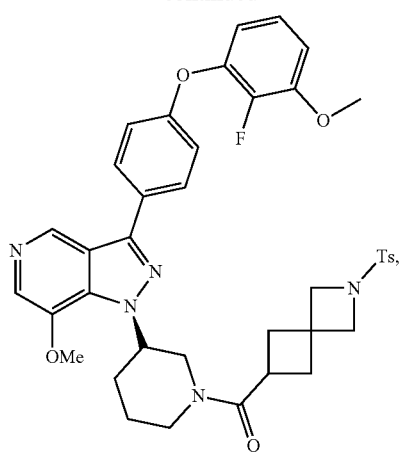
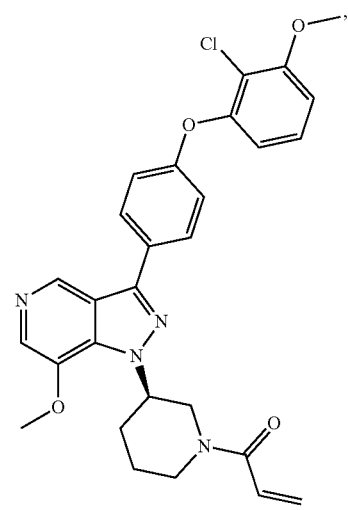
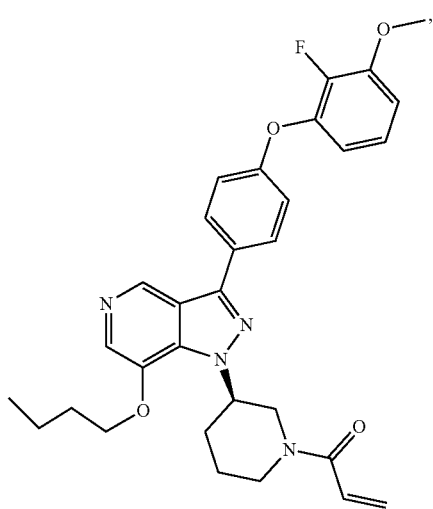
164
-continued
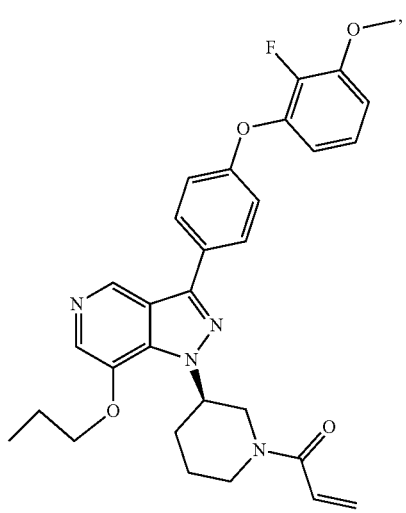
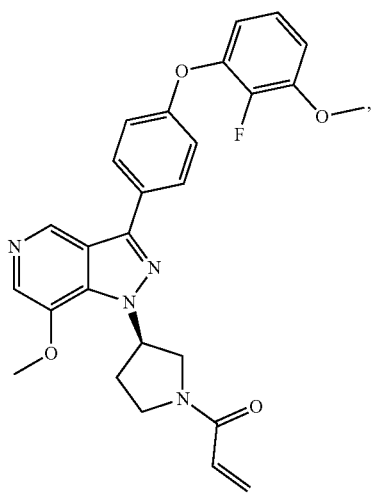
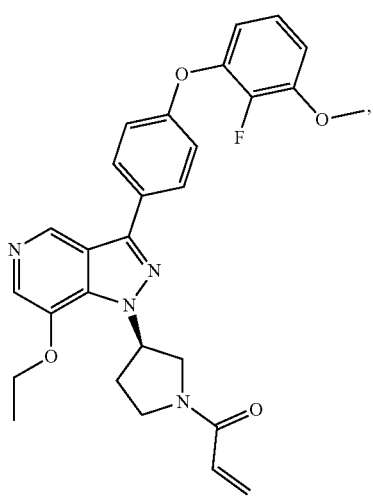

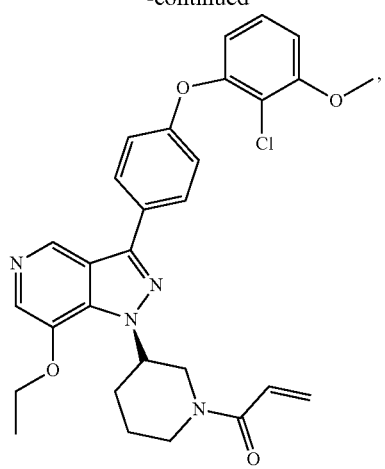
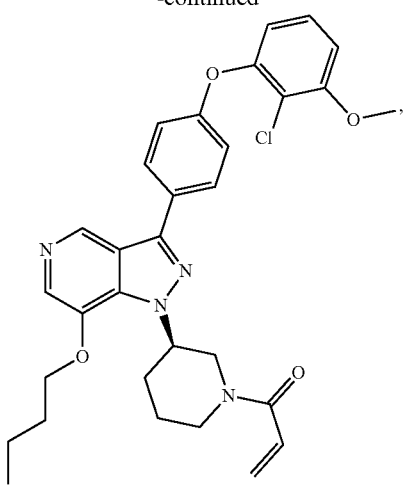
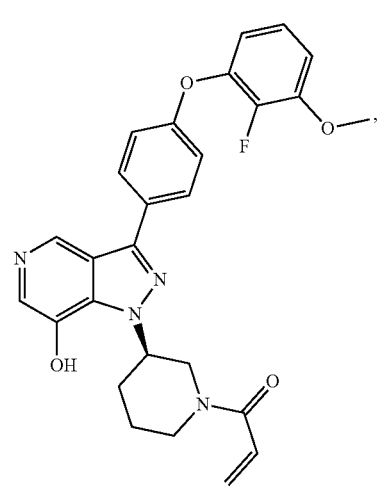
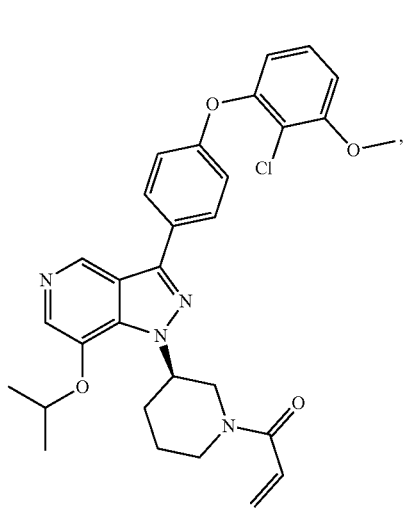
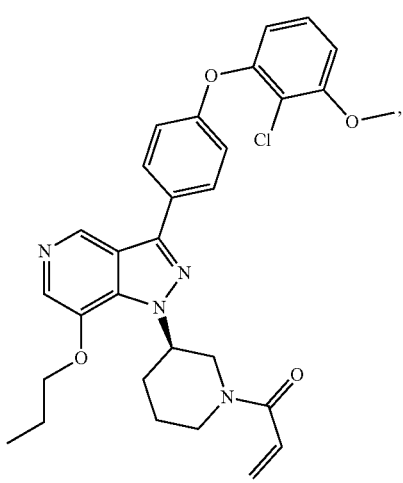

167
-continued
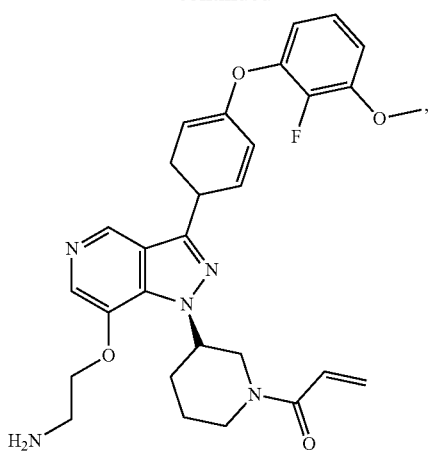
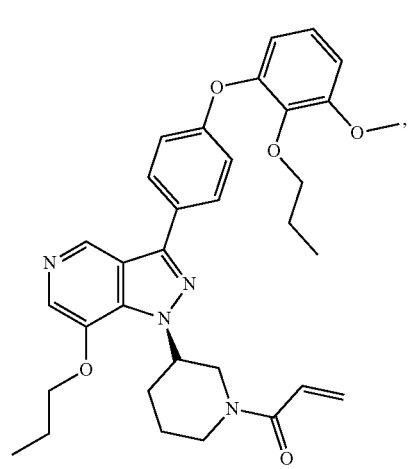
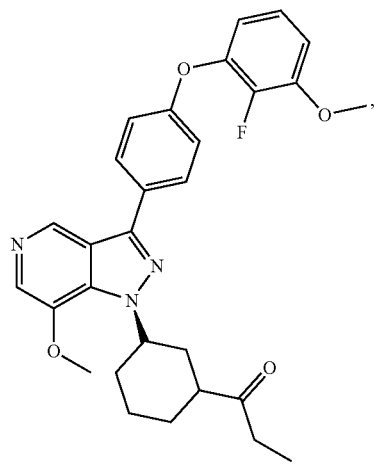
168
-continued
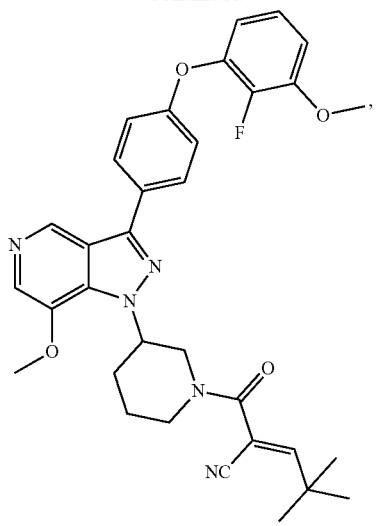
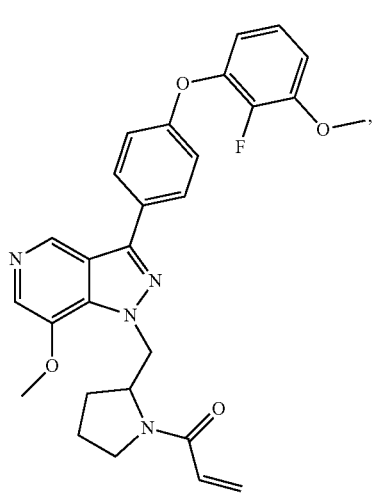
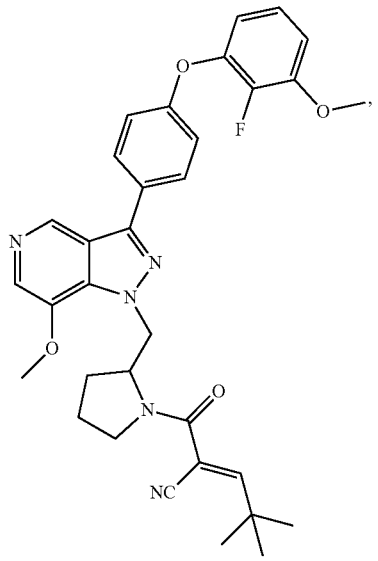

169
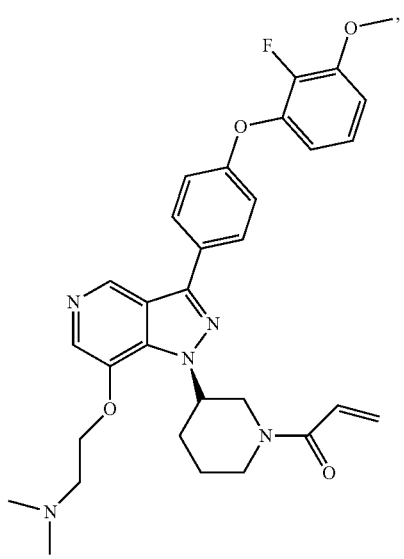
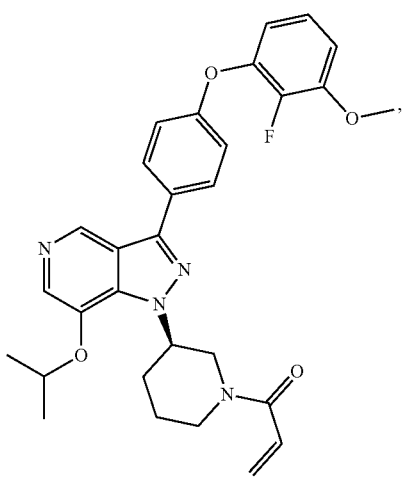
170
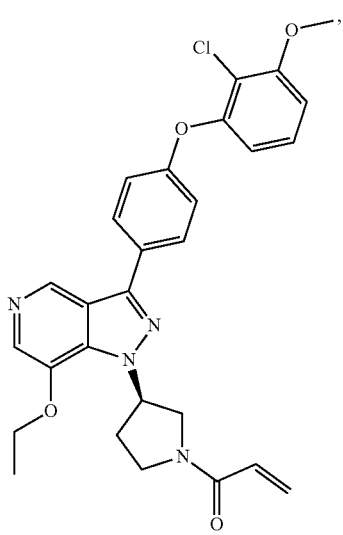
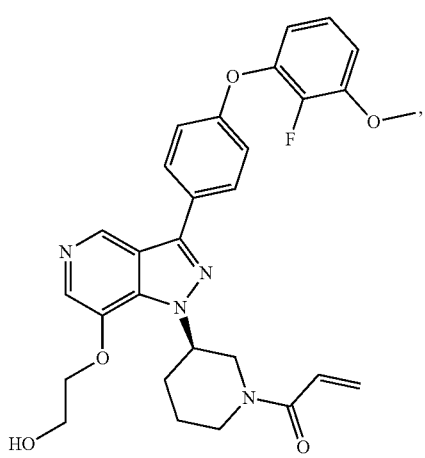

171
-continued

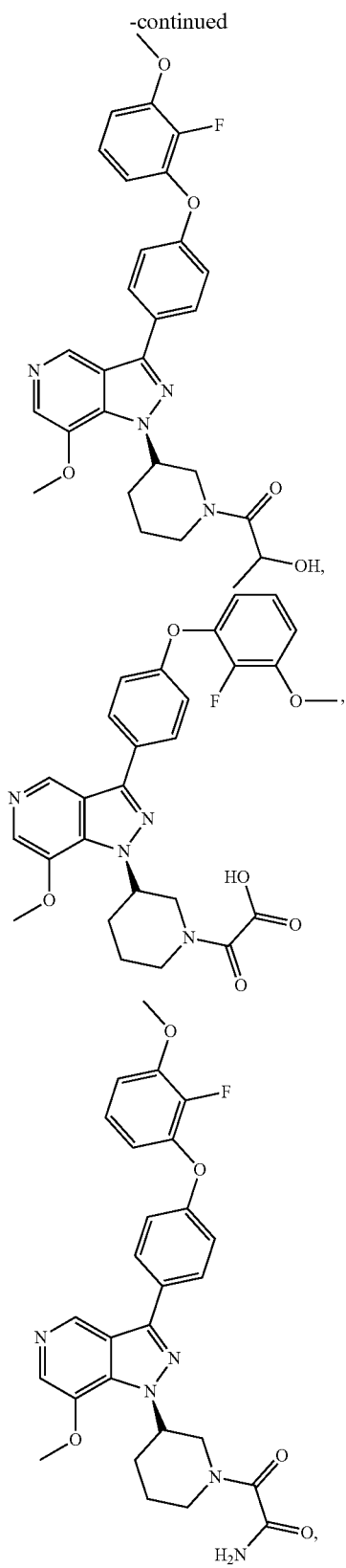

172
-continued

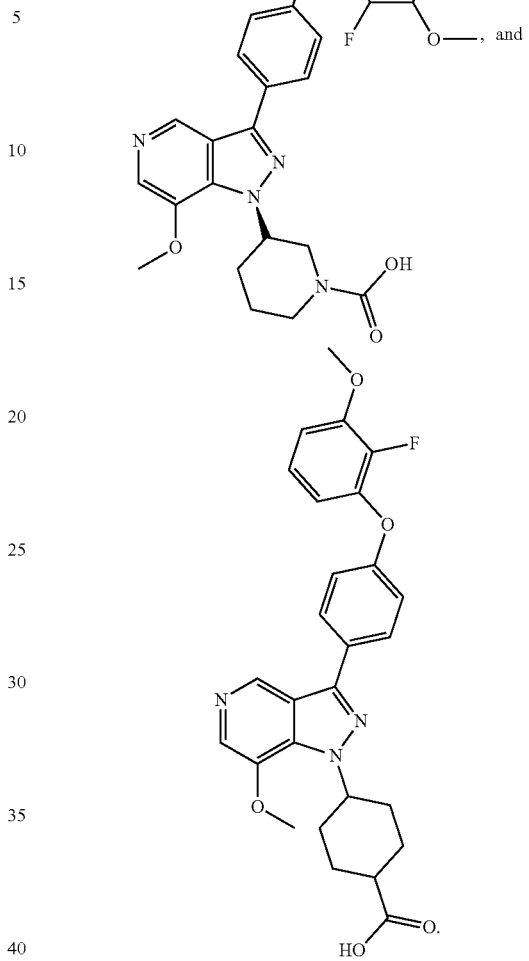

7. A pharmaceutical composition comprising a therapeutically effective amount of the compound of claim 1, and a pharmaceutically acceptable excipient.

8. A pharmaceutical composition for treating cancers, tumors, inflammatory diseases, autoimmune diseases, or immunologically mediated disease comprising a therapeutically effective amount of the compound of claim 1, and a pharmaceutically acceptable excipient.

9. A method for treating an autoimmune disease comprising administering to a subject in need thereof a composition containing a therapeutically effective amount of the compound of claim 1.

10. A method for treating an autoimmune disease, cancers, tumors, inflammatory diseases, or immunologically mediated diseases comprising administering to a subject in need thereof a composition containing a therapeutically effective amount of the compound of claim 1 and other therapeutic agents.

* * * * *